United States Patent
Kuboyama et al.

(10) Patent No.: US 9,845,306 B2
(45) Date of Patent: *Dec. 19, 2017

(54) CATIONIC LIPID

(71) Applicant: Kyowa Hakko Kirin Co., Ltd., Tokyo (JP)

(72) Inventors: Takeshi Kuboyama, Tokyo (JP); Tomohiro Era, Tokyo (JP); Tomoyuki Naoi, Tokyo (JP)

(73) Assignee: KYOWA HAKKO KIRIN CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/828,751

(22) Filed: Aug. 18, 2015

(65) Prior Publication Data
US 2015/0343062 A1   Dec. 3, 2015

Related U.S. Application Data

(63) Continuation of application No. 13/643,342, filed as application No. PCT/JP2011/060458 on Apr. 28, 2011, now Pat. No. 9,408,914.

(30) Foreign Application Priority Data

Apr. 28, 2010  (JP) ................. 2010-104159
Sep. 17, 2010  (JP) ................. 2010-209937

(51) Int. Cl.
| | | |
|---|---|---|
| C07D 401/04 | (2006.01) |
| C07C 217/08 | (2006.01) |
| C07D 211/58 | (2006.01) |
| C07C 219/06 | (2006.01) |
| C07C 237/22 | (2006.01) |
| C07D 491/056 | (2006.01) |
| A61K 47/18 | (2017.01) |
| C07C 217/28 | (2006.01) |
| C07C 219/08 | (2006.01) |
| C07D 207/08 | (2006.01) |
| C07D 207/12 | (2006.01) |
| A61K 47/16 | (2006.01) |
| A61K 47/22 | (2006.01) |
| A61K 9/00 | (2006.01) |

(Continued)

(52) U.S. Cl.
CPC .......... *C07D 401/04* (2013.01); *A61K 9/0019* (2013.01); *A61K 9/1272* (2013.01); *A61K 47/16* (2013.01); *A61K 47/18* (2013.01); *A61K 47/186* (2013.01); *A61K 47/22* (2013.01); *C07C 217/08* (2013.01); *C07C 217/28* (2013.01); *C07C 217/40* (2013.01); *C07C 219/06* (2013.01); *C07C 219/08* (2013.01); *C07C 237/06* (2013.01); *C07C 237/22* (2013.01); *C07C 271/22* (2013.01); *C07D 207/08* (2013.01); *C07D 207/12* (2013.01);

*C07D 211/58* (2013.01); *C07D 491/056* (2013.01); *C12N 15/113* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | |
|---|---|---|
| 5,049,386 A | 9/1991 | Eppstein et al. |
| 5,994,317 A | 11/1999 | Wheeler |

(Continued)

FOREIGN PATENT DOCUMENTS

| | | |
|---|---|---|
| DE | 197 58 272 | 4/1999 |
| EP | 0 063 356 | 10/1987 |

(Continued)

OTHER PUBLICATIONS

International Search Report dated Aug. 9, 2011, in International (PCT) Application No. PCT/JP2011/060458.

(Continued)

*Primary Examiner* — Celeste A Roney
(74) *Attorney, Agent, or Firm* — Wenderoth, Lind & Ponack, L.L.P.

(57) ABSTRACT

The present invention provides a cationic lipid, which allow nucleic acids to be easily introduced into cells, represented by formula (I)
(wherein: $R^1$ and $R^2$ are, the same or different, alkenyl, etc, and
$X^1$ and $X^3$ are hydrogen atoms, or are combined together to form a single bond or alkylene, and
$X^3$ is absent or is alkyl, etc,
Y is absent or anion,
a and b are, the same or different, 0 to 3, and
$L^3$ is a single bond, etc,
$R^3$ is alkyl, etc,
$L^1$ and $L^2$ are —O—, —CO—O— or —O—CO—),
a composition comprising the cationic lipid and a nucleic acid, and
a method for introducing a nucleic acid into a cell by using the composition comprising the cationic lipid and the nucleic acid, and the like.

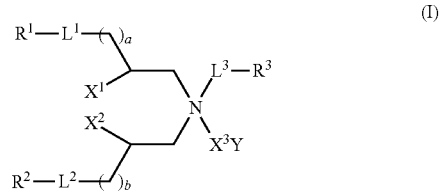

(I)

12 Claims, 7 Drawing Sheets

(51) Int. Cl.
  *A61K 9/127*  (2006.01)
  *C12N 15/113*  (2010.01)
  *C07C 217/40*  (2006.01)
  *C07C 237/06*  (2006.01)
  *C07C 271/22*  (2006.01)

(56) References Cited

U.S. PATENT DOCUMENTS

| | | | |
|---|---|---|---|
| 2009/0023215 A1 | 1/2009 | Jessee et al. | |
| 2011/0009641 A1* | 1/2011 | Anderson | A61K 9/1617 548/340.1 |

FOREIGN PATENT DOCUMENTS

| | | |
|---|---|---|
| EP | 0 636 356 | 12/2000 |
| EP | 1 264 874 | 3/2005 |
| JP | 61-161246 | 7/1986 |
| JP | 2000-508642 | 7/2000 |
| JP | 2006-254877 | 9/2006 |
| JP | 2009-536030 | 10/2009 |
| WO | 91/16024 | 10/1991 |
| WO | 97/19675 | 6/1997 |
| WO | 97/37966 | 10/1997 |
| WO | 00/30444 | 6/2000 |
| WO | 2005/121348 | 12/2005 |
| WO | 2009/086558 | 7/2009 |
| WO | 2009/132131 | 10/2009 |
| WO | 2010/042877 | 4/2010 |
| WO | 2010/054384 | 5/2010 |
| WO | 2010/054401 | 5/2010 |
| WO | 2010/054406 | 5/2010 |
| WO | WO-2010-054384 * | 5/2010 |
| WO | 2011/000107 | 1/2011 |
| WO | 2011/136369 | 11/2011 |

OTHER PUBLICATIONS

Robert A. Moss et al., "Relation of Surfactant Monomer Structure to Flip-Flop Dynamics in Surface-Differentiated Synthetic Bilayer Membranes", Journal of American Chemical Society, 1990, vol. 112, No. 17, pp. 6391-6392.

Ken-ichi Kusumoto et al., "Thin-film assembly of diethanolamine-based lipidic material as potential gene carrier in mouse embryonic neural stem cells", Journal of Biomedical Materials Research Part A, vol. 91A, No. 1, pp. 1-10.

Igor Solodin et al., Synthesis of Amphiphilic Derivatives of N-Methyldiethanolamine. Cationic Lipids 5[1], Synlett, vol. 7, p. 620.

* cited by examiner

CATIONIC LIPID

TECHNICAL FIELD

The present invention relates to a novel cationic lipid that allows, for example, nucleic acid to be easily introduced into cells, and to a novel composition comprising the cationic lipid, and the like.

BACKGROUND ART

Cationic lipids are amphiphilic molecules that generally contain a lipophilic region containing one or more hydrocarbon groups, and a hydrophilic region containing at least one positively charged polar head group. Cationic lipids are useful, because cationic lipids facilitate entry of macromolecules such as nucleic acids into the cytoplasm through the cell plasma membrane by forming a positively charged (total charge) complex with macromolecules such as nucleic acids. This process, performed in vitro and in vivo, is known as transfection.

Typically, cationic lipids are used either alone, or in combination with neutral lipids such as phospholipids. A combination of cationic lipids and neutral lipids is known to be useful, because it can easily form a vesicle that contains an aligned lipid bilayer. Vesicles and liposomes formed by cationic lipids either alone or in combination with neutral lipids have many positive charges on the surface, and, with these charges, can form a complex with polynucleotides or other anionic molecules such as negatively charged proteins. The remaining total cationic charge on the surface of a polynucleotide/cationic lipid/neutral lipid complex can cause strong interaction with the cell membrane, mainly with the negative charge on the surface of the cell membrane.

To date, many different cationic lipids have been synthesized for transfection, and are commercially available. Such cationic lipids include, for example, Lipofectin, Lipofectin ACE, Lipofect AMINE, Transfeactam, DOTAP, etc.

The N-[1-(2,3-dioleyloxy)propyl]-N,N,N-trimethylammonium chloride (DOTMA), etc disclosed in Patent Document 1 are one of the cationic lipids developed in the early. DOTMA etc. are characterized by the propanaminium group having quaternary nitrogen providing a cationic part to the molecule, and a pair of higher hydrocarbons attached to the propyl backbone of the molecule by an ether bond. The quaternary nitrogen is trisubstituted with relatively short alkyl chains such as methyl groups. As structurally similar cationic lipid, N-(2,3-di-(9-(Z)-octadecenoyloxy))-prop-1-yl-N,N,N-trimethylammonium chloride (DOTAP) contains acyl groups, instead of the ether-bonded alkyl groups.

For example, the N-[1-(2,3-dioleyloxypropyl)]-N,N-dimethyl-N-hydroxyethylammonium bromide (DORIE), 2,3-dioleyloxy-N-[2-(spermine carboxamido)ethyl]-N,N-dimethyl-1-propanaminium trifluoroacetate (DOSPA), etc disclosed in Patent Documents 2 and 3 are characterized by the propanaminium group having quaternary nitrogen providing a cationic part to the molecule, and a pair of higher hydrocarbons attached to the propyl backbone of the molecule by an ether bond, the propanaminium group. The quaternary nitrogen is characterized by being trisubstituted with relatively short alkyl chains such as methyl groups, and with hydroxyalkyl.

Patent Document 4 discloses, for example, 1,2-dilinoleyloxy-N,N-dimethylaminopropane (DLinDMA), etc. DLinDMA, etc are characterized by the higher alkyl group that contains at least two unsaturated moieties. The higher alkyl group is contained as a replacement for the higher alkyl groups of the structurally similar cationic lipids DOTAP and DOTMA for the purpose of developing more flexible cationic lipids and improving the membrane fluidity of liposomes or the like. Patent Document 5 discloses, for example, 2,2-dilinoleyl-4-dimethylaminomethyl-[1,3]-dioxolan (DLin-K-DMA), etc.

CITATION LIST

Patent Documents

[Patent Document 1] Japanese Published Unexamined Patent Application No. 161246/1986 (U.S. Pat. No. 5,049,386)
[Patent Document 2] WO1991/16024
[Patent Document 3] WO1997/019675
[Patent Document 4] WO2005/121348
[Patent Document 5] WO2009/086558

SUMMARY OF THE INVENTION

Problems to be Solved by the Invention

An object of the present invention is to provide a novel cationic lipid that allows, for example, nucleic acids to be easily introduced into cells, and a novel composition comprising the cationic lipid, and the like.

Means for Solving the Problems

The present invention is concerned with the following (1) to (27).

(1) A cationic lipid represented by formula (I):

[Chemical Formula 1]

$$R^1-L^1-(\ )_a \quad X^1 \quad L^3-R^3 \atop X^2 \quad N \atop R^2-L^2-(\ )_b \quad X^3Y \qquad (I)$$

(wherein:
$R^1$ and $R^2$ are, the same or different, each linear or branched alkyl, alkenyl or alkynyl having 12 to 24 carbon atoms, or $R^1$ and $R^2$ are combined together to form dialkylmethylene, dialkenylmethylene, dialkynylmethylene or alkylalkenylmethylene,
$X^1$ and $X^2$ are hydrogen atoms, or are combined together to form a single bond or alkylene,
$X^3$ is absent or is alkyl having 1 to 6 carbon atoms, or alkenyl having 3 to 6 carbon atoms,
  when $X^3$ is absent,
  Y is absent, a and b are 0, $L^3$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, and $L^1$ and $L^2$ are —O—, Y is absent, a and b are, the same or different, 0 to 3, and are not 0 at the same time, $L^3$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, $L^1$ and $L^2$ are, the same or different, —O—, —CO—O— or —O—CO—, Y is absent, a and b are, the same or different, 0 to 3, $L^3$ is a single bond, $R^3$ is a hydrogen atom, and $L^1$ and $L^2$ are, the same or different, —O—, —CO—O— or —O—CO—, or Y is absent, a and b are, the same or different, 0 to 3, $L^3$ is —CO— or —CO—O—, $R^3$ is pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl, and $L^1$ and $L^2$ are, the same or different, —O—, —CO—O— or —O—CO—, and when $X^3$ is alkyl having 1 to 6 carbon atoms or alkenyl having 3 to 6 carbon atoms, Y is a pharmaceutically acceptable anion, a and b are, the same or different, 0 to 3, $L^3$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, $L^1$ and $L^2$ are, the same or different, —O—, —CO—O— or —O—CO—).

(2) the cationic lipid as set forth above in (1), wherein $L^1$ and $L^2$ are —O— or —O—CO—, and $R^1$ and $R^2$ are dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadec-9,12-dienyl, (9Z,12Z,15Z)-octadec-9,12,15-trienyl, (Z)-icos-11-enyl, (11Z,14Z)-icos-11,14-dienyl, 3,7,11-trimethyldodeca-2,6,10-trienyl or 3,7,11,15-tetramethylhexadec-2-enyl.

(3) The cationic lipid as set forth above in (1), wherein $L^1$ and $L^2$ are —CO—O—, and $R^1$ and $R^2$ are tridecyl, pentadecyl, heptadecyl, nonadecyl, heneicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadec-8,11-dienyl, (8Z,11Z,14Z)-octadec-8,11,14-trienyl, (Z)-nonadec-10-enyl, (10Z,13Z)-nonadec-10,13-dienyl, (11Z,14Z)-icos-11,14-dienyl, 2,6,10-trimethylundec-1,5,9-trienyl or 2,6,10,14-tetramethylpentadec-1-enyl.

(4) The cationic lipid as set forth above in any one of (1) to (3), wherein a and b are both 0 or 1.

(5) The cationic lipid as set forth above in any one of (1) to (4), wherein $L^3$ is a single bond, $R^3$ is a hydrogen atom, methyl, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, and $L^1$ and $L^2$ are —O—.

(6) The cationic lipid as set forth above in any one of (1) to (5), wherein $L^3$ is —CO— or —CO—O—, $R^3$ is pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl, and $L^1$ and $L^2$ are identically —CO—O— or —O—CO—.

(7) The cationic lipid as set forth above in any one of (1) to (6), wherein $X^1$ and $X^2$ are combined together to form a single bond or alkylene.

(8) The cationic lipid as set forth above in any one of (1) to (5), wherein $X^1$ and $X^2$ are combined together to form a single bond or alkylene, and $R^3$ is a hydrogen atom, methyl, or alkyl having 1 to 6 carbon atoms or alkenyl having 3 to 6 carbon atoms substituted with 1 to 3 substituent(s), which is (are), the same or different, amino, hydroxy or carbamoyl.

(9) The cationic lipid as set forth above in any one of (1) to (5), wherein $X^1$ and $X^2$ are hydrogen atoms, and $R^3$ is a hydrogen atom, methyl, or alkyl having 1 to 6 carbon atoms or alkenyl having 3 to 6 carbon atoms substituted with 1 to 3 substituent(s), which is (are), the same or different, amino, hydroxy or carbamoyl.

(10) The cationic lipid as set forth above in (6), wherein $X^1$ and $X^2$ are combined together to form a single bond or alkylene, and $R^3$ is alkyl having 1 to 6 carbon atoms or alkenyl having 3 to 6 carbon atoms substituted with 1 to 3 substituent(s), which is (are), the same or different, amino, hydroxy or carbamoyl.

(11) The cationic lipid as set forth above in (6), wherein $X^1$ and $X^2$ are hydrogen atoms, and $R^3$ is alkyl having 1 to 6 carbon atoms or alkenyl having 3 to 6 carbon atoms substituted with 1 to 3 substituent(s), which is (are), the same or different, amino, hydroxy or carbamoyl.

(12) The cationic lipid as set forth above in any one of (1) to (11), wherein $X^3$ is absent or is methyl.

(13) A composition that comprises the cationic lipid as set forth above in any one of (1) to (12), and a nucleic acid.

(14) A composition comprising a complex particle of the cationic lipid as set forth above in any one of (1) to (12) and a nucleic acid, or a complex particle of a nucleic acid and a combination of the cationic lipid and a neutral lipid and/or a polymer.

(15) A composition comprising a lipid particle constituted of a complex particle of the cationic lipid as set forth above in any one of (1) to (12) and a nucleic acid, or a complex particle of a nucleic acid and a combination of the cationic lipid and a neutral lipid and/or a polymer, and a lipid membrane that encapsulates the complex particle.

(16) The composition as set forth above in any one of (13) to (15), wherein the nucleic acid is a nucleic acid having an activity of suppressing the expression of the target gene by utilizing RNA interference (RNAi).

(17) The composition as set forth above in (16), wherein the target gene is a gene associated with tumor or inflammation.

(18) A method for introducing the nucleic acid into a cell by using the composition of any one as set forth above in (14) to (17).

(19) The method as set forth above in (18), wherein the cell is a cell at a tumor or inflammation site of a mammal.

(20) The method as set forth above in (18) or (19), wherein the cell is a cell in the liver, lungs, kidneys or spleen of a mammal.

(21) The method as set forth above in (19) or (20), wherein the method of the introduction into a cell is a method of introduction into a cell by intravenous administration.

(22) A method for treating cancer or inflammatory disease, the method including administering the composition as set forth above in (17) to a mammal.

(23) The method as set forth above in (22), wherein the method of administration is intravenous administration.

(24) A medicament comprising the composition as set forth above in (16) and for treating disease by administration of the composition to a mammal.

(25) The medicament as set forth above in (24), wherein the method of administration is intravenous administration.

(26) A cancer or inflammatory disease therapeutic agent comprising the composition as set forth above in (17) and for treating cancer or inflammatory disease by administration of the composition to a mammal.

(27) The cancer or inflammatory disease therapeutic agent as set forth above in (26), wherein the method of administration is intravenous administration.

Advantage of the Invention

A composition comprising the novel cationic lipid of the present invention and a nucleic acid can be administered to mammals, etc and, for example, the like to easily introduce the nucleic acid into cells and the like.

MODE FOR CARRYING OUT THE INVENTION

Figure 1:
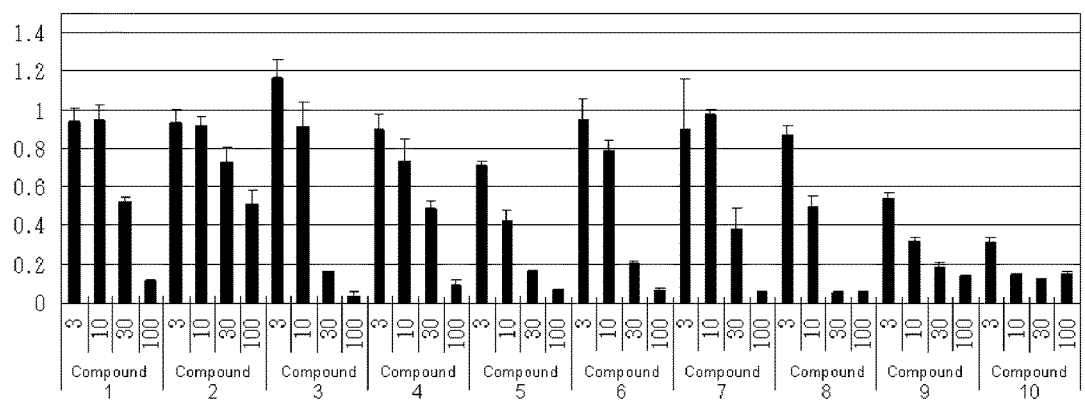
FIG. 1 shows the expression rate of target gene mRNA after the introduction of the preparations obtained in Example 118 (preparations using compounds 1 to 10) into human liver cancer-derived cell line HepG2. The vertical axis represents target gene mRNA expression rate relative to the negative control taken at 1; the horizontal axis represents nucleic acid concentration (nM), and the compound numbers of the cationic lipids used.
Figure 2:
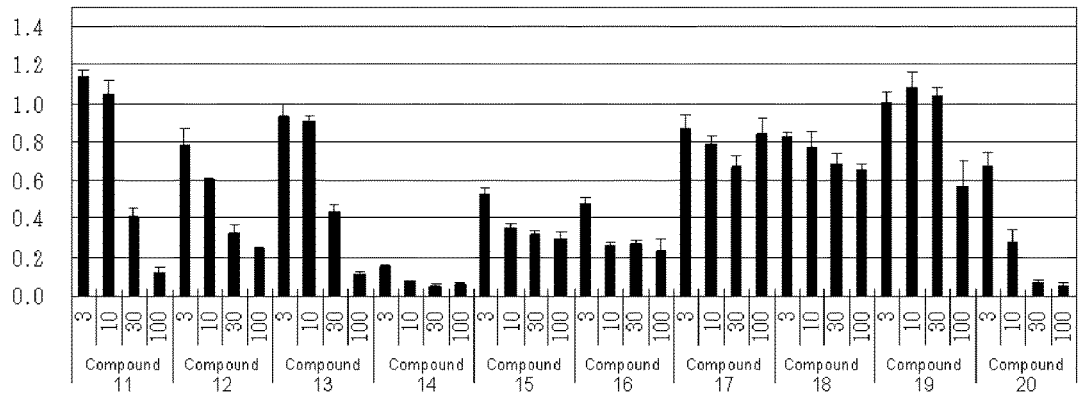
FIG. 2 shows the expression rate of target gene mRNA after the introduction of the preparations obtained in Example 118 (preparations using compounds 1 to 10) into cells as that in FIG. 1.
Figure 3:
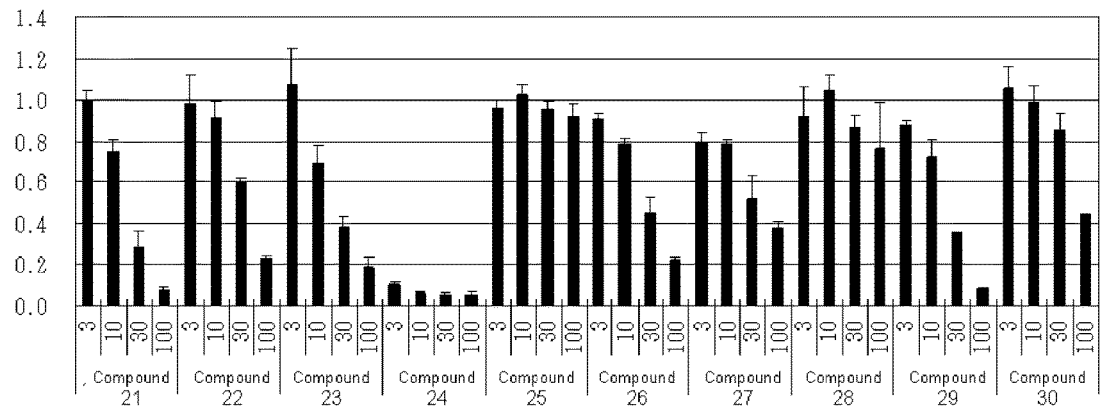
FIG. 3 shows the expression rate of target gene mRNA after the introduction of the preparations obtained in Example 118 (preparations using compounds 21 to 30) into cells as that in FIG. 1.
Figure 4:
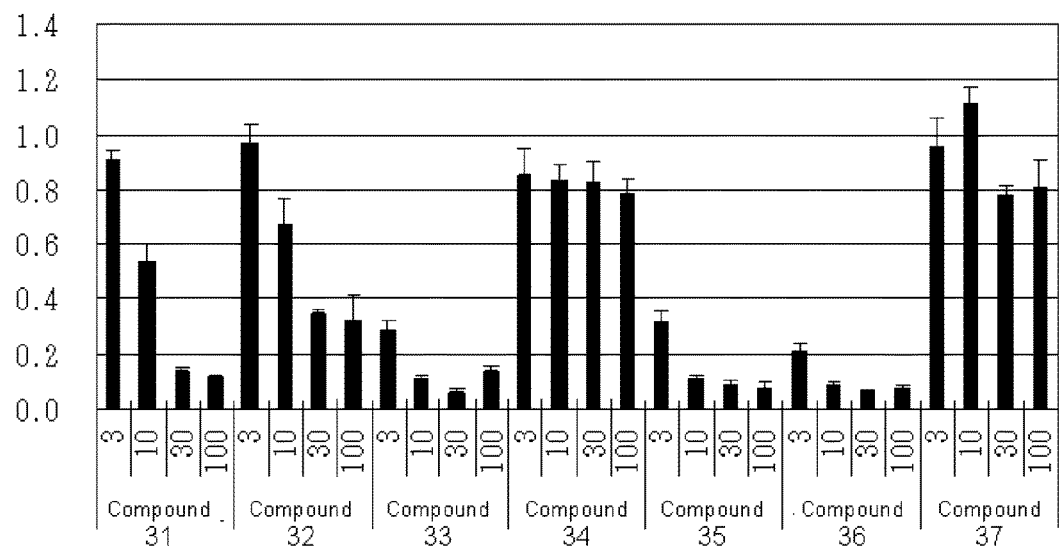
FIG. 4 shows the expression rate of target gene mRNA after the introduction of the preparations obtained in Example 118 (preparations using compounds 31 to 37) into cells as that in FIG. 1.
Figure 5:
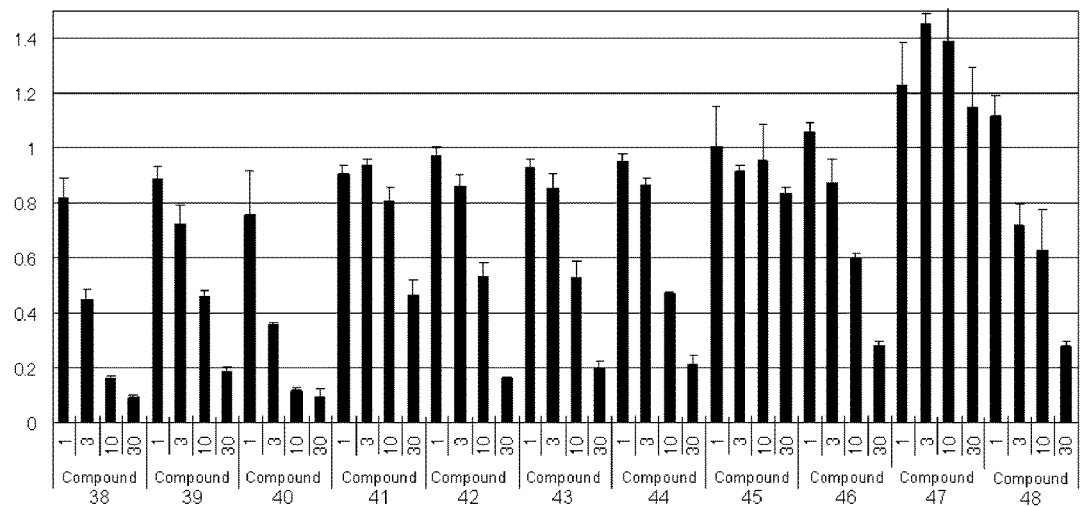
FIG. 5 shows the expression rate of target gene mRNA after the introduction of the preparations obtained in Example 118 (preparations using compounds 38 to 48) into cells as that in FIG. 1.
Figure 6:
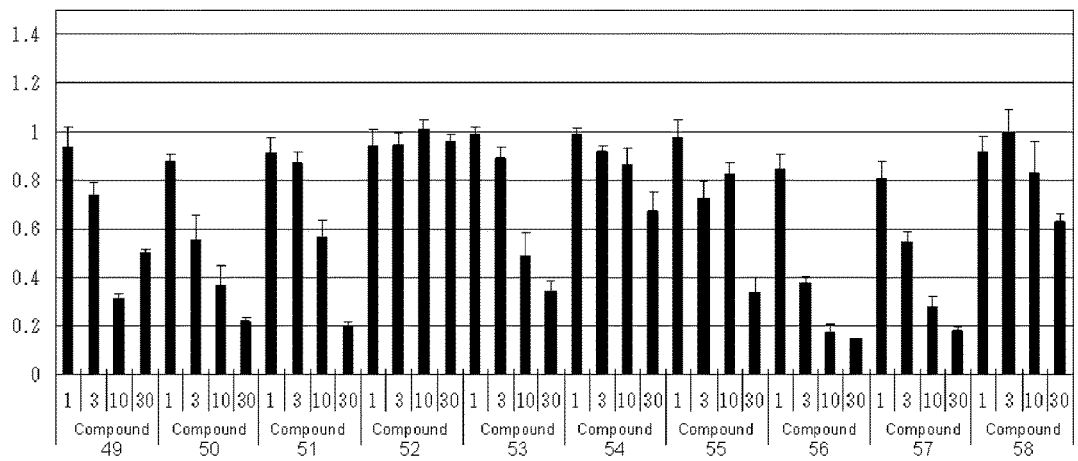
FIG. 6 shows the expression rate of target gene mRNA after the introduction of the preparations obtained in Example 118 (preparations using compounds 49 to 58) into cells as that in FIG. 1.
Figure 7:
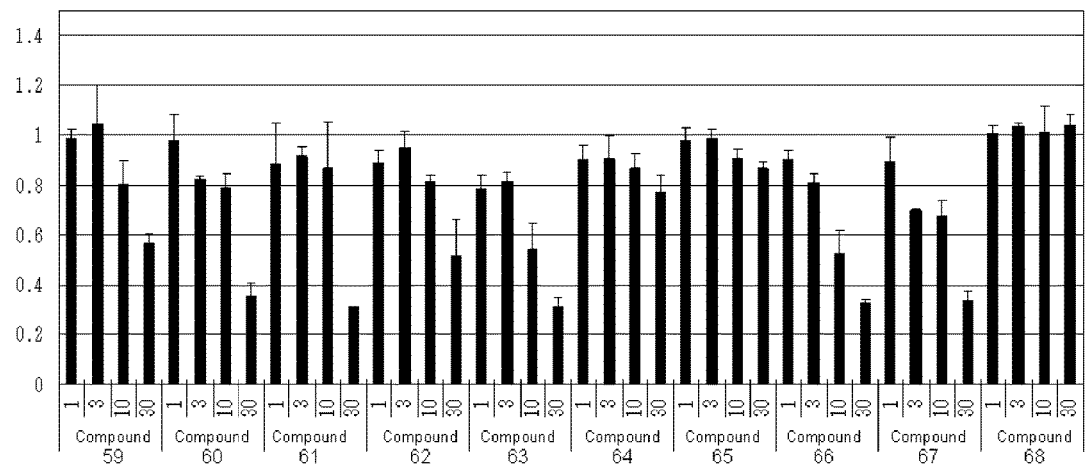
FIG. 7 shows the expression rate of target gene mRNA after the introduction of the preparations obtained in Example 118 (preparations using compounds 59 to 68) into cells as that in FIG. 1.
Figure 8:
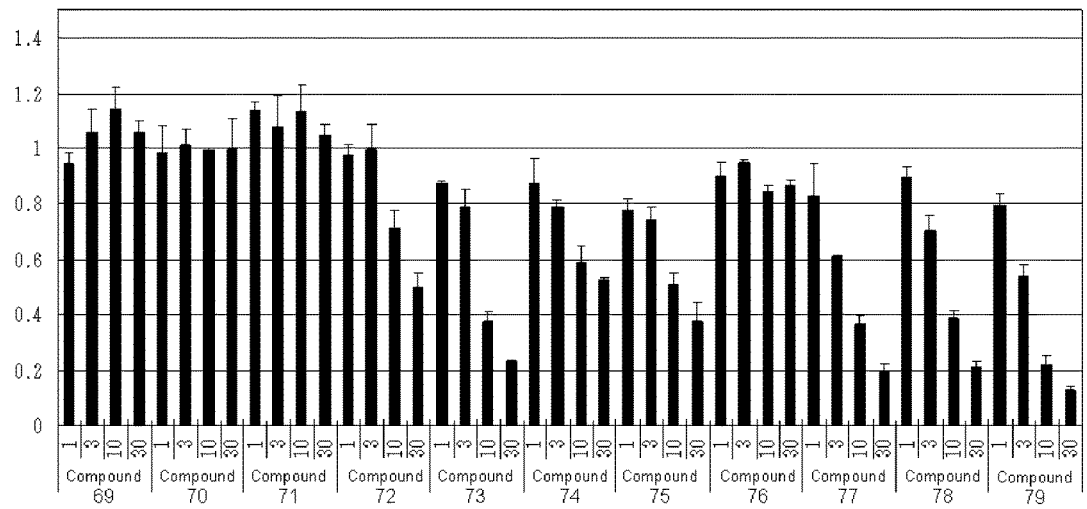
FIG. 8 shows the expression rate of target gene mRNA after the introduction of the preparations obtained in Example 118 (preparations using compounds 69 to 79) into cells as that in FIG. 1.
Figure 9:
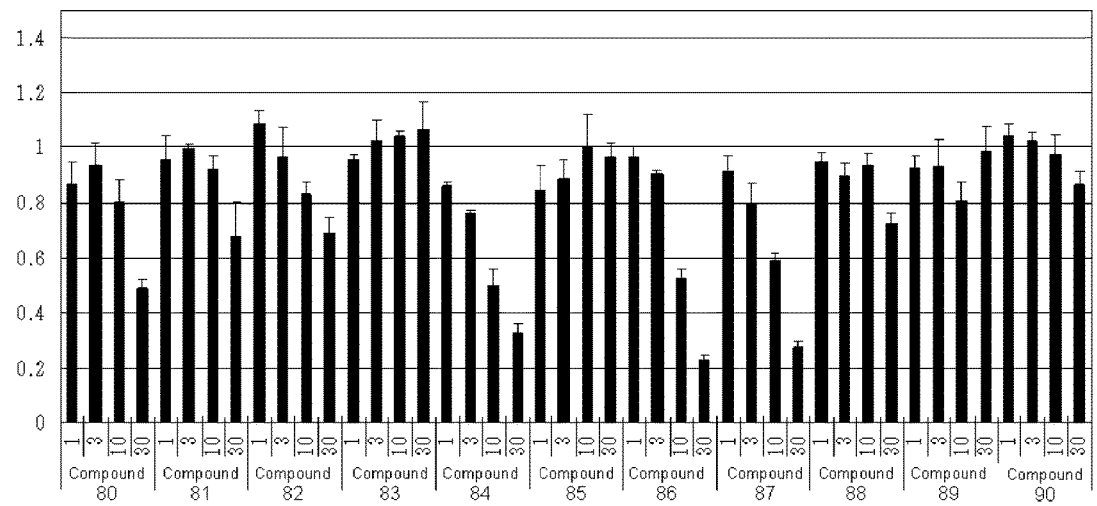
FIG. 9 shows the expression rate of target gene mRNA after the introduction of the preparations obtained in Example 118 (preparations using compounds 80 to 90) into cells as that in FIG. 1.
Figure 10:
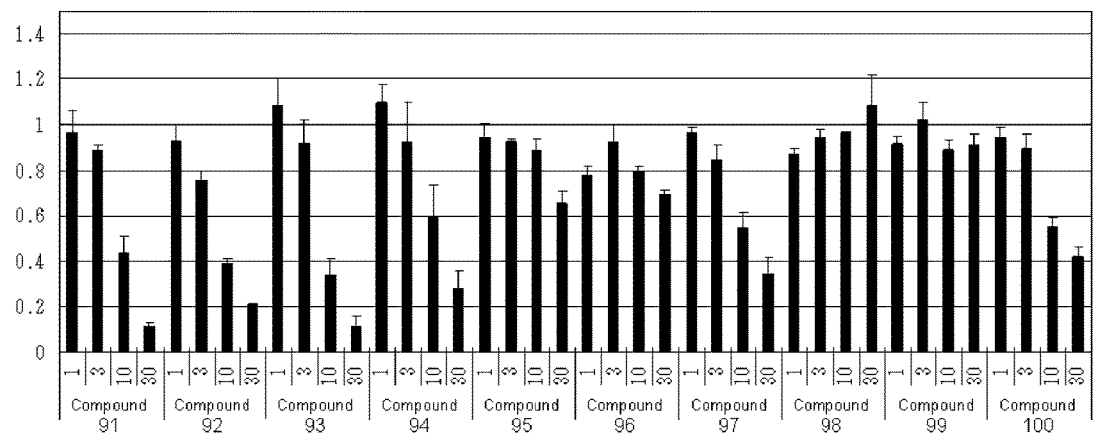
FIG. 10 shows the expression rate of target gene mRNA after the introduction of the preparations obtained in Example 118 (preparations using compounds 91 to 100) into cells as that in FIG. 1.
Figure 11:
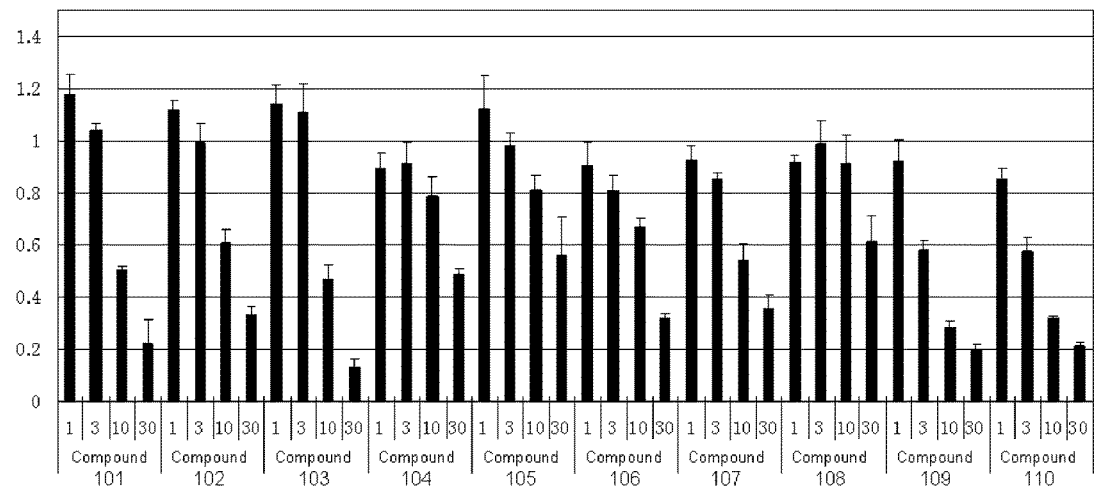
FIG. 11 shows the expression rate of target gene mRNA after the introduction of the preparations obtained in Example 118 (preparations using compounds 101 to 110) into cells as that in FIG. 1.
Figure 12:
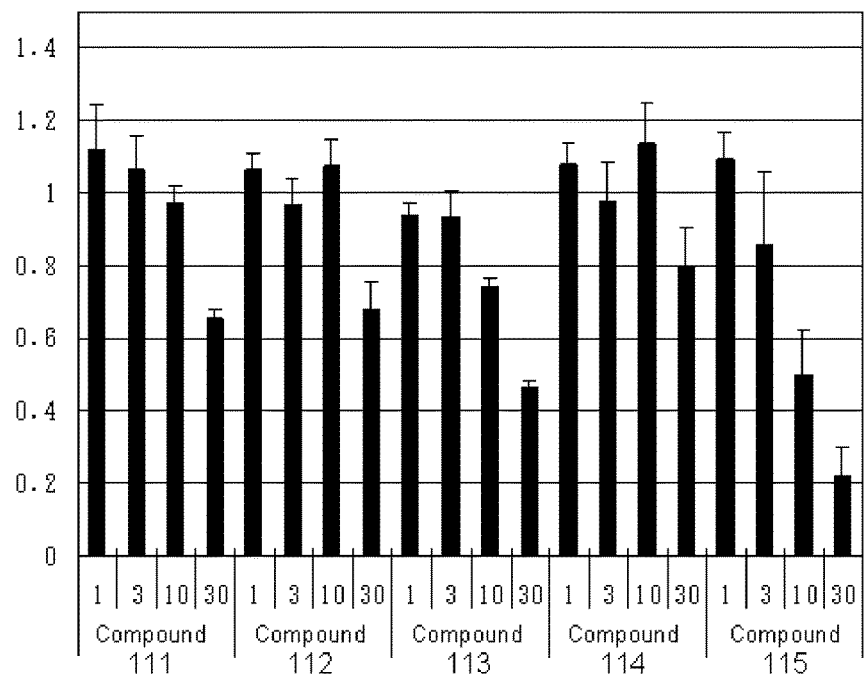
FIG. 12 shows the expression rate of target gene mRNA after the introduction of the preparations obtained in Example 118 (preparations using compounds 111 to 115) into cells as that in FIG. 1.

A cationic lipid of the present invention is represented by the following formula (I):

[Chemical Formula 2]

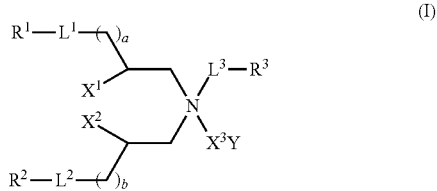

(wherein:
$R^1$ and $R^2$ are, the same or different, each linear or branched alkyl, alkenyl or alkynyl having 12 to 24 carbon atoms, or $R^1$ and $R^2$ are combined together to form dialkylmethylene, dialkenylmethylene, dialkynylmethylene or alkylalkenylmethylene,
$X^1$ and $X^3$ are hydrogen atoms, or are combined together to form a single bond or alkylene,
$X^3$ is absent or represents alkyl having 1 to 6 carbon atoms, or alkenyl having 3 to 6 carbon atoms,
when $X^3$ is absent,
Y is absent, a and b are 0, $L^3$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, and $L^1$ and $L^2$ are —O—, Y is absent, a and b are, the same or different, 0 to 3, and are not 0 at the same time, $L^3$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, $L^1$ and $L^2$ are, the same or different, —O—, —CO—O— or —O—CO—, Y is absent, a and b are, the same or different, 0 to 3, $L^3$ is a single bond, $R^3$ is a hydrogen atom, and $L^1$ and $L^2$ are, the same or different, —O—, —CO—O— or —O—CO—, or Y is absent, a and b are, the same or different, 0 to 3, $L^3$ is —CO— or —CO—O—, $R^3$ is pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl, and $L^1$ and $L^2$ are, the same or different, —O—, —CO—O— or —O—CO—, and when $X^3$ is alkyl having 1 to 6 carbon atoms or alkenyl having 3 to 6 carbon atoms, Y is a pharmaceutically acceptable anion, a and b are, the same or different, 0 to 3, $L^3$ is a single bond, $R^3$ is alkyl having 1 to 6 carbon atoms, alkenyl having 3 to 6 carbon atoms, pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, $L^1$ and $L^2$ are, the same or different, —O—, —CO—O— or —O—CO—).

The compound represented by the formula (I) will be hereinafter also referred to as "Compound (I)". The same is also applicable to compounds designated with other numbers.

In the definition of each group in formula (I), examples of the linear or branched alkyl having 12 to 24 carbon atoms include dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, heneicosyl, docosyl, tricosyl, tetracosyl, and the like.

The linear or branched alkenyl having 12 to 24 carbon atoms may be a linear or branched alkenyl having 12 to 24 carbon atoms and having 1 to 3 double bonds. Examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl, and 3,7,11,15-tetramethylhexadec-2-enyl. Of these, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl, (9Z,12Z)-octadeca-9,12-dienyl, and the like are preferable.

The linear or branched alkynyl having 12 to 24 carbon atoms may be a linear or branched alkynyl having 12 to 24 carbon atoms and having 1 to 3 triple bonds. Examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl, and octadec-9-ynyl.

Examples of the alkylene include methylene, ethylene, propylene, and the like.

Examples of the alkyl having 1 to 6 carbon atoms include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl, and cyclohexyl. Of these, methyl, ethyl, propyl, isopropyl, butyl, isobutyl, sec-butyl, tert-butyl, pentyl, isopentyl, sec-pentyl, tert-pentyl, neopentyl, hexyl, and the like are preferable, with methyl, ethyl, propyl, and the like being more preferable.

Examples of the alkenyl having 3 to 6 carbon atoms include allyl, 1-propenyl, butenyl, pentenyl, and hexenyl. Of these, allyl or the like is preferable.

The alkyl moiety in the substituted alkyl having 1 to 6 carbon atoms and the alkenyl moiety in the substituted alkenyl having 3 to 6 carbon atoms have the same definitions of the alkyl having 1 to 6 carbon atoms and the alkenyl having 3 to 6 carbon atoms as described above, respectively.

The alkyl, alkenyl, and alkynyl moieties in the dialkylmethylene, dialkenylmethylene, dialkynylmethylene or alkylalkenylmethylene have the same definitions as the linear or branched alkyl having 12 to 24 carbon atoms, the linear or branched alkenyl having 12 to 24 carbon atoms, and the linear or branched alkynyl having 12 to 24 carbon atoms, respectively. In addition, it is further preferable that the dialkylmethylene, dialkenylmethylene, and dialkynylmethylene have the same alkyl, alkenyl, and alkynyl moieties, respectively.

In the present invention, examples of the pharmaceutically acceptable anions include inorganic ions such as chloride ions, bromide ions, nitric acid ions, sulfuric acid ions, and phosphoric acid ions, organic acid ions such as acetic acid ions, oxalic acid ions, maleic acid ions, fumaric acid ions, citric acid ions, benzoic acid ions, and methanesulfonic acid ions, and the like.

In the present invention, each of pyrrolidin-2-yl, pyrrolidin-3-yl, piperidin-2-yl, piperidin-3-yl, piperidin-4-yl, morpholin-2-yl, and morpholin-3-yl includes one in which the hydrogen atom bonded on the nitrogen atom in the ring is converted into methyl or ethyl.

Each of the monoalkylamino and the dialkylamino may be an amino which is substituted with one or two alkyls, being the same or different, and having a carbon number of 1 to 6 (having the same definition as above) or an alkyl or alkyls having a carbon number of 1 to 6 (having the same definition as above) substituted with amino, methylamino, ethylamino, dimethylamino, diethylamino, pyrrolidinyl, piperidyl or morpholinyl. Examples thereof include methylamino, ethylamino, propylamino, butylamino, pentylamino, hexylamino, dimethylamino, diethylamino, ethylmethylamino, methylpropylamino, butylmethylamino, methylpentylamino, hexylmethylamino, aminoethylamino, aminopropylamino, (aminoethyl)methylamino, and bis (aminoethyl)amino. Of these, methylamino, ethylamino, dimethylamino, diethylamino, aminopropylamino, and bis (aminoethyl)amino, and the like are preferable.

In the present invention, the amino, monoalkylamino, and dialkylamino may form ammonio, monoalkylammonio, and dialkylammonio, respectively, through coordination of a hydrogen ion to a lone pair on the nitrogen atom. The amino, monoalkylamino, and dialkylamino include ammonio, monoalkylammonio, and dialkylammonio, respectively.

The trialkylammonio may be an ammonio substituted with three substituents, which are, the same or different, alkyl having 1 to 6 carbon atoms (having the same definition as described above), and alkyl having 1 to 6 carbon atoms (having the same definition as described above) substituted with amino, methylamino, ethylamino, dimethylamino, diethylamino, pyrrolidinyl, piperidyl or morpholinyl. Examples thereof include trimethylammonio, ethyldimethylammonio, diethylmethylammonio, triethylammonio, tripropylammonio, tributylammonio, tripentylammonio, trihexylammonio, tris(aminoethyl)ammonio, (aminoethyl)dimethylammonio, bis(aminoethyl)methylammonio, and the like. Preferred examples thereof include trimethylammonio, triethylammonio, tris(aminoethyl)ammonio, (aminoethyl) dimethylammonio, bis(aminoethyl)methylammonio, and the like.

In the present invention, the ammonio, monoalkylammonio, and dialkylammonio in which a hydrogen ion coordinates to a lone pair on the nitrogen atom of the amino, monoalkylamino, and dialkylamino, respectively, and the trialkylammonio may form salts with pharmaceutically acceptable anions (having the same definitions as described above).

The alkoxy may be hydroxy which is substituted with an alkyl having a carbon number of 1 to 6 (having the same definition as above) or an alkyl having a carbon number of 1 to 6 (having the same definition as above) substituted with amino, methylamino, ethylamino, dimethylamino, diethylamino, pyrrolidinyl, piperidyl or morpholinyl. Examples thereof include methoxy, ethoxy, propyloxy, butyloxy, pentyloxy, hexyloxy, aminoethoxy, and methylaminoethoxy. Of these, methoxy, ethoxy, aminoethoxy, methylaminoethoxy, and the like are preferable.

The monoalkylcarbamoyl and dialkylcarbamoyl may be carbamoyls substituted with one or two substituent(s), which is (are), the same or different, alkyl having 1 to 6 carbon atoms (having the same definition as described above), and alkyl having 1 to 6 carbon atoms (having the same definition as described above) substituted with amino, methylamino, ethylamino, dimethylamino, diethylamino, pyrrolidinyl, piperidyl or morpholinyl. Examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, aminoethylcarbamoyl, aminopropylcarbamoyl, (aminoethyl)methylcarbamoyl, bis(aminoethyl)carbamoyl, and the like. Preferred example thereof include methylcarbamoyl, ethylcarbamoyl, dimethylcarbamoyl, and the like.

In the formula (I), it is more preferable that $R^1$ and $R^2$ be identically linear or branched alkyl, alkenyl or alkynyl having 12 to 24 carbon atoms. Further preferably, $R^1$ and $R^2$ are both linear or branched alkyl or alkenyl having 12 to 24 carbon atoms.

More preferably, $L^1$ and $L^2$ are identically —O—, —CO—O— or —O—CO—.

When at least one of $L^1$ and $L^2$ is —O—, it is more preferable that the $R^1$ and $R^2$ attached to —O— are, the same or different, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadec-9,12-dienyl, (9Z,12Z,15Z)-octadec-9,12,15-trienyl, (Z)-icos-11-enyl, (11Z,14Z)-icos-11,14-dienyl, 3,7,11-trimethyldodeca-2,6,10-trienyl or 3,7,11,15-tetramethylhexadec-2-enyl, or that the $R^1$ and $R^2$ are combined together to form dialkylmethylene or dialkenylmethylene. Further preferably, $R^1$ and $R^2$ are tetradecyl, hexadecyl, octadecyl, (Z)-hexadec-9-enyl, (Z)-octadec-6-enyl, (Z)-octadec-9-enyl or (9Z,12Z)-octadec-9,12-dienyl, respectively, or are combined together to form di(tetradecyl)methylene, di(hexadecyl)methylene, di(octadecyl)methylene, di((Z)-hexadec-9-enyl)methylene, di((Z)-octadec-6-enyl)methylene, di((Z)-octadec-9-enyl) methylene or di((9Z,12Z)-octadec-9,12-dienyl)methylene. In all of the case, it is even more preferable that $R^1$ and $R^2$ are the same or are combined together to form dialkylmethylene, dialkenylmethylene or dialkynylmethylene having the same alkyl, alkenyl or alkynyl moieties.

When at least one of $L^1$ and $L^2$ is O—CO—, it is more preferable that the $R^1$ and $R^2$ attached to —O—CO— are, the same or different, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadec-9,12-dienyl, (9Z,12Z,15Z)-octadec-9,12,15-trienyl, (Z)-icos-11-enyl, (11Z,14Z)-icos-11,14-dienyl, 3,7,11-trimethyldodeca-2,6,10-trienyl or 3,7,11,15-tetramethylhexadec-2-enyl. Further preferably, $R^1$ and $R^2$ are tetradecyl, hexadecyl, octadecyl, (Z)-hexadec-9-enyl, (Z)-octadec-6-enyl, (Z)-octadec-9-enyl or (9Z,12Z)-octadec-9,12-dienyl, respectively. In all of the case, it is even more preferable that $R^1$ and $R^2$ are the same.

When at least one of $L^1$ and $L^2$ is —CO—O—, it is more preferable that the $R^1$ and $R^2$ attached to —CO—O— are, the same or different, tridecyl, pentadecyl, heptadecyl, nonadecyl, heneicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadec-8,11-dienyl, (8Z,11Z,14Z)-octadec-8,11,14-trienyl, (Z)-nonadec-10-enyl, (10Z,13Z)-nonadec-10,13-dienyl, (11Z,14Z)-icos-11,14-dienyl, 2,6,10-trimethylundec-1,5,9-trienyl or 2,6,10,14-tetramethylpentadec-1-enyl, or are combined together to form dialkylmethylene, dialkenylmethylene, dialkynylmethylene or alkylalkenylmethylene. It is more preferable that $R^1$ and $R^2$ are tridecyl, pentadecyl, heptadecyl, (Z)-pentadec-8-enyl, (Z)-heptadec-5-enyl, (Z)-heptadec-8-enyl or (8Z,11Z)-heptadec-8,11-dienyl, respectively. In all of the case, it is even more preferable that Wand Ware the same or are combined together to form dialkylmethylene, dialkenylmethylene or dialkynylmethylene having the same alkyl, alkenyl or alkynyl moieties.

It is more preferable that a and b are 0 or 1 at the same time.

When a and b are 1 at the same time, it is preferable that $X^1$ and $X^2$ are combined together to form a single bond or alkylene.

Further preferably, $X^1$ and $X^2$ are combined together to form a single bond or alkylene. When $X^1$ and $X^2$ are combined together to form a single bond or alkylene, $R^3$ is preferably a hydrogen atom, methyl, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, alkylcarbamoyl, dialkylcarbamoyl, pyrrolidinyl, piperidyl or morpholinyl. More preferably, $R^3$ is a hydrogen atom, methyl, or alkyl having 1 to 6 carbon atoms or alkenyl having 3 to 6 carbon atoms substituted with 1 to 3 substituent(s), which is (are), the same or different, amino, hydroxy or carbamoyl. Most preferably, $R^3$ is a hydrogen atom, methyl, 2,3-dihydroxypropyl, 3-hydroxypropyl, aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl, 2-carbamoylethyl, or the like. Further, when $X^1$ and $X^2$ are combined together to form a single bond, $L^3$ is —CO— or —CO—O—, preferably —CO— in one of the preferred modes of the present invention. In this case, $R^3$ is more preferably aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl, or the like, most preferably 1,2-diaminoethyl, 1,3-diaminopropyl, 1,4-diaminobutyl or 1,5-diaminopentyl.

Further, when $X^1$ and $X^2$ are combined together to form a single bond, a and b are, the same or different, 1 to 3, preferably 1 in one of the preferred modes of the present invention. In this case, $L^1$ and $L^2$ are identically —CO—O— or —O—CO—, preferably —CO—O—, and $R^3$ is methyl in one of the more preferred modes of the present invention. In this case, it is more preferable that $R^1$ and $R^2$ are, the same or different, (Z)-heptadec-8-enyl or (8Z,11Z)-heptadec-8,11-dienyl. Most preferably, $R^1$ and $R^2$ are identically (Z)-heptadec-8-enyl or (8Z,11Z)-heptadec-8,11-dienyl.

Further, when $X^1$ and $X^3$ are combined together to form a single bond, $X^3$ is alkyl having 1 to 6 carbon atoms or alkenyl having 3 to 6 carbon atoms, preferably methyl in one of the more preferred modes of the present invention. In this case, it is more preferable that $L^1$ and $L^2$ are identically —CO—O— or —O—CO—, most preferably —CO—O—.

When $X^1$ and $X^3$ are hydrogen atoms, it is more preferable that $R^3$ is a hydrogen atom, methyl, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl. Further preferably, $R^3$ is a hydrogen atom, methyl, or alkyl having 1 to 6 carbon atoms or alkenyl having 3 to 6 carbon atoms substituted with 1 to 3 substituent(s), which is (are), the same or different, amino, hydroxy or carbamoyl. Most preferably, $R^3$ is a hydrogen atom, methyl, 2,3-dihydroxypropyl, 3-hydroxypropyl, aminomethyl, 1,2-diaminoethyl, 2-aminoethyl, 1-amino-2-hydroxyethyl, 1,3-diaminopropyl, 1,4-diaminobutyl, 1,5-diaminopentyl, 3-aminopropyl, 4-aminobutyl, 5-aminopentyl, 2-carbamoylethyl, or the like.

Preferably, $L^3$ is a single bond. When $L^3$ is a single bond, $L^1$ and $L^2$ are more preferably —O—.

Further, when $L^3$ is a single bond, $R^3$ is more preferably a hydrogen atom, methyl, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl. Further preferably, $R^3$ is a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl, 1-methylpiperidin-4-yl, or the like. Most preferably, $R^3$ is a hydrogen atom, methyl, 2,3-dihydroxypropyl, 3-hydroxypropyl, 2-aminoethyl, 3-aminopropyl, 4-aminobutyl, 5-aminopentyl, 2-carbamoylethyl, or the like. In all of the case, $L^1$ and $L^2$ are more preferably —O—.

In one of the more preferred modes of the present invention, $L^1$ and $L^2$ are identically —CO—O— or —O—CO—, preferably —CO—O— when $X^3$ and Y do not exist, $L^3$ is a single bond, and $R^3$ is a hydrogen atom. In this case, it is more preferable that $R^1$ and $R^2$ are, the same or different, (Z)-heptadec-5-enyl or (Z)-heptadec-8-enyl. Most preferably, $R^1$ and $R^2$ are identically (Z)-heptadec-5-enyl or (Z)-heptadec-8-enyl.

Further, when $L^3$ is —CO— or —CO—O—, it is more preferable that $L^1$ and $L^2$ are identically —CO—O— or —O—CO—, further preferably —CO—O—.

When $L^3$ is —CO— or —CO—O—, it is more preferable that $R^3$ is pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl. Further preferably, $R^3$ is aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, 3-(N,N-dimethylamino)propyl, 1-amino-2-hydroxyethyl, or the like. Most preferably, $R^3$ is 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, or the like.

When $L^3$ is —CO— or —CO—O—, $R^3$ is aminomethyl, 1-hydroxy-2-aminoethyl, 2-aminoethyl, 1,3-diaminopropyl, 3-aminopropyl, 1,4-diaminobutyl, 4-aminobutyl, 1,5-diaminopentyl or 5-aminopentyl, and $L^1$ and $L^2$ are identically —O— in one of the more preferred modes of the present invention. In this case, it is more preferable that $R^1$ and $R^2$ are, the same or different, (Z)-octadec-9-enyl or (9Z,12Z)-octadec-9,12-dienyl. Most preferably, $R^1$ and $R^2$ are identically (Z)-octadec-9-enyl or (9Z,12Z)-octadec-9,12-dienyl.

It is more preferable that $X^3$ is absent or is methyl. When $X^3$ is methyl, it is more preferable that $R^3$ is methyl, and that $L^1$ and $L^2$ are identically —CO—O— or —O—CO—, further preferably —CO—O—.

Production methods of Compound (I) are described below. In the following production methods, in the case where the defined group or groups change under the conditions of the production method or are impertinent for carrying out the production method, the target compound can be produced by adopting common introduction and removal methods of a protective group in synthetic organic chemistry [for example, a method described in *Protective Groups in Organic Synthesis, Third Edition*, T. W. Greene, John Wiley & Sons Inc. (1999), etc.]. In addition, if desired, the order of reaction steps such as introduction of a substituent can be altered.

Production Method 1

Among the Compound (I), Compound (Ia) in which $L^1$ and $L^3$ are —O—, $L^3$ is a single bond, and $X^3$ and Y are absent can be produced by the following method.

[Chemical Formula 3]

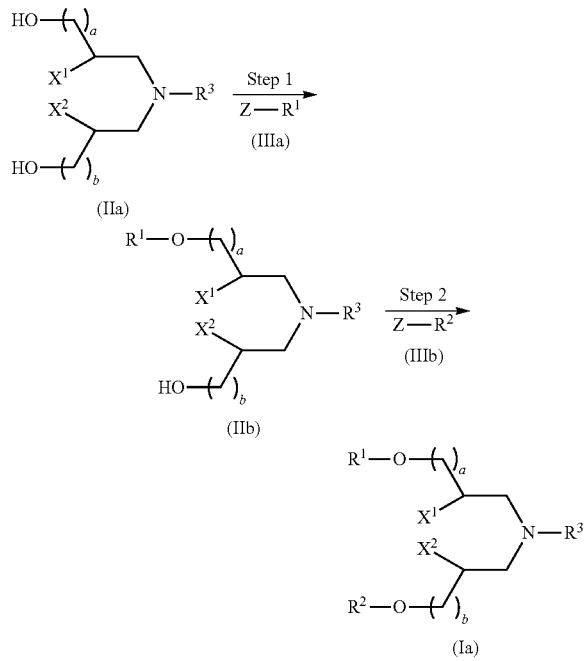

(In the formula, $R^1$, $R^2$, $R^3$, $X^1$, $X^2$, a and b have the same definitions as described above, respectively, and Z represents a leaving group such as a chlorine atom, a bromine atom, an iodine atom, trifluoromethanesulfonyloxy, methanesulfonyloxy, benzenesulfonyloxy, and p-toluenesulfonyloxy.)

Steps 1 and 2

Compound (IIB) can be produced by treating Compound (IIa) and Compound (IIIa) in a solvent in the presence of 1 to 30 equivalents of a base at a temperature between room temperature and 150° C. for 5 minutes to 100 hours, followed by isolation. Compound (Ia) can be produced by treating Compound (IIB) and Compound (IIIb) in a solvent in the presence of 1 to 30 equivalents of a base at a temperature between room temperature and 150° C. for 5 minutes to 100 hours, followed by isolation.

Examples of the solvent include toluene, diethyl ether, tetrahydrofuran, 1,2-dimethoxyethane, dioxane, N,N-dimethylformamide, N-methylpyrrolidone, dimethylsulfoxide, and the like. These may be used either alone or as a mixture.

Examples of the base include sodium hydride, sodium hydroxide, potassium hydroxide, sodium tert-butoxide, potassium tert-butoxide, and the like.

Compound (IIa) can be obtained as a commercially available product or by known methods (for example, *Chemical & Pharmaceutical Bulletin* (*Chem. Pharm. Bull.*), 1991, Vol. 39, p. 2219, and WO2006/10036) or a method in conformity thereof, or by using the methods described in Reference Examples.

Compound (IIIa) and Compound (IIIb) can be obtained as commercially available products or by known methods (for example, Dai 5-han, *Jikken Kagaku Kouza* (5th edition. Courses in Experimental Chemistry) 13, "Synthesis of Organic Compounds I", 5th Ed., p. 374, Maruzen (2005)), or a method in conformity thereof.

Compound (Ia) having the identical $R^1$ and $R^2$ can be obtained by using 2 equivalents or more of the Compound (IIIa) in step 1.

Production Method

Among the Compound (I), Compound (Ib) in which $L^1$ and $L^2$ are —CO—O—, $L^3$ is a single bond, and $X^3$ and Y are absent can be produced by the following method.

[Chemical Formula 4]

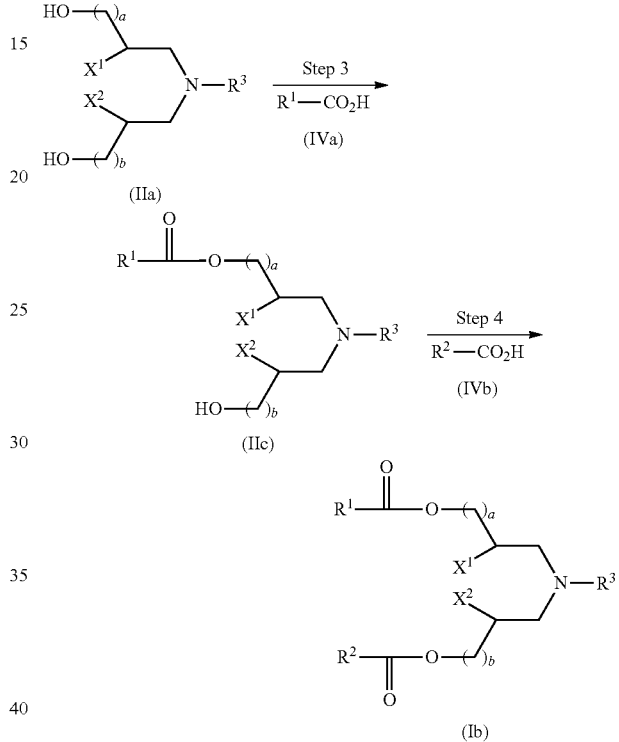

(In the formula, $R^1$, $R^2$, $R^3$, $X^1$, $X^2$, a and b have the same definitions as described above, respectively.)

Steps 3 and 4

Compound (IIc) can be produced by treating Compound (IIa) and Compound (IVa) in a solvent in the presence of 1 to 30 equivalents of a condensing agent at a temperature between −20° C. and 150° C. for 5 minutes to 100 hours, followed by isolation. Compound (Ib) can be produced by treating Compound (IIc) and Compound (IVb) in a solvent in the presence of 1 to 30 equivalents of a condensing agent at a temperature between −20° C. and 150° C. for 5 minutes to 100 hours, followed by isolation. In steps 3 and 4, 0.01 to 30 equivalents of an additive and/or 1 equivalent to large excess amounts of a base may be added to promote the reactions.

Examples of the solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, dimethylsulfoxide, and the like. These may be used either alone or as a mixture.

Examples of the condensing agent include 1,3-dicyclohexylcarbodiimide, 1-ethyl-3-(3-dimethylaminopropyl)carbodiimide.hydrochloride, carbonyldiimidazole, benzotriazol-1-yloxytris(dimethylamino)phosphonium hexafluorophosphate, (benzotriazol-1-yloxy)tripyrrolizinophosphonium hexafluorophosphate, (7-azabenzotriazol-1-yl)-N,N,N',N'-tetramethyluronium hexafluorophosphate, (benzotriazol-1-yl)-N,N,N',N'-tetramethyluronium hexafluorophosphate, 2-chloro-1-methylpyridinium iodide, and the like.

Examples of the additive include 1-hydroxybenzotriazole, 4-dimethylaminopyridine, and the like.

Examples of the base include potassium acetate, sodium bicarbonate, potassium carbonate, potassium hydroxide, sodium hydroxide, sodium methoxide, potassium tert-butoxide, triethylamine, diisopropylethylamine, N-methylmorpholine, pyridine, 8-diazabicyclo[5.4.0]-7-undecene, and the like.

Compound (IVa) and Compound (IVb) can be obtained as commercially available products or by known methods (for example, Dai 5-han, *Jikken Kagaku Kouza* (5*th edition, Courses in Experimental Chemistry*) 16, *Synthesis of Organic Compounds IV*, 5th Ed., p. 1, Maruzen (2005)), or a method in conformity thereof.

Compound (Ib) having the identical $R^1$ and $R^2$ can be obtained by using 2 equivalents or more of Compound (IVa) in step 3.

Production Method 3

Among the Compound (I), Compound (TO in which $L^1$ and $L^2$ are —O—CO—, $L^3$ is a single bond, and $X^3$ and Y are absent can be produced by the following method.

[Chemical Formula 5]

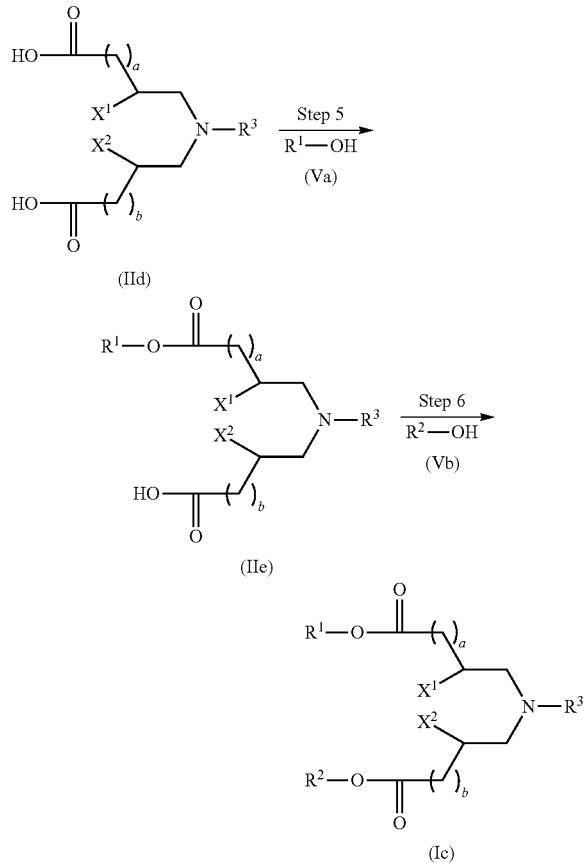

(In the formula, $R^1$, $R^2$, $R^3$, $X^1$, $X^2$, a and b have the same definitions as described above, respectively.)

Steps 5 and 6

Compound (IIe) can be produced by treating Compound (IId) and Compound (Va) in a solvent in the presence of 1 to 30 equivalents of a condensing agent at a temperature between −20° C. and 150° C. for 5 minutes to 100 hours, followed by isolation. Compound (Ic) can be produced by treating Compound (IIe) and Compound (Vb) in a solvent in the presence of 1 to 30 equivalents of a condensing agent at a temperature between −20° C. and 150° C. for 5 minutes to 100 hours, followed by isolation. In steps 5 and 6, 0.01 to 30 equivalents of an additive and/or 1 equivalent to large excess amounts of a base may be added to promote the reactions.

The same solvents, condensing agents, additives, and bases used in production method 2 may be used.

Compound (IId) can be obtained as a commercially available product or by known methods (for example, Dai 5-han, *Jikken Kagaku Kouza* (5*th edition, Courses in Experimental Chemistry*) 16, *Synthesis of Organic Compounds IV*, 5th Ed., p. 1, Maruzen (2005)), or a method in conformity thereof.

Compound (Va) and Compound (Vb) can be obtained as commercially available products or by known methods (for example, Dai 5-han, *Jikken Kagaku Kouza* (5*th edition, Courses in Experimental Chemistry*) 14, *Synthesis of Organic Compounds II*, 5th Ed., p. 1, Maruzen (2005)), or a method in conformity thereof.

Compound (Ic) having the identical $R^1$ and $R^2$ may be obtained by using 2 equivalents or more of Compound (Va) in step 5.

Production Method 4

Among the Compound (I), Compound (Id) in which $L^3$ is a single bond, $R^3$ is a hydrogen atom and, $X^3$ and Y are absent can be produced by the following method.

[Chemical Formula 6]

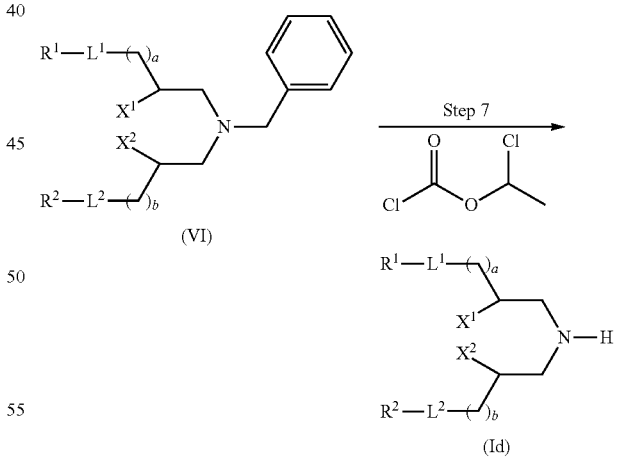

(In the formula, $R^1$, $R^2$, $L^1$, $L^2$, $X^1$, $X^2$, a and b have the same definitions as described above, respectively.)

Step 7

Compound (Id) can be produced by treating Compound (VI) and 1-chloroethyl chloroformate in an inert solvent at a temperature between −20° C. and 230° C. for 5 minutes to 100 hours, and then at a temperature between −20° C. and 230° C. for 5 minutes to 100 hours after adding 1 to large excess amounts of an alcohol.

Examples of the inert solvent include dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and the like. These may be used either alone or as a mixture.

Examples of the alcohol include methanol, ethanol, 1-propanol, 2-propanol, and the like. These may be used either alone or as a mixture.

Compound (VI) can be obtained by using a modified method of production method 1, 2 or 3.

Production Method 5

Among the Compound (I), Compound (Ie) can be produced by the following method. In Compound (Ie), $L^3$ is a single bond, $R^3$ is —$CHR^A R^B$ ($R^A$ and $R^B$ are, the same or different, hydrogen atoms, alkyl having 1 to 5 carbon atoms, alkenyl having 3 to 5 carbon atoms, pyrrolidin-2-yl, pyrrolidin-3-yl, piperidin-2-yl, piperidin-3-yl, piperidin-4-yl, morpholin-2-yl, morpholin-3-yl, or alkyl having 1 to 5 carbon atoms or alkenyl having 3 to 5 carbon atoms substituted with 1 to 3 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, or $R^A$ and $R^B$ are combined together with the adjacent carbon atom thereto to form pyrrolidin-3-yl, piperidin-3-yl or piperidin-4-yl. The sum of the carbon atoms in the alkyl, the alkyl moiety of the substituted alkyl, alkenyl, and the alkenyl moiety of the substituted alkenyl in $R^A$ and $R^B$ is 1 to 5 except when $R^A$ and $R^B$ are both hydrogen atoms. When either of $R^A$ and $R^B$ is pyrrolidin-2-yl, pyrrolidin-3-yl, piperidin-2-yl, piperidin-3-yl, piperidin-4-yl, morpholin-2-yl or morpholin-3-yl, the other is a hydrogen atom, alkyl having 1 to 5 carbon atoms, alkenyl having 3 to 5 carbon atoms, pyrrolidin-2-yl, pyrrolidin-3-yl, piperidin-2-yl, piperidin-3-yl, piperidin-4-yl, morpholin-2-yl, morpholin-3-yl, or alkyl having 1 to 5 carbon atoms or alkenyl having 3 to 5 carbon atoms substituted with 1 or 2 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl. The total number of the substituents is 2 or 3 when $R^A$ and $R^B$ are substituted alkyl or substituted alkenyl), and $X^3$ and Y do not exist.

[Chemical Formula 7]

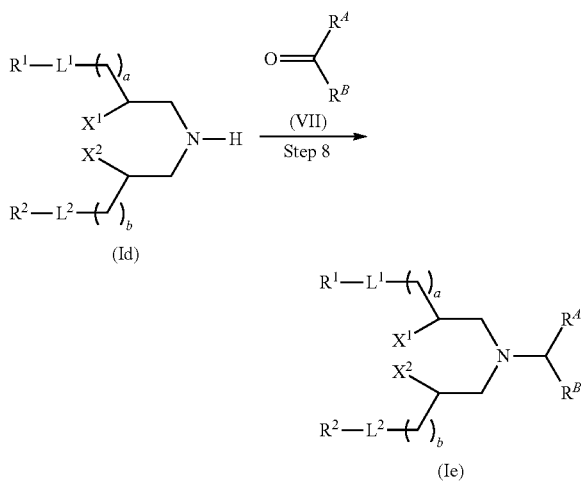

(In the formula, $R^1$, $R^2$, $R^A$, $R^B$, $L^1$, $L^3$, $X^1$, $X^2$, a and b have the same definitions as described above, respectively.)

Step 8

Compound (Ie) can be produced by reacting Compound (Id) with preferably 1 to 10 equivalents of Compound (VII) in a solvent at a temperature between −20° C. and 150° C. for 5 minutes to 72 hours in the presence of preferably 1 to large excess amounts of a reducing agent, and, if necessary, preferably 1 to 10 equivalents of an acid.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, water, and the like. These may be used either alone or as a mixture.

Examples of the reducing agent include sodium triacetoxyborohydride, sodium cyanoborohydride, and the like.

Examples of the acid include hydrochloric acid, acetic acid, and the like.

Compound (VII) can be obtained as a commercially available product or by known methods (for example, Dai 5-han, *Jikken Kagaku Kouza* (5th edition, *Courses in Experimental Chemistry*) 15, *Synthesis of Organic Compounds III*, 5th Ed., p. 1, Maruzen (2005), and Dai 5-han, *Jikken Kagaku Kouza* 15, *Synthesis of Organic Compounds III*, 5th Ed., p. 153, Maruzen (2005)), or a method in conformity thereof.

Production Method 6

Among the Compound (I), Compound (If) in which $L^3$ is a single bond, and $X^3$ and Y are absent can be produced by the following method.

[Chemical Formula 8]

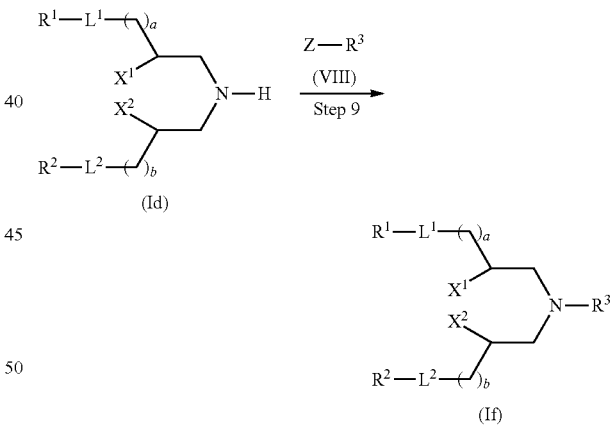

(In the formula, $R^1$, $R^2$, $R^3$, $L^1$, $L^2$, $X^1$, $X^2$, a, b, and Z have the same definitions as described above, respectively.)

Step 9

Compound (If) can be produced by reacting Compound (Id) with Compound (VIII) without solvent or in a solvent at a temperature between −20° C. and 150° C. for 5 minutes to 72 hours, in the presence of preferably 1 to 10 equivalents of an additive, and/or preferably 1 to 10 equivalents of a base, if necessary.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, water, and the like. These may be used either alone or as a mixture.

Examples of the base include potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), and the like.

Examples of the additive include sodium iodide, potassium iodide, tetra-n-butylammonium iodide, and the like.

Compound (VIII) can be obtained as a commercially available product or by known methods (for example, Dai 5-han, *Jikken Kagaku Kouza* (5th edition, *Courses in Experimental Chemistry*) 13, *Synthesis of Organic Compounds I*, 5th Ed., p. 374, Maruzen (2005)), or a method in conformity thereof.

Production Method 7

Among the Compound (I), Compound (Ig) in which $L^3$ is —CO—, and $X^3$ and Y are absent can be produced by the following method.

[Chemical Formula 9]

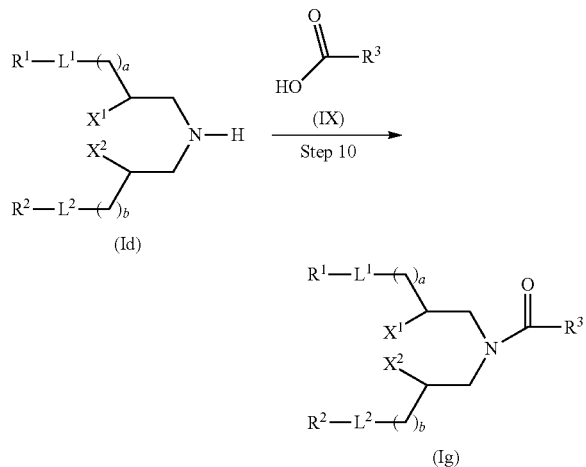

(In the formula, $R^1$, $R^2$, $R^3$, $L^1$, $L^2$, $X^1$, $X^2$, a and b have the same definitions as described above, respectively.)

Step 10

Compound (Ig) can be produced by treating Compound (Id) and Compound (IX) in a solvent at a temperature between −20° C. and 150° C. for 5 minutes to 100 hours in the presence of 1 equivalent to large excess amounts of a condensing agent. If necessary, preferably 0.01 to 10 equivalents of an additive, and/or preferably 1 to large excess amounts of a base may be added to promote the reaction.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, dimethylsulfoxide, water, and the like. These may be used either alone or as a mixture.

The same condensing agents, additives, and bases used in production method 2 may be used.

Compound (IX) can be obtained as a commercially available product or by known methods (for example, Dai 5-han, *Jikken Kagaku Kouza* (5th edition, *Courses in Experimental Chemistry*) 16, *Synthesis of Organic Compounds IV*, 5th Ed., p. 1, Maruzen (2005)), or a method in conformity thereof.

Production Method 8

Among the Compound (I), Compound (Ih) in which $L^3$ is —CO—O—, and $X^3$ and Y are absent can be produced by the following methods.

[Chemical Formula 10]

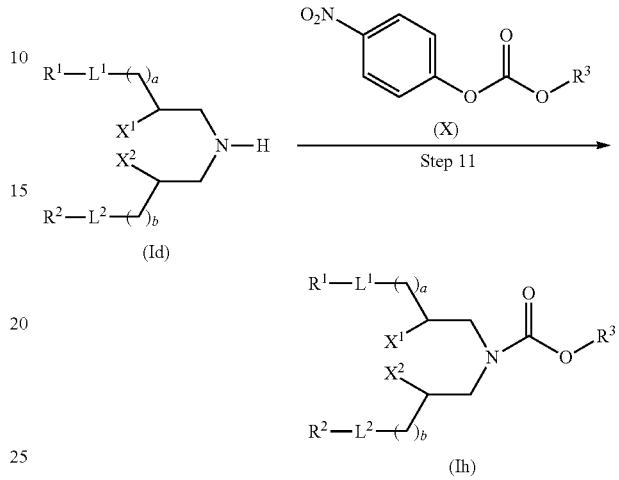

(In the formula, $R^1$, $R^2$, $R^3$, $L^1$, $L^2$, $X^1$, $X^2$, a and b have the same definitions as described above, respectively.)

Step 11

Compound (Ih) can be produced by reacting Compound (Id) with Compound (X) without solvent or in a solvent at a temperature between −20° C. and 150° C. for 5 minutes to 72 hours, in the presence of preferably 1 to 10 equivalents of an additive, and/or preferably 1 to 10 equivalents of a base, if necessary.

The same solvents and additives used in production method 2 may be used.

Examples of the base include triethylamine, diisopropylethylamine, N-methylmorpholine, pyridine, 1,8-diazabicyclo[5.4.0]-7-undecene, and the like.

Compound (X) can be obtained as a commercially available product or by known methods (for example, Journal of American Chemical Society (J. Am. Chem. Soc.), 1981, Vol. 103, p. 4194-4199), or a method in conformity thereof.

Production Method 9

Among the Compound (I), Compound (Ii) can be produced by the following method. In Compound (Ii), $L^3$ is a single bond, $R^3$ is —CH$_2$—C(OH)$R^C R^D$ ($R^C$ and $R^D$ are, the same or different, hydrogen atoms, alkyl having 1 to 4 carbon atoms, alkenyl having 3 to 4 carbon atoms, pyrrolidin-2-yl, pyrrolidin-3-yl, piperidin-2-yl, piperidin-3-yl, piperidin-4-yl, morpholin-2-yl, morpholin-3-yl, or alkyl having 1 to 4 carbon atoms or alkenyl having 3 to 4 carbon atoms substituted with 1 or 2 substituent(s), which is (are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl. The sum of the carbon atoms in the alkyl, the alkyl moiety of the substituted alkyl, alkenyl, and the alkenyl moiety of the substituted alkenyl in $R^C$ and $R^D$ is 1 to 4 except when $R^C$ and $R^D$ are both hydrogen atoms. When either of $R^C$ and $R^D$ is pyrrolidin-2-yl, pyrrolidin-3-yl, piperidin-2-yl, piperidin-3-yl, piperidin-4-yl, morpholin-2-yl or morpholin-3-yl, the other is a hydrogen atom, alkyl having 1 to 4 carbon atoms, alkenyl having 3 to 4 carbon atoms, pyrrolidin-2-yl, pyrrolidin-3-yl, piperidin-2-yl, piperidin-3- yl, piperidin-4-yl, morpholin-2-yl, morpholin-3-yl, or alkyl having 1 to 4 carbon atoms or alkenyl having 3 to 4 carbon atoms substituted with a substituent(s), which is (are) amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl. The total number of the substituents is 2 when $R^C$ and $R^D$ are substituted alkyl or substituted alkenyl), and $X^3$ and Y do not exist.

[Chemical Formula 11]

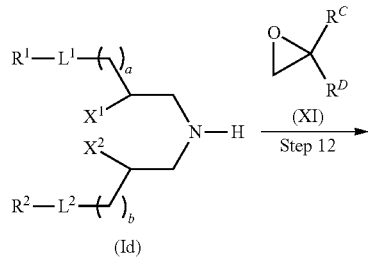
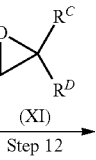

(Id)

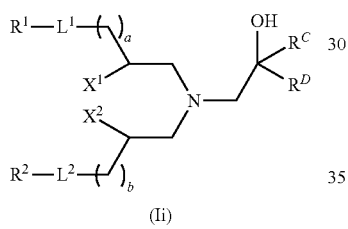

(Ii)

(In the formula, $R^1$, $R^2$, $R^C$, $R^D$, $L^1$, $L^2$, $X^1$, $X^2$, a and b have the same definitions as described above, respectively.)

Step 12

Compound (Ii) can be produced by treating Compound (Id) and Compound (XI) in the absence or presence of a solvent at a temperature between 0° C. and 230° C. for 5 minutes to 100 hours.

Examples of the solvent include methanol, ethanol, 1-propanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and dimethyl sulfoxide. These solvents are used solely or in admixture.

Compound (XI) can be obtained as a commercially available product or by a known method (for example, Dai 5-han, *Jikken Kagaku Kouza* (5th edition, Courses in Experimental Chemistry) 17, "Synthesis of Organic Compounds V", 5th edition, p. 186, Maruzen (2005)) or a method in conformity therewith.

Production Method 10

Among the Compound (I), Compound (Ij) in which $L^3$ is a single bond, $X^3$ is alkyl having 1 to 6 carbon atoms or alkenyl having 3 to 6 carbon atoms, and Y is a pharmaceutically acceptable anion can be produced by the following method.

[Chemical Formula 12]

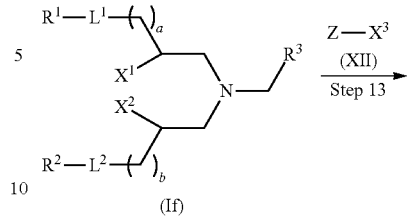

(If)

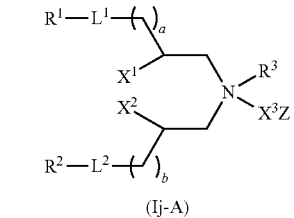

(Ij-A)

Step 14

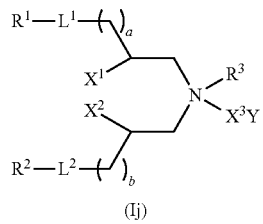

(Ij)

(In the formula, $R^1$, $R^2$, $R^3$, $L^1$, $L^2$, $X^1$, $X^2$, $X^3$, Y, a, b, and Z have the same definitions as described above, respectively.)

Steps 13 and 14

Compound (Ij-A) can be produced by treating Compound (If) and Compound (XII) in a solvent or without solvent at a temperature between 0° C. and 230° C. for 5 minutes to 100 hours. Compound (Ij) can be produced by treating Compound (Ij-A) with Y-type anion-exchange resin.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, and the like. These may be used either alone or as a mixture.

Compound (XII) can be obtained as a commercially available product or by known methods (for example, Dai 5-han, *Jikken Kagaku Kouza* (5th edition, Courses in Experimental Chemistry) 13, *Synthesis of Organic Compounds I*, 5th Ed., p. 374, Maruzen (2005)), or a method in conformity thereof.

When Z and Y are identical, Compound (Ij) may be produced by omitting step 14.

Production Method 11

Among the Compound (I), Compound (Id) in which $L^3$ is a single bond, $R^3$ is a hydrogen atom, and $X^3$ and Y are absent also can be produced by the following method.

[Chemical Formula 13]

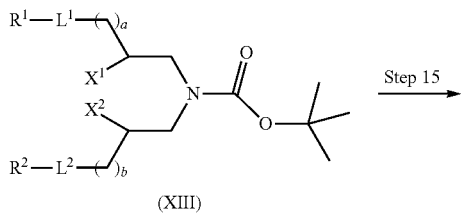

(XIII)

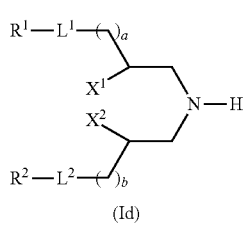

(Id)

(In the formula, $R^1$, $R^2$, $L^1$, $L^2$, $X^1$, $X^2$, a and b have the same definitions as described above, respectively.)

Step 15

Compound (Id) can be produced by reacting Compound (XIII) without solvent or in a solvent at a temperature between −20° C. and 150° C. for 5 minutes to 100 hours in the presence of preferably 1 to large excess amounts of an acid.

The same solvents used in production method 2 may be used.

Examples of the acid include trifluoroacetic acid, hydrochloric acid, and sulfuric acid.

Compound (XIII) can be obtained by using a modified method of production method 1, 2 or 3.

Conversion of the functional groups contained in $R^1$, $R^2$ or $R^3$ in Compound (I) can be performed by known methods [for example, methods described in Comprehensive Organic Transformations, 2nd edition, R. C. Larock, Vch Verlagsgesellschaft Mbh (1999), etc.], or a method in conformity thereof.

The intermediates and the target compounds in the foregoing production methods can be isolated and purified by using the common separation and purification techniques used in organic synthesis chemistry, including, for example, filtration, extraction, washing, drying, concentration, recrystallization, various chromatography techniques, and the like. The intermediates may be fed to the subsequent reactions without purification.

In the Compound (I), a hydrogen ion may coordinate to a lone pair on the nitrogen atom in the structure, and the nitrogen atom may form a salt together with a pharmaceutically acceptable anion (having the same definition as described above). The Compound (I) encompass compounds in which a hydrogen ion coordinates to a lone pair on the nitrogen atom. Note that, in the present invention, the absence of $X^3$ encompasses the case where a hydrogen ion is coordinated.

Compound (I) may exist as stereoisomers (such as geometrical isomers and optical isomers), tautomers, and the like. Compound (I) encompass all of possible isomers and mixtures thereof, inclusive of stereoisomers and tautomers.

A part of or all of the atoms in the Compound (I) may be replaced with corresponding isotope atoms. The Compound (I) encompass compounds in which a part of or all of the atoms thereof are replaced with such isotope atoms. For example, a part of or all of the hydrogen atoms in the Compound (I) may be hydrogen atoms having an atomic weight of 2 (deuterium atoms).

The compounds in which a part of or all of the atoms in the Compound (I) are replaced with corresponding isotope atoms can be produced by using methods similar to the foregoing production methods, using commercially available building blocks. Further, the compounds in which a part of or all of the hydrogen atoms in the Compound (I) are replaced with deuterium atoms can be synthesized by using various methods, including, for example, (1) a method in which a carboxylic acid or the like is deuterated using deuterium peroxide under a basic condition (see U.S. Pat. No. 3,849,458), (2) a method in which an alcohol, a carboxylic acid, or the like is deuterated using an iridium complex as a catalyst and using heavy water as a deuterium source (see J. Am. Chem. Soc., Vol. 124, No. 10, 2092 (2002)), (3) a method in which a fatty acid is deuterated using palladium-carbon as a catalyst and using only a deuterium gas as a deuterium source (see LIPIDS, Vol. 9, No. 11, 913 (1974)), (4) a method in which acrylic acid, methyl acrylate, methacrylic acid, methyl methacrylate, or the like is deuterated using a metal such as platinum, palladium, rhodium, ruthenium, and iridium as a catalyst and using heavy water or heavy water and a deuterium gas as a deuterium source (see Japanese Published Examined Patent Application No. 19536/1993, and Japanese Published Unexamined Patent Application No. 277648/1986 and No. 275241/1986), and (5) a method in which acrylic acid, methyl methacrylate, or the like is deuterated using a catalyst such as palladium, nickel, copper, and copper chromite and using heavy water as a deuterium source (see Japanese Published Unexamined Patent Application No. 198638/1988), and the like.

Specific examples of the Compound (I) obtained in the present invention are shown in Tables 1 to 17. It should be noted, however, that the compounds of the present invention are not limited to these.

TABLE 1

| Compound No. | Structure |
|---|---|
| 1 | ![structure] |

TABLE 1-continued
| Compound No. | Structure |
|---|---|
| 2 | 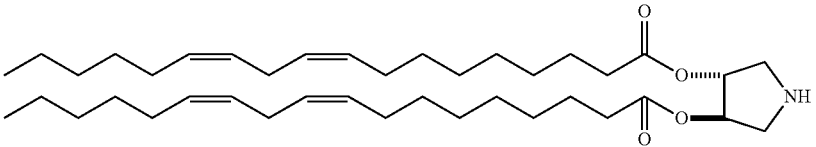 [SMILES: CCCCC/C=C\C/C=C\CCCCCCCC(=O)O[C@@H]1CNC[C@H]1OC(=O)CCCCCCC/C=C\C/C=C\CCCCC] |
| 3 | 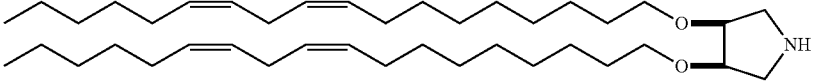 [SMILES: CCCCC/C=C\C/C=C\CCCCCCCCO[C@H]1CNC[C@H]1OCCCCCCCC/C=C\C/C=C\CCCCC] |
| 4 | 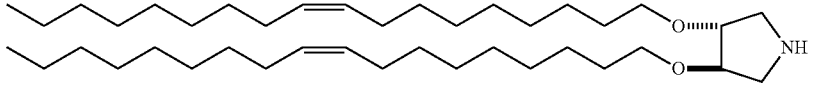 [SMILES: CCCCCCCC/C=C\CCCCCCCCO[C@@H]1CNC[C@H]1OCCCCCCCC/C=C\CCCCCCCC] |
| 5 | 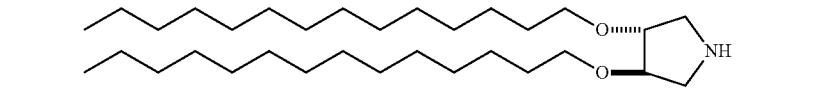 [SMILES: CCCCCCCCCCCCCCO[C@@H]1CNC[C@H]1OCCCCCCCCCCCCCC] |
| 6 | 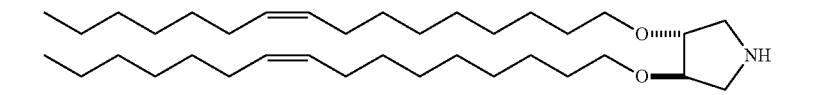 [SMILES: CCCCCC/C=C\CCCCCCCCO[C@@H]1CNC[C@H]1OCCCCCCCC/C=C\CCCCCC] |
| 7 | 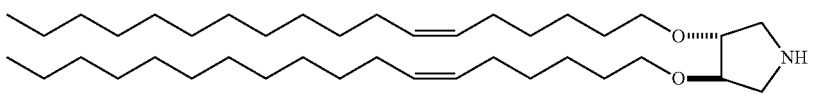 [SMILES: CCCCCCCCCCC/C=C\CCCCCO[C@@H]1CNC[C@H]1OCCCCC/C=C\CCCCCCCCCCC] |
| 8 | 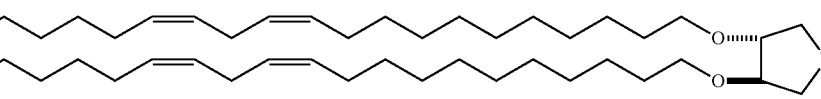 |
| 9 | 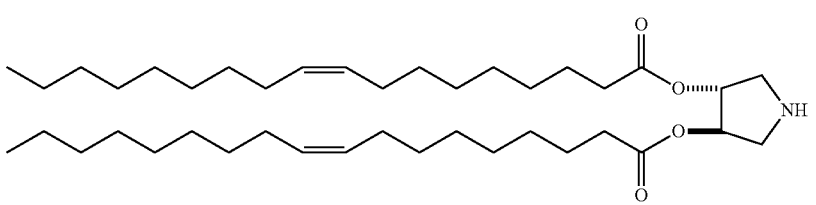 [SMILES: CCCCCCCC/C=C\CCCCCCCC(=O)O[C@@H]1CNC[C@H]1OC(=O)CCCCCCC/C=C\CCCCCCCC] |
| 10 | 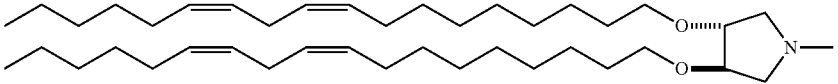 [SMILES: CCCCC/C=C\C/C=C\CCCCCCCCO[C@@H]1CN(C)C[C@H]1OCCCCCCCC/C=C\C/C=C\CCCCC] |
TABLE 2
| Compound No. | Structure |
|---|---|
| 11 | 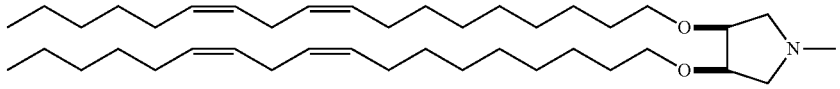 |
| 12 | 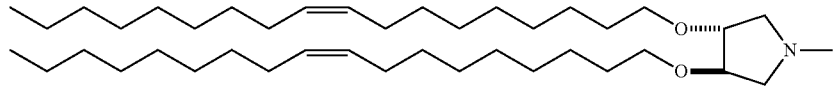 [SMILES: CCCCCCCC/C=C\CCCCCCCCO[C@@H]1CN(C)C[C@H]1OCCCCCCCC/C=C\CCCCCCCC] |
| 13 | 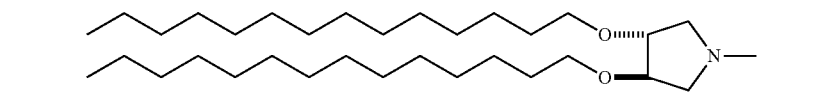 [SMILES: CCCCCCCCCCCCCCO[C@@H]1CN(C)C[C@H]1OCCCCCCCCCCCCCC] |

TABLE 2-continued

| Compound No. | Structure |
|---|---|
| 14 | (structure) |
| 15 | (structure) |
| 16 | (structure) |
| 17 | (structure) |
| 18 | (structure) |
| 19 | (structure) |
| 20 | (structure) |

TABLE 3

| Compound No. | Structure |
|---|---|
| 21 | (structure) |
| 22 | (structure) |
| 23 | (structure) |
| 24 | (structure) |

TABLE 3-continued

| Compound No. | Structure |
|---|---|
| 25 | (structure) |
| 26 | (structure) |
| 27 | (structure) |
| 28 | (structure) |

TABLE 4

| Compound No. | Structure |
|---|---|
| 29 | (structure) |
| 30 | (structure) |
| 31 | (structure) |
| 32 | (structure) |
| 33 | (structure) |

TABLE 4-continued
| Compound No. | Structure |
|---|---|
| 34 | 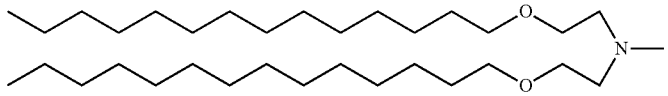 [SMILES: CCCCCCCCCCCCCCOCCN(C)CCOCCCCCCCCCCCCCC] |
| 35 | 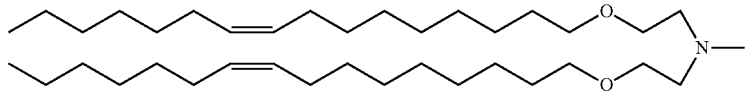 [SMILES: CCCCCC/C=C\CCCCCCCCOCCN(C)CCOCCCCCCCC/C=C\CCCCCC] |
| 36 | 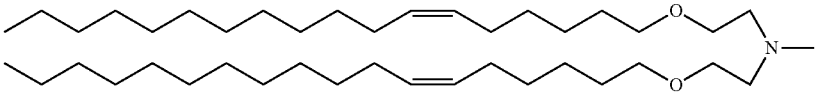 |
| 37 | 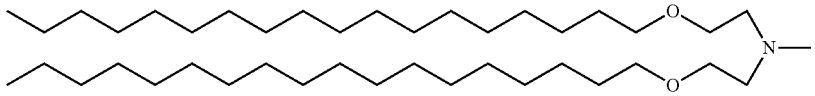 [SMILES: CCCCCCCCCCCCCCCCCCOCCN(C)CCOCCCCCCCCCCCCCCCCCC] |
TABLE 5
| Compound No. | Structure |
|---|---|
| 38 | 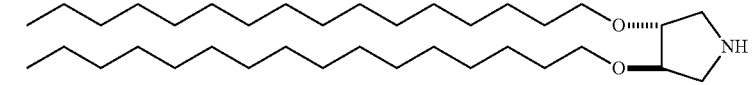 [SMILES: CCCCCCCCCCCCCCCCO[C@@H]1CNC[C@H]1OCCCCCCCCCCCCCCCC] |
| 39 | 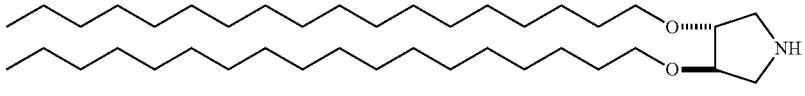 [SMILES: CCCCCCCCCCCCCCCCCCO[C@@H]1CNC[C@H]1OCCCCCCCCCCCCCCCCCC] |
| 40 | 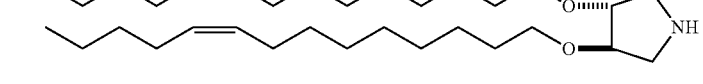 |
| 41 | 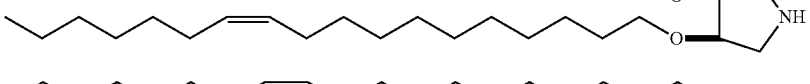 |
| 42 | 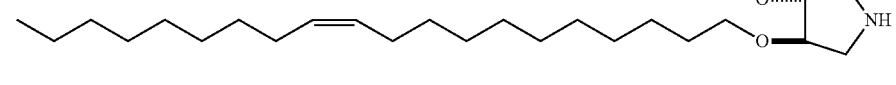 |
| 43 | 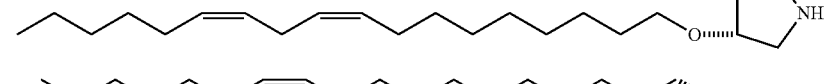 |
| 44 | 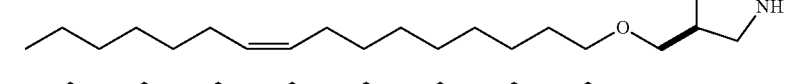 |
| 45 | 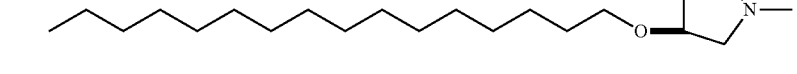 |
| 46 | 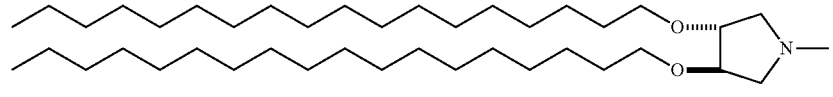 [SMILES: CCCCCCCCCCCCCCCCCCO[C@@H]1CN(C)C[C@H]1OCCCCCCCCCCCCCCCCCC] |

TABLE 5-continued

| Compound No. | Structure |
|---|---|
| 47 | (structure) |

TABLE 6

| Compound No. | Structure |
|---|---|
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |

TABLE 7

| Compound No. | Structure |
|---|---|
| 57 | 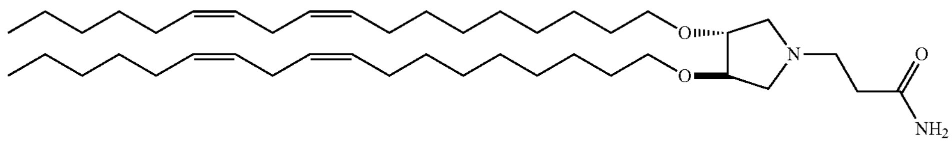 |
| 58 | 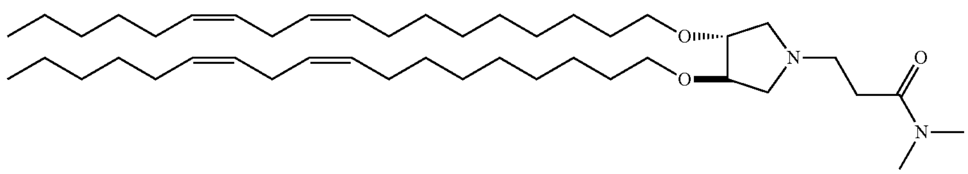 |
| 59 | 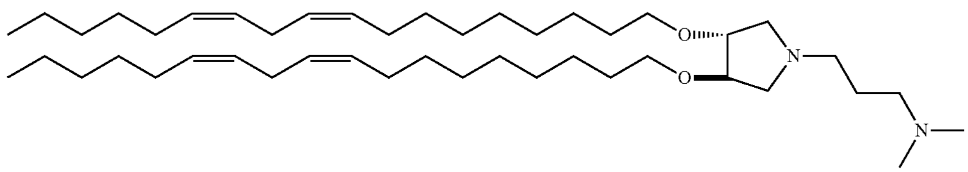 |
| 60 | 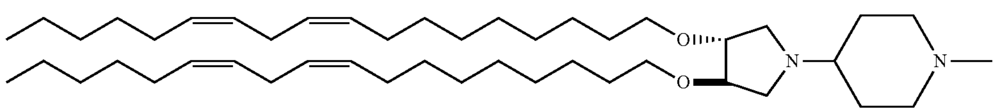 |
| 61 | 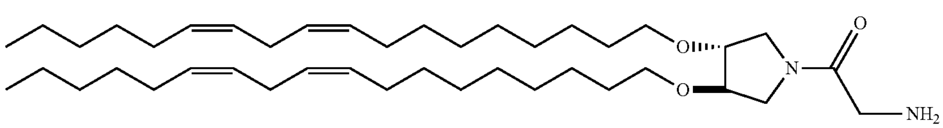 |
| 62 | 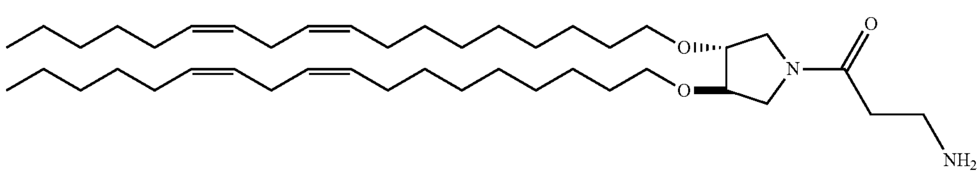 |
| 63 | 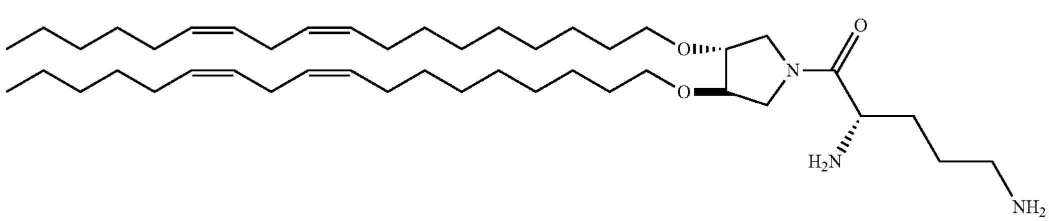 |
| 64 | 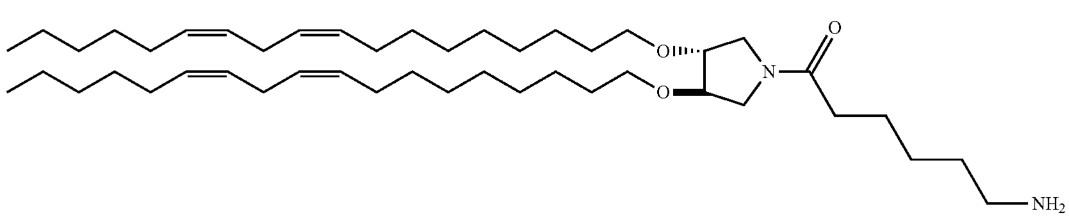 |

TABLE 8

| Compound No. | Structure |
|---|---|
| 65 | 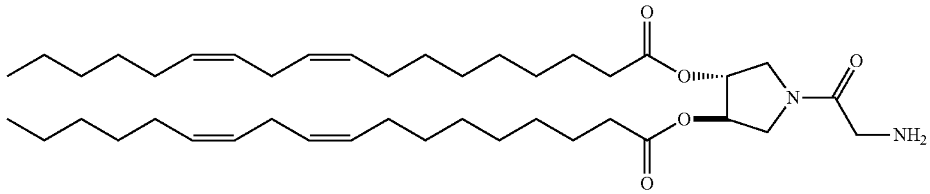 |
| 66 | 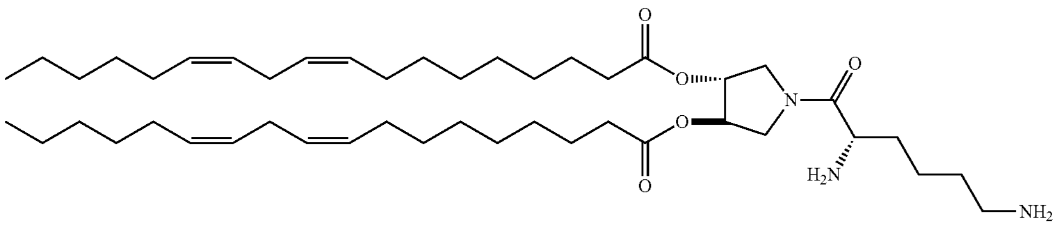 |
| 67 | 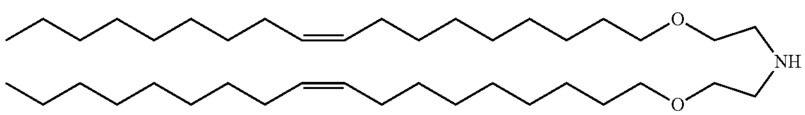 [SMILES: CCCCCCCC/C=C\CCCCCCCCOCCNCCOCCCCCCCC/C=C\CCCCCCCC] |
| 68 | 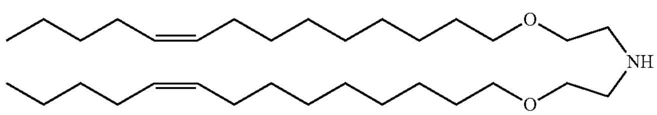 [SMILES: CCCC/C=C\CCCCCCCCOCCNCCOCCCCCCCC/C=C\CCCC] |
| 69 | 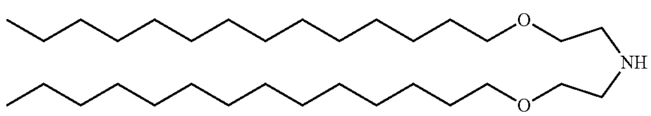 [SMILES: CCCCCCCCCCCCCCOCCNCCOCCCCCCCCCCCCCC] |
| 70 | 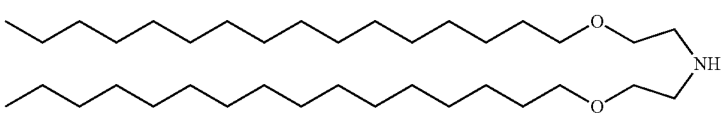 [SMILES: CCCCCCCCCCCCCCCCOCCNCCOCCCCCCCCCCCCCCCC] |
| 71 | 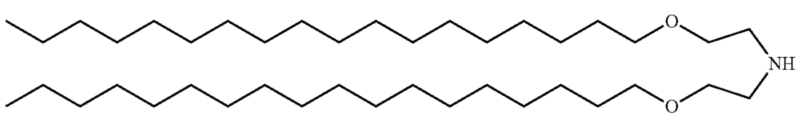 [SMILES: CCCCCCCCCCCCCCCCCCOCCNCCOCCCCCCCCCCCCCCCCCC] |
| 72 | 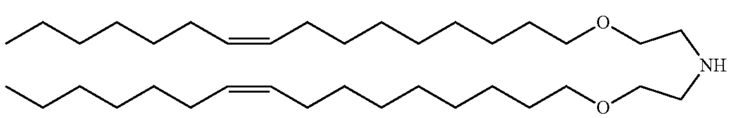 [SMILES: CCCCCC/C=C\CCCCCCCCOCCNCCOCCCCCCCC/C=C\CCCCCC] |

TABLE 9

| Compound No. | Structure |
|---|---|
| 73 | 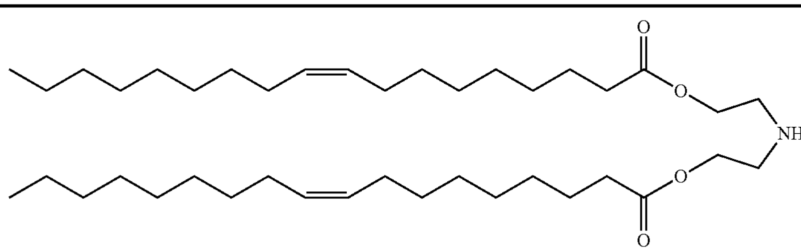 |

TABLE 9-continued

| Compound No. | Structure |
|---|---|
| 74 | (structure) |
| 75 | (structure) |
| 76 | (structure) |
| 77 | (structure) |
| 78 | (structure) |
| 79 | (structure) |
| 80 | (structure) |

TABLE 10

| Compound No. | Structure |
|---|---|
| 81 | (structure) |
| 82 | (structure) |

TABLE 10-continued
| Compound No. | Structure |
|---|---|
| 83 | 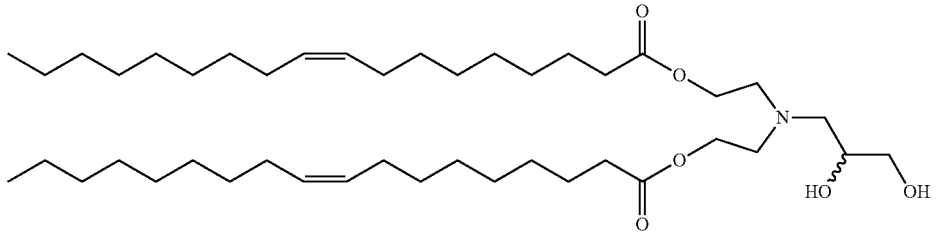 [SMILES: CCCCCCCC/C=C\CCCCCCCC(=O)OCCN(CCOC(=O)CCCCCCC/C=C\CCCCCCCC)CC(O)CO] |
| 84 | 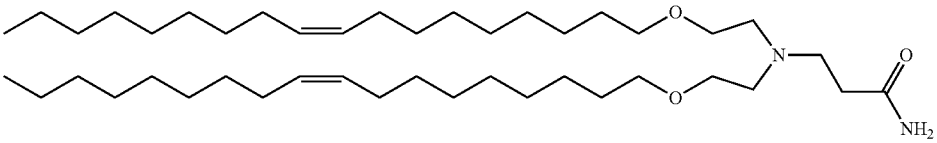 [SMILES: CCCCCCCC/C=C\CCCCCCCCOCCN(CCOCCCCCCCC/C=C\CCCCCCCC)CCC(N)=O] |
| 85 | 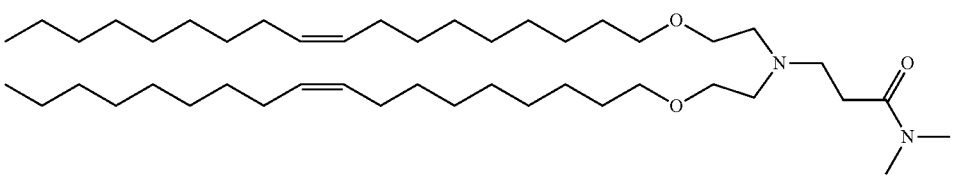 [SMILES: CCCCCCCC/C=C\CCCCCCCCOCCN(CCOCCCCCCCC/C=C\CCCCCCCC)CCC(=O)N(C)C] |
| 86 | 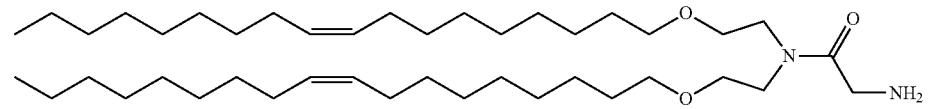 [SMILES: CCCCCCCC/C=C\CCCCCCCCOCCN(CCOCCCCCCCC/C=C\CCCCCCCC)C(=O)CN] |
| 87 | 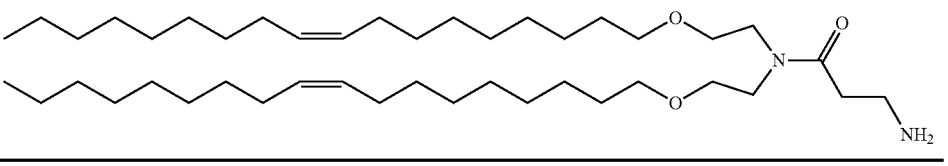 |
TABLE 11
| Compound No | Structure |
|---|---|
| 88 | 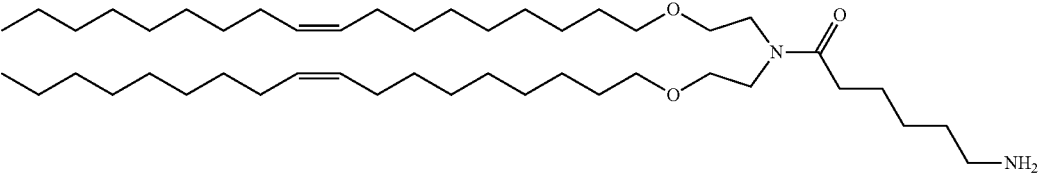 [SMILES: CCCCCCCC/C=C\CCCCCCCCOCCN(CCOCCCCCCCC/C=C\CCCCCCCC)C(=O)CCCCCN] |
| 89 | 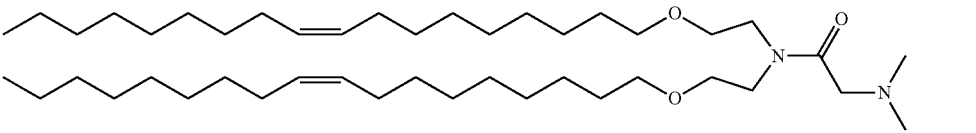 [SMILES: CCCCCCCC/C=C\CCCCCCCCOCCN(CCOCCCCCCCC/C=C\CCCCCCCC)C(=O)CN(C)C] |
| 90 | 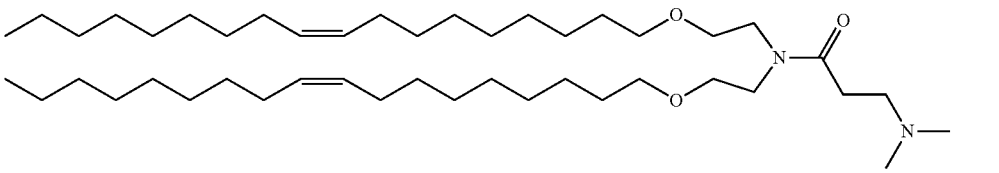 [SMILES: CCCCCCCC/C=C\CCCCCCCCOCCN(CCOCCCCCCCC/C=C\CCCCCCCC)C(=O)CCN(C)C] |

TABLE 11-continued

| Compound No | Structure |
|---|---|
| 91 | 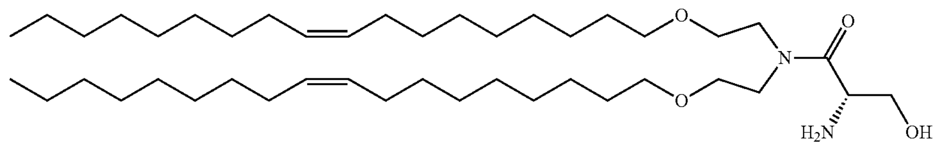 [SMILES: CCCCCCCC/C=C\CCCCCCCCOCCN(CCOCCCCCCCC/C=C\CCCCCCCC)C(=O)[C@@H](N)CO] |
| 92 | 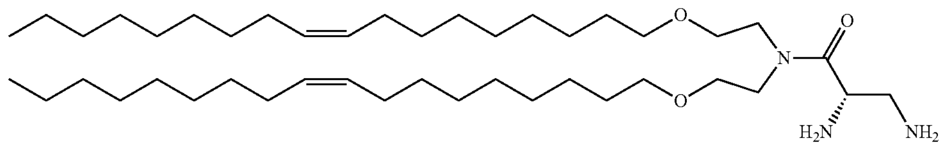 [SMILES: CCCCCCCC/C=C\CCCCCCCCOCCN(CCOCCCCCCCC/C=C\CCCCCCCC)C(=O)[C@@H](N)CN] |
| 93 | 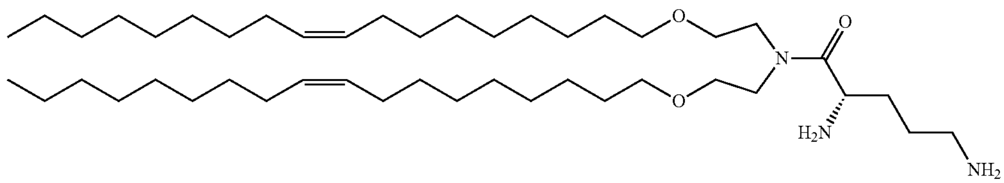 [SMILES: CCCCCCCC/C=C\CCCCCCCCOCCN(CCOCCCCCCCC/C=C\CCCCCCCC)C(=O)[C@@H](N)CCCN] |
| 94 | 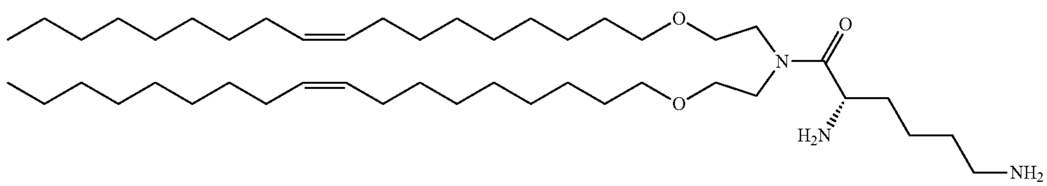 [SMILES: CCCCCCCC/C=C\CCCCCCCCOCCN(CCOCCCCCCCC/C=C\CCCCCCCC)C(=O)[C@@H](N)CCCCN] |

TABLE 12

| Compound No. | Structure |
|---|---|
| 95 | 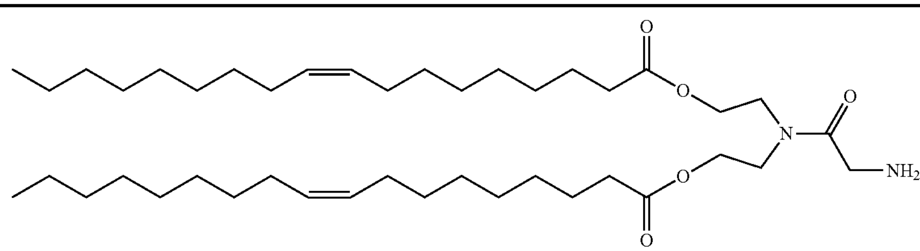 |
| 96 | 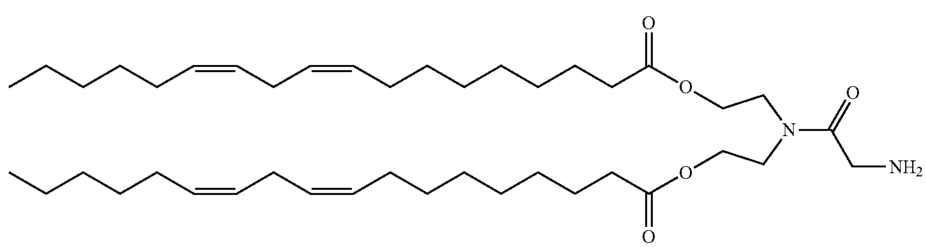 [SMILES: CCCCC/C=C\C/C=C\CCCCCCCC(=O)OCCN(CCOC(=O)CCCCCCC/C=C\C/C=C\CCCCC)C(=O)CN] |
| 97 | 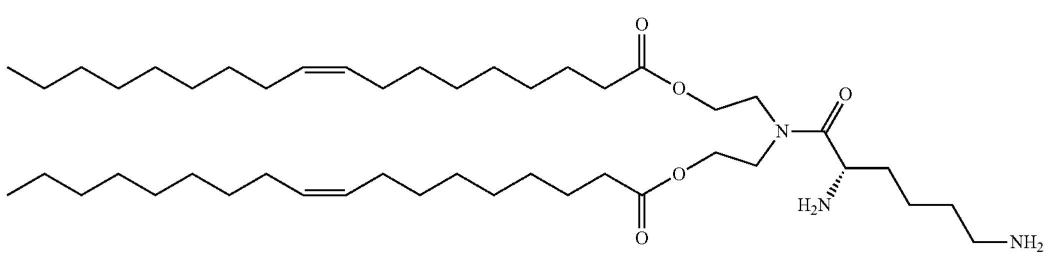 [SMILES: CCCCCCCC/C=C\CCCCCCCC(=O)OCCN(CCOC(=O)CCCCCCC/C=C\CCCCCCCC)C(=O)[C@@H](N)CCCCN] |

TABLE 12-continued

| Compound No. | Structure |
|---|---|
| 98 | 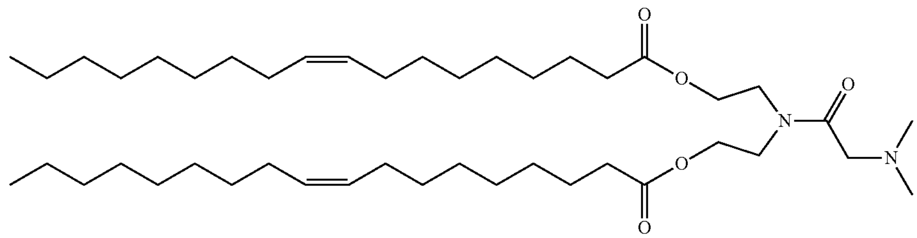 [SMILES: CCCCCCCC/C=C\CCCCCCCC(=O)OCCN(CCOC(=O)CCCCCCC/C=C\CCCCCCCC)C(=O)CN(C)C] |
| 99 | 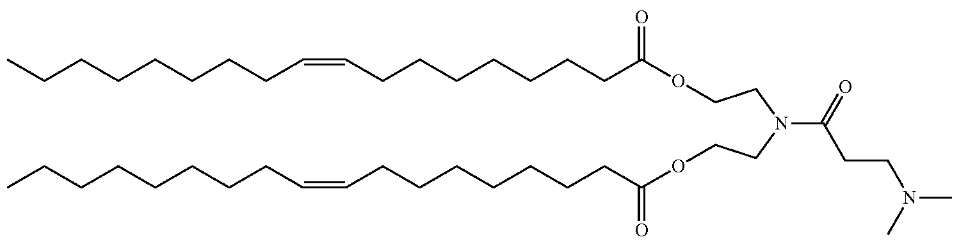 [SMILES: CCCCCCCC/C=C\CCCCCCCC(=O)OCCN(CCOC(=O)CCCCCCC/C=C\CCCCCCCC)C(=O)CCN(C)C] |
| 100 | 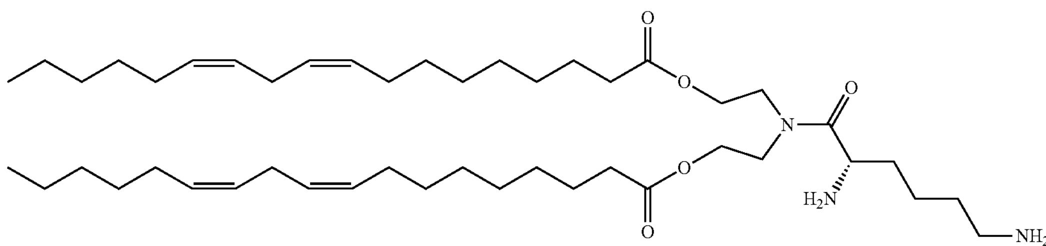 [SMILES: CCCCC/C=C\C/C=C\CCCCCCCC(=O)OCCN(CCOC(=O)CCCCCCC/C=C\C/C=C\CCCCC)C(=O)[C@@H](N)CCCCN] |

TABLE 13

| Compound No. | Structure |
|---|---|
| 101 | 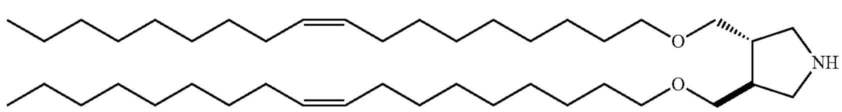 |
| 102 | 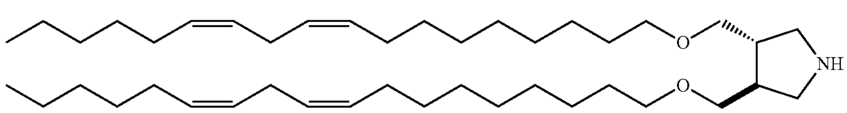 |
| 103 | 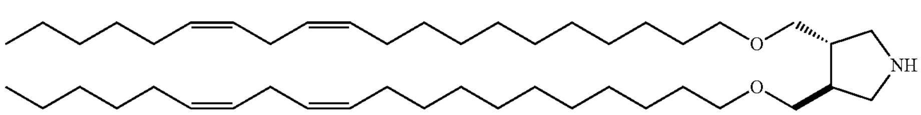 |
| 104 | 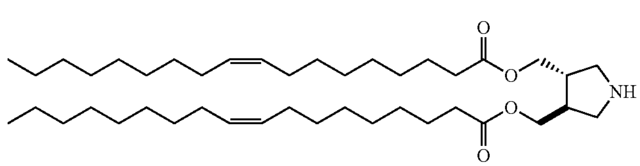 |

TABLE 13-continued

| Compound No. | Structure |
|---|---|
| 105 | (structure: dilinoleoyl diester of 3,4-bis(hydroxymethyl)pyrrolidine, NH) |
| 106 | (structure: dioleyl diether of 3,4-bis(hydroxymethyl)-N-methylpyrrolidine) |
| 107 | (structure: dilinoleyl diether of 3,4-bis(hydroxymethyl)-N-methylpyrrolidine) |
| 108 | (structure: dilinoleyl diether with longer linker of N-methylpyrrolidine) |
| 109 | (structure: dioleoyl diester of 3,4-bis(hydroxymethyl)-N-methylpyrrolidine) |

TABLE 14

| Compound No. | Structure |
|---|---|
| 110 | (structure: dilinoleoyl diester of 3,4-bis(hydroxymethyl)-N-methylpyrrolidine) |
| 111 | (structure: dioleyl diether of N,N-dimethylpyrrolidinium, Cl⁻) |
| 112 | (structure: dilinoleyl diether of N,N-dimethylpyrrolidinium, Cl⁻) |
| 113 | (structure: dioleoyl diester of N,N-dimethylpyrrolidinium, Cl⁻) |

TABLE 14-continued
| Compound No. | Structure |
|---|---|
| 114 | 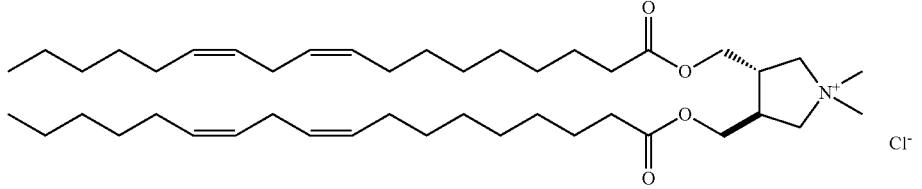 |
| 115 | 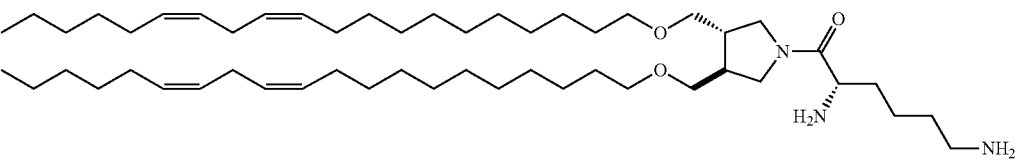 |
| 116 | 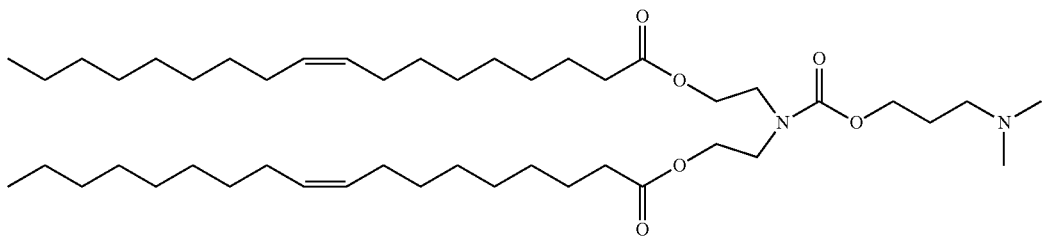 [SMILES: CCCCCCCC/C=C\CCCCCCCC(=O)OCCN(CCOC(=O)CCCCCCC/C=C\CCCCCCCC)C(=O)OCCCN(C)C] |
TABLE 15
| Compound No. | Structure |
|---|---|
| 117 | 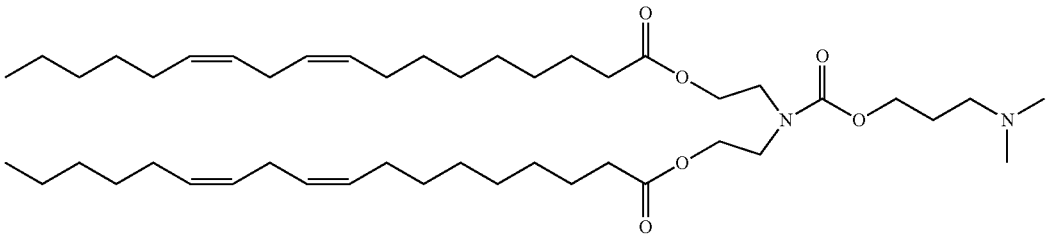 [SMILES: CCCCC/C=C\C/C=C\CCCCCCCC(=O)OCCN(CCOC(=O)CCCCCCC/C=C\C/C=C\CCCCC)C(=O)OCCCN(C)C] |
| 118 | 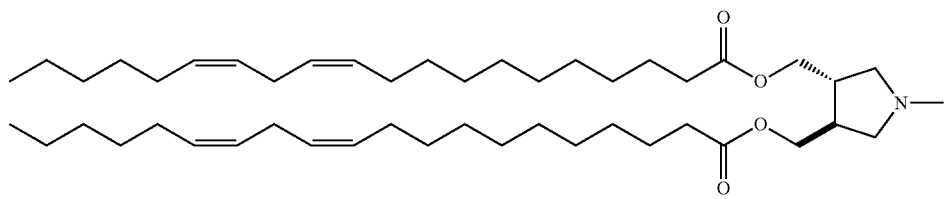 |
| 119 | 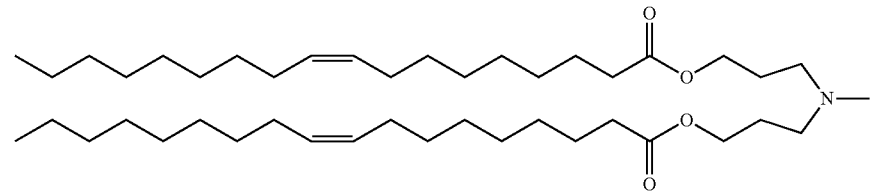 [SMILES: CCCCCCCC/C=C\CCCCCCCC(=O)OCCCN(C)CCCOC(=O)CCCCCCC/C=C\CCCCCCCC] |

TABLE 15-continued

| Compound No. | Structure |
|---|---|
| 120 | 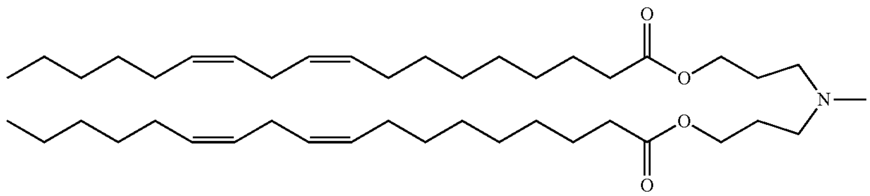 [SMILES: CCCCC/C=C\C/C=C\CCCCCCCC(=O)OCCCN(C)CCCOC(=O)CCCCCCC/C=C\C/C=C\CCCCC] |
| 121 | 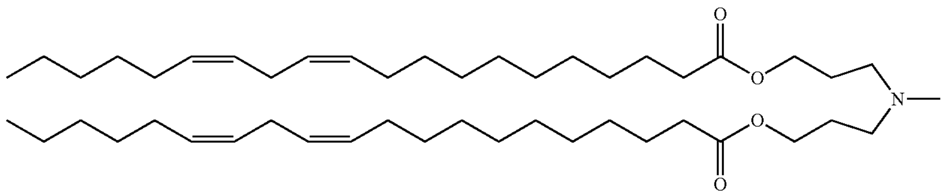 [SMILES: CCCCC/C=C\C/C=C\CCCCCCCCCC(=O)OCCCN(C)CCCOC(=O)CCCCCCCCC/C=C\C/C=C\CCCCC] |
| 122 | 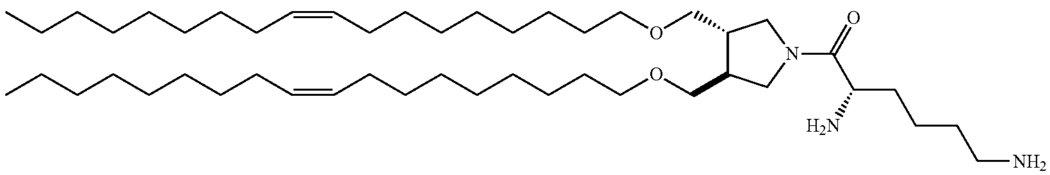 |

TABLE 16

| Compound No. | Structure |
|---|---|
| 123 | 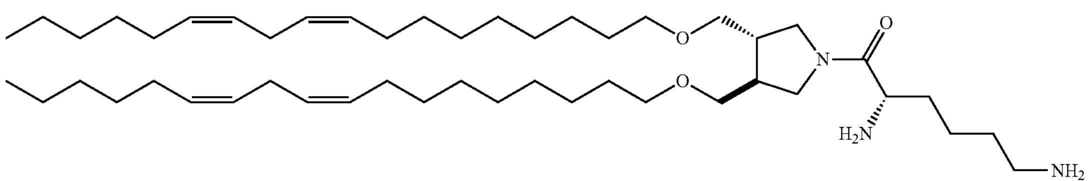 |
| 124 | 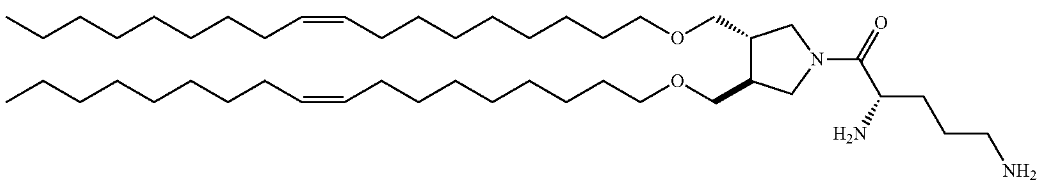 |
| 125 | 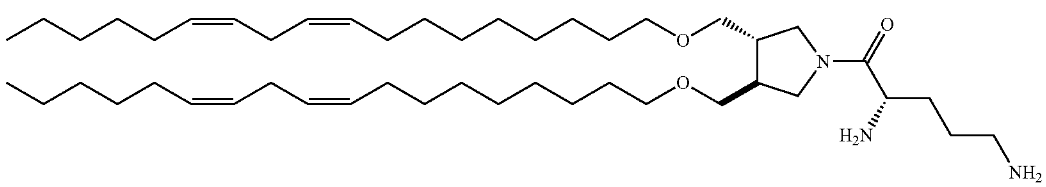 |
| 126 | 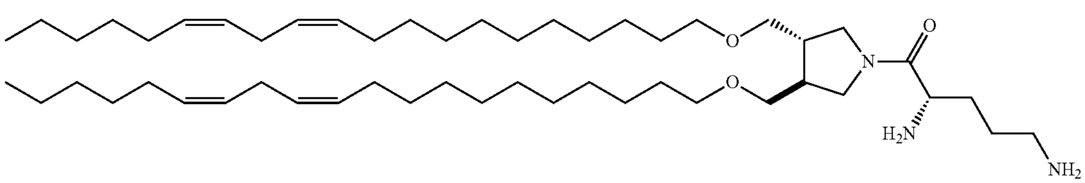 |

TABLE 16-continued

| Compound No. | Structure |
|---|---|
| 127 | 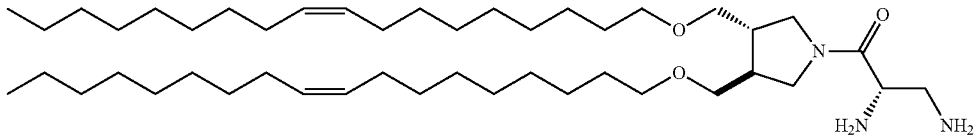 |
| 128 | 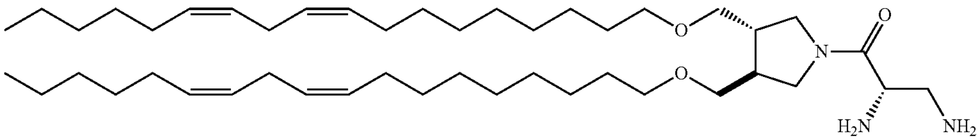 |
| 129 | 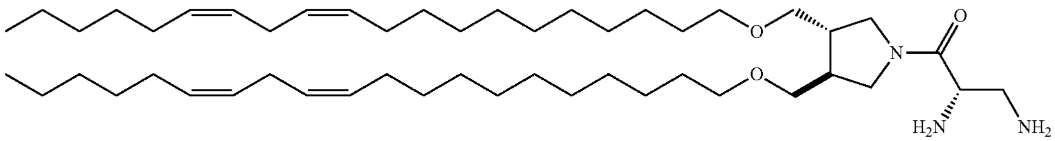 |

TABLE 17

| Compound No. | Structure |
|---|---|
| 130 | 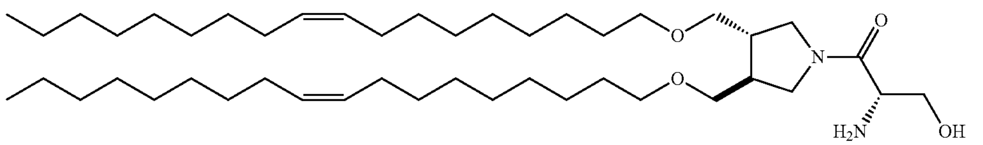 |
| 131 | 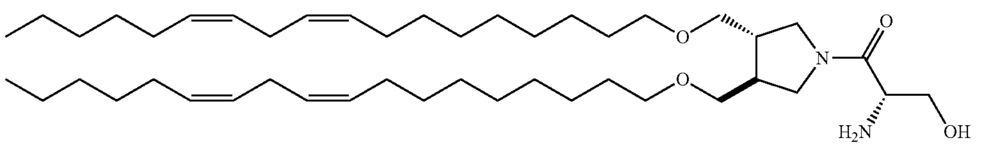 |
| 132 | 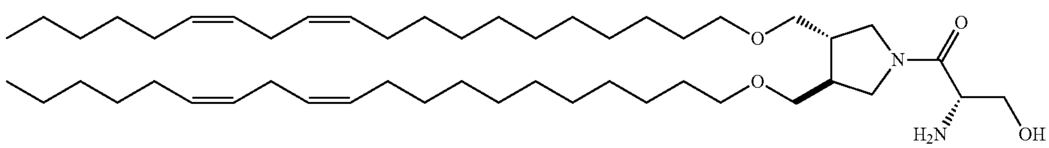 |
| 133 | 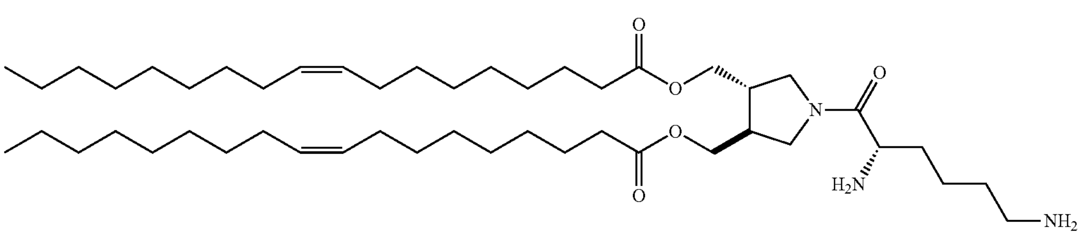 |
| 134 | 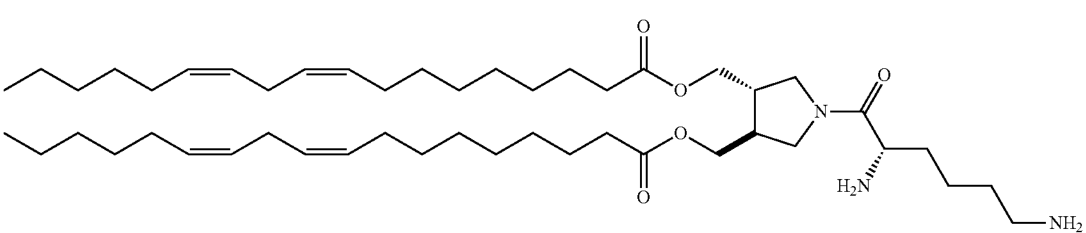 |

TABLE 17-continued

| Compound No. | Structure |
|---|---|
| 135 | 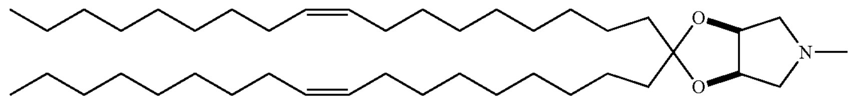 |
| 136 | 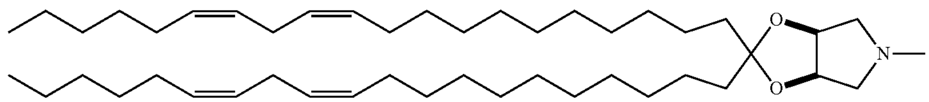 |

The nucleic acid which is used in the present invention may be any molecule so far as it is a molecule obtained through polymerization of nucleotide and/or a molecule having an equal function to the nucleotide. Examples thereof include RNA that is a polymer of ribonucleotide; DNA that is a polymer of deoxyribonucleotide; a chimera nucleic acid composed of RNA and DNA; and a nucleotide polymer in which at least one nucleotide of these nucleic acids is substituted with a molecule having an equal function to the nucleotide. In addition, a derivative containing at least one polymerized molecule of nucleotide and/or a molecule having an equal function to the nucleotide is also included in the nucleic acid of the present invention. Incidentally, in the present invention, uridine U in RNA and thymine T in DNA shall be deemed to be replaced with each other.

Examples of the molecule having an equal function to nucleotide include nucleotide derivatives.

The nucleotide derivative may be any molecule so far as it is a molecule obtained by applying modification to nucleotide. For example, for the purpose of enhancing the nuclease resistance or achieving stabilization from other decomposing factor as compared with RNA or DNA, increasing the affinity with the complementary strand nucleic acid, increasing the cellular permeability, or achieving the visualization, molecules obtained by applying modification to ribonucleotide or deoxyribonucleotide are suitably used.

Examples of the nucleotide derivative include a sugar moiety modified nucleotide, a phosphodiester bond modified nucleotide, and a base modified nucleotide.

The sugar moiety modified nucleotide may be any nucleotide in which a part or the entirety of the chemical structure of the sugar moiety of nucleotide is modified or substituted with an arbitrary substituent, or substituted with an arbitrary atom. Above all, a 2'-modified nucleotide is preferably used.

Examples of the modifying group in the sugar moiety modified nucleotide include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, —SiH$_2$-substituted alkyl, 2'-ONO$_2$, 2'-NO$_2$, 2'-N$_3$, 2'-amino acid residue (the residue that the hydroxyl group is removed from the carboxylic acid of amino acid), and 2'-O-amino acid residue (having the same definition as above), and the like. In addition, Examples thereof include a peptide nucleic acid (PNA) [Acc. Chem. Res., 32, 624 (1999)], an oxy-peptide nucleic acid (OPNA) [J. Am. Chem. Soc., 123, 4653 (2001)], a peptide ribonucleic acid (PRNA) [J. Am. Chem. Soc., 122, 6900 (2000)]. The ribose with the substitution by a modifying group at 2' position in the present invention also encompasses bridged nucleic acids (BNAs) of a structure in which the modifying group at 2' position is bridged to the 4' carbon atom, specifically, locked nucleic acids (LNAs) in which the oxygen atom at 2' position is bridged to the 4' carbon atom via methylene, ethylene bridged nucleic acids (ENAs) [Nucleic Acid Research, 32, e175 (2004)], and the like.

The preferred modifying group in the sugar moiety modified nucleotide include 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, and 2'-Se-substituted alkyl. More preferred examples include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-(2-[N,N-dimethyl]aminooxy)ethyl, 2'-O-[3-(N,N-dimethylamino)propyl], 2'-O-[2-[2-(N,N-Dimethylamino) ethoxy]ethyl], 2'-O-[2-(methylamino)-2-oxoethyl], 2'-Se-methyl, and the like. Even more preferred are 2'-O-methyl, 2'-O-ethyl, 2'-fluoro, and the like. 2'-O-methyl and 2'-O-ethyl are most preferable.

The preferred range of the modifying group in the sugar moiety modified nucleotide may be defined based on its size. Modifying groups of a size corresponding to the size of fluoro to the size of —O-butyl are preferable, and modifying groups of a size corresponding to the size of —O-methyl to the size of —O-ethyl are more preferable.

The alkyl in the modifying group of the sugar moiety modified nucleotide is the same as the above-mentioned definition of the alkyl having a carbon number of 1 to 6 in the cationic lipid of the present invention.

The alkenyl in the modifying group of the sugar moiety modified nucleotide is the same as the above-mentioned definition of the alkenyl having a carbon number of 3 to 6 in the cationic lipid of the present invention.

Examples of the halogen in the modifying group of the sugar moiety modified nucleotide include a fluorine atom, a chlorine atom, a bromine atom, and an iodine atom.

Examples of the amino acid in amino acid residue include aliphatic amino acids (specifically, glycine, alanine, valine, leucine, isoleucine, and the like), hydroxy amino acids (specifically, serine, threonine, and the like), acidic amino acids (specifically, aspartic acid, glutamic acid, and the like), acidic amino acid amides (specifically, asparagine, glutamine, and the like), basic amino acids (specifically, lysine, hydroxylysine, arginine, ornithine, and the like), sulfur-containing amino acids (specifically, cysteine, cystine, methionine, and the like), imino acids (specifically, proline, 4-hydroxy proline, and the like), and the like.

Examples of the substituents of the substituted alkyl and the substituted alkenyl in the sugar moiety modified nucleotide include halogen (having the same definition as above), hydroxy, sulfanyl, amino, oxo, —O-alkyl (the alkyl moiety of —O-alkyl has the same definition as above), —S-alkyl (the alkyl moiety of —S-alkyl has the same definition as above), —NH-alkyl (the alkyl moiety of —NH-alkyl has the same definition as above), dialkylaminooxy (the two alkyls of the dialkylaminooxy may be the same or different, and have the same definition as above), dialkylamino (the two alkyls of the dialkylamino may be the same or different, and have the same definition as above), dialkylaminoalkyleneoxy (the two alkyls of the dialkylaminoalkyleneoxy may be the same or different, and have the same definition as above; the alkylene means a group wherein the one hydrogen atom is removed from above-defined alkyl), and the like, and number of substituent is preferably 1 to 3.

The phosphodiester bond modified nucleotide may be any nucleotide in which a part or the entirety of the chemical structure of the phosphodiester bond of nucleotide is modified or substituted with an arbitrary substituent, or substituted with an arbitrary atom. Examples thereof include a nucleotide in which the phosphodiester bond is substituted with a phosphorothioate bond, a nucleotide in which the phosphodiester bond is substituted with a phosphorodithioate bond, a nucleotide in which the phosphodiester bond is substituted with an alkylphosphonate bond, and a nucleotide in which the phosphodiester bond is substituted with a phosphoroamidate bond.

The base-modified nucleotide may be any nucleotide in which a part or the entirety of the chemical structure of the base of nucleotide is modified or substituted with an arbitrary substituent, or substituted with an arbitrary atom. Examples thereof include a nucleotide in which an oxygen atom in the base is substituted with a sulfur atom, a nucleotide in which a hydrogen atom is substituted with an alkyl group having a carbon number of 1 to 6, a nucleotide in which a methyl group is substituted with a hydrogen atom or an alkyl group having a carbon number of 2 to 6, and a nucleotide in which an amino group is protected by a protective group such as an alkyl group having a carbon number of 1 to 6 and an alkanoyl group having a carbon number of 1 to 6.

Furthermore, examples of the nucleotide derivative include those in which other chemical substance such as a lipid, phospholipid, phenazine, folate, phenanthridine, anthraquinone, acridine, fluorescein, rhodamine, coumarin, and a pigment is added to nucleotide or a nucleotide derivative in which at least one of the sugar moiety, the phosphodiester bond, and the base is modified. Specific examples thereof include 5'-polyamine added nucleotide derivatives, cholesterol added nucleotide derivatives, steroid added nucleotide derivatives, bile acid added nucleotide derivatives, vitamin added nucleotide derivatives, Cy5 added nucleotide derivatives, Cy3 added nucleotide derivatives, 6-FAM added nucleotide derivatives, and biotin added nucleotide derivatives.

In addition, the nucleotide derivatives may form, together with other nucleotides or nucleotide derivatives within the nucleic acid, a crosslinked structure such as an alkylene structure, a peptide structure, a nucleotide structure, an ether structure, and an ester structure, or a structure combined with at least one of these structures.

Examples of the nucleic acids used in the present invention include preferably nucleic acids that suppress the expression of the target gene, more preferably nucleic acids that have an activity of suppressing the expression of the target gene by utilizing RNA interference (RNAi).

The target gene used in the present invention is not particularly limited, as long as it is expressed through mRNA production. Preferred examples thereof include genes associated with tumor or inflammation, including, for example, genes that encodes proteins such as vascular endothelial growth factors (hereinafter, "VEGF"), vascular endothelial growth factor receptors (hereinafter, "VEGFR"), fibroblast growth factors, fibroblast growth factor receptors, platelet-derived growth factors, platelet-derived growth factor receptors, liver cell growth factors, liver cell growth factor receptors, Kruppel-like factors (hereinafter, "KLF"), Ets transcription factors, nuclear factors, and hypoxia-inducible factors. Specific examples thereof include VEGF genes, VEGFR genes, fibroblast growth factor genes, fibroblast growth factor receptor genes, platelet-derived growth factor genes, platelet-derived growth factor receptor genes, liver cell growth factor genes, liver cell growth factor receptor genes, KLF genes, Ets transcription factor genes, nuclear factor genes, hypoxia-inducible factor genes, and the like.

Preferably, the target gene used in the present invention is a gene that is expressed, for example, in liver, lungs, kidneys or spleen. Examples thereof include genes associated with tumor or inflammation (such as above), hepatitis B virus genome, hepatitis C virus genome, and genes that encode proteins such as apolipoprotein (APO), hydroxymethyl glutaryl (HMG) CoA reductase, kexin type 9 serine protease (PCSK9), factor XII, glucagon receptor, glucocorticoid receptor, leukotriene receptor, thromboxane A2 receptor, histamine H1 receptor, carbonic anhydrase, angiotensin converting enzyme, renin, p53, tyrosine phosphatase (PTP), sodium dependent glucose transporter, tumor necrosis factor, and interleukin, and the like.

The nucleic acid that suppresses the expression of the target gene may be any of, for example, double-stranded nucleic acids (such as siRNA (short interference RNA), and miRNA (micro RNA)), single-stranded nucleic acid (shRNA (short hairpin RNA), antisense nucleic acids, ribozyme, etc), and the like, provided that, for example, the nucleic acid contains abase sequence complementary to apart of the base sequence of the mRNA of the gene (target gene) encoding a protein and the like, and that the nucleic acid suppresses the expression of the target gene. Double-stranded nucleic acids are preferably used.

The nucleic acids that contain a base sequence complementary to a part of the base sequence of the target gene mRNA are also referred to as antisense strand nucleic acids, and the nucleic acids that contain a base sequence complementary to the base sequence of the antisense strand nucleic acid are also referred to as sense strand nucleic acids. The sense strand nucleic acids are nucleic acids that can form a double strand by pairing with antisense strand nucleic acids, including the nucleic acid itself that has a partial base sequence of the target gene.

The double-stranded nucleic acids are nucleic acids that have two strands forming a double-stranded portion by pairing. The double-stranded portion is a portion where a double strand is formed by the base pairing of the nucleotides or derivatives thereof forming a double-stranded nucleic acid. The base pairs forming the double-stranded portion are typically 15 to 27 bps, preferably 15 to 25 bps, more preferably 15 to 23 bps, further preferably 15 to 21 bps, particularly preferably 15 to 19 bps.

Preferred for use as the antisense strand nucleic acid of the double-stranded portion are nucleic acids that contain a partial sequence of the target gene mRNA, with or without the substitution, deletion, or addition of 1 to 3 bases, preferably 1 to 2 bases, more preferably 1 base, and that have a target protein expression suppressing activity. The length of the single-stranded nucleic acid forming a double-stranded nucleic acid is typically 15 to 30 bases, preferably 15 to 29 bases, more preferably 15 to 27 bases, further preferably 15 to 25 bases, particularly preferably 17 to 23 bases, most preferably 19 to 21 bases.

The nucleic acid in the antisense strand and/or the sense strand forming a double-stranded nucleic acid may have an additional nucleic acid that does not form a double strand, contiguous from the 3'-end or 5'-end of the double-stranded portion. Such portions not forming a double strand are also referred to as an extension (overhang).

The extension in such double-stranded nucleic acids has 1 to 4 bases, typically 1 to 3 bases at the 3'-end or 5'-end of at least one of the strands. Preferably, the extension has 2 bases, more preferably dTdT or UU. The extension may be present on only one of the antisense strand and the sense strand, or on both of the antisense strand and the sense strand. However, double-stranded nucleic acids having extensions on both the antisense strand and the sense strand are preferably used.

It is also possible to use a sequence contiguous from the double-stranded portion and partially or completely matches the target gene mRNA, or a sequence contiguous from the double-stranded portion and matches the base sequence of the complementary strand of the target gene mRNA. Further, the nucleic acid that suppresses the expression of the target gene may be, for example, a nucleic acid molecule that generates a double-stranded nucleic acid by the activity of a ribonuclease such as Dicer (WO2005/089287), or a double-stranded nucleic acid that does not have a 3' or 5' extension.

When the double-stranded nucleic acid is siRNA, the antisense strand has a base sequence in which at least bases 1 to 17 from the 5'-end to the 3'-end are complementary to 17 contiguous bases of the target gene mRNA. Preferably, the antisense strand has a base sequence in which bases 1 to 19 from the 5'-end to the 3'-end are complementary to 19 contiguous bases of the target gene mRNA, a base sequence in which bases 1 to 21 are complementary to 21 contiguous bases of the target gene mRNA, or abase sequence in which bases 1 to 25 are complementary to 25 contiguous bases of the target gene mRNA.

Further, when the nucleic acid used in the present invention is siRNA, preferably 10 to 70%, more preferably 15 to 60%, further preferably 20 to 50% of the sugars in the nucleic acid are riboses substituted with a modifying group at the 2'-position. In the present invention, the substitution of the ribose with a modifying group at the 2'-position means the substitution of the hydroxyl group with a modifying group at the 2'-position. The configuration may be the same as or different from the configuration of the ribose hydroxyl group at the 2'-position. Preferably, the configuration is the same as the configuration of the ribose hydroxyl group at the 2'-position. The ribose substituted with a modifying group at the 2'-position is included within a 2'-modified nucleotide from among sugar-modified nucleotides, and the modifying group of the ribose substituted at the 2'-position has the same definition as the modifying group of 2'-modified nucleotides.

The nucleic acid used in the present invention includes derivatives in which the oxygen atom or the like contained in the phosphate moiety, the ester moiety, or the like in the structure of the nucleic acid is replaced with other atoms, for example, such as a sulfur atom.

In addition, in the sugar binding to the base at the 5'-end of each of the antisense strand and the sense strand, the hydroxyl group at the 5'-end may be modified with a phosphate group or the foregoing modifying group, or a group which is converted into a phosphate group or the foregoing modifying group by a nucleolytic enzyme or the like in a living body.

In addition, in the sugar binding to the base at the 3'-end of each of the antisense strand and the sense strand, the hydroxyl group at the 3'-end may be modified with a phosphate group or the foregoing modifying group, or a group which is converted into a phosphate group or the foregoing modifying group by a nucleolytic enzyme or the like in a living body.

The single-stranded nucleic acid may be any of nucleic acids that contain a sequence complementary to the contiguous 15 to 27 base sequence, preferably 15 to 25 base sequence, more preferably 15 to 23 base sequence, further preferably 15 to 21 base sequence, particularly preferably 15 to 19 base sequence of the target gene, with or without the substitution, deletion, or addition of 1 to 3 bases, preferably 1 to 2 bases, more preferably 1 base, and that have a target protein expression suppressing activity. Preferred for use is a single-stranded nucleic acid having 15 to at most 30 bases, preferably 15 to 29 bases, more preferably 15 to 27 bases, further preferably 15 to 25 bases, particularly preferably 15 to 23 bases.

The single-stranded nucleic acid may be one obtained by connecting the antisense strand and the sense strand of the double-stranded nucleic acid via a spacer sequence. Preferred as the spacer oligonucleotide is a single-stranded nucleic acid molecule of 6 to 12 bases, with a UU sequence at the 5'-end. Examples of the spacer oligonucleotide contain a nucleic acid having the sequence UUCAAGAGA. Either the antisense strand or the sense strand joined by a spacer oligonucleotide may represent the 5'-end. Preferably, the single-stranded nucleic acid is a single-stranded nucleic acid, such as shRNA, that has a stem-loop structure with a double-stranded portion. Single-stranded nucleic acids such as shRNA are typically 50 to 70 bases long.

It is also possible to use nucleic acids at most 70 bases long, preferably at most 50 bases long, further preferably at most 30 bases long, designed to generate the single-stranded nucleic acid or the double-stranded nucleic acid by the activity of ribonuclease or the like.

In addition, the nucleic acids used in the present invention may be produced by using known RNA or DNA synthesis techniques, and RNA or DNA modification techniques. For example, the nucleic acids may be chemically synthesized and obtained from Hokkaido System Science Co., Ltd.

Examples of the composition in the present invention include a composition comprising a complex particle of the cationic lipid of the present invention and a nucleic acid, a composition comprising a complex particle of a nucleic acid and the cationic lipid of the present invention combined with neutral lipid and/or a polymer, a lipid particle constituted of the complex particle and a lipid membrane encapsulating the complex particle, and the like. Examples of the lipid particle include a composition comprising a liposome constituted of the complex particle and a lipid bilayer encapsulating the complex particle, and the like. Examples of the complex particle include a complex of a nucleic acid and a membrane constituted of lipid bilayer, a complex of a nucleic acid and a liposome, a complex of a nucleic acid and a micelle, and the like. Preferred are a complex of a nucleic acid and a micelle, and a complex of a nucleic acid and a liposome.

The composition in the present invention can be produced by a known production method or a method in conformity therewith and may be a composition produced by any production method. For example, in the production of a liposome as one of the composition, a known preparation method of a liposome can be applied. Examples of the known preparation method of a liposome include a liposome preparation method by Bangham et al. (see *J. Mol. Biol.,* 1965, Vol. 13, pp. 238-252); an ethanol injection method (see *J. Cell. Biol.,* 1975, Vol. 66, pp. 621-634); a French press method (see *FEBS Lett.,* 1979, Vol. 99, pp. 210-214); a freeze-thawing method (see *Arch. Biochem. Biophys.,* 1981, Vol. 212, pp. 186-194); a reverse phase evaporation method (see *Proc. Natl. Acad. Sci. USA,* 1978, Vol. 75, pp. 4194-4198); and a pH gradient method (see, for example, Japanese Patents Nos. 2572554 and 2659136, etc.). As a solution which disperses the liposome in the production of liposome, for example, water, an acid, an alkali, a variety of buffer solution, a saline, an amino acid infusion, and the like can be used. In addition, in the production of a liposome, it is also possible to add an antioxidant, for example, citric acid, ascorbic acid, cysteine, ethylenediaminetetraacetic acid (EDTA), etc., an isotonic agent, for example, glycerin, glucose, sodium chloride, etc., or the like. In addition, the liposome can also be produced by dissolving a lipid or the like in an organic solvent, for example, ethanol, etc., distilling off the solvent, adding a saline or the like, and stirring and shaking the mixture, thereby forming a liposome.

In addition, the composition of the present invention can be produced by various methods. As an example, the cationic lipid of the present invention is dissolved in chloroform in advance, and a nucleic acid aqueous solution and methanol are added. These are mixed to form a cationic lipid/nucleic acid complex. Then, the chloroform layer is removed, and a water-in-oil (W/O) emulsion is formed by addition of a polyethylene glycolated phospholipid, a neutral lipid, and water. The mixture is then treated by using a reverse phase evaporation method (see JP-T-2002-508765; the term "JP-T" as used herein means a published Japanese translation of a PCT patent application). In another method, a nucleic acid is dissolved in an acidic electrolytic aqueous solution, and lipid is added (in ethanol) to lower the ethanol concentration to 20 v/v % and form the nucleic acid-encapsulating liposome. After sizing filtration, excess amounts of ethanol are removed by dialysis. The nucleic acid adhering to the liposome surface is then removed by further dialysis at an increased sample pH (see JP-T-2002-501511, and Biochimica et Biophysica Acta, 2001, Vol. 1510, p. 152-166).

The production methods described in, for example, WO2002/28367 and WO2006/080118 can be used to produce the compositions of the present invention, specifically the liposome constituted of complex particle of the cationic lipid of the present invention and a nucleic acid, or the complex particle of a nucleic acid and the cationic lipid of the present invention combined with neutral lipid and/or a polymer, and a lipid bilayer encapsulating the complex particle.

The neutral lipid may be any lipid including a simple lipid, a complex lipid, and a derived lipid. Examples thereof include a phospholipid, a glyceroglycolipid, a sphingoglycolipid, a sphingoid, and a sterol. However, it should not be construed that the present invention is limited thereto.

Examples of the phospholipid in the neutral lipid include natural or synthetic phospholipids such as phosphatidylcholines (specifically, soybean phosphatidylcholine, egg yolk phosphatidylcholine (EPC), distearoyl phosphatidylcholine (DSPC), dipalmitoyl phosphatidylcholine (DPPC), palmitoyloleoyl phosphatidylcholine (POPC), dimyristoyl phosphatidylcholine (DMPC), dioleoyl phosphatidylcholine (DOPC), etc.), phosphatidylethanolamines (specifically, distearoyl phosphatidylethanolamine (DSPE), dipalmitoyl phosphatidylethanolamine (DPPE), dioleoyl phosphatidylethanolamine (DOPE), dimyristoyl phosphoethanolamine (DMPE), 16-O-monomethyl PE, 16-O-dimethyl PE, 18-1-trans PE, palmitoyloleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyloleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphate, etc.), a glycerophosphono lipid, a sphingophosphonolipid, natural lecithins (specifically, egg yolk lecithin, soybean lecithin, etc.), and hydrogenated phospholipids (specifically, hydrogenated soybean phosphatidylcholine, etc.).

Examples of the glyceroglycolipid in the neutral lipid include sulfoxyribosyl glyceride, diglycosyl diglyceride, digalactosyl diglyceride, galactosyl diglyceride, and glycosyl diglyceride.

Examples of the sphingoglycolipid in the neutral lipid include galactosyl cerebroside, lactosyl cerebroside, and ganglioside.

Examples of the sphingoid in the neutral lipid include sphingan, icosasphingan, sphingosine, and a derivative thereof. Examples of the derivative include those in which —NH$_2$ of sphingan, icosasphingan, sphingosine, or the like is replaced with —NHCO(CH$_2$)$_x$CH$_3$ (in the formula, x is an integer of 0 to 18, with 6, 12 or 18 being preferable).

Examples of the sterol in the neutral lipid include cholesterol, dihydrocholesterol, lanosterol, β-sitosterol, campesterol, stigmasterol, brassicasterol, ergocasterol, fucosterol, and 3β-[N—(N',N'-dimethylaminoethyl)carbamoyl]cholesterol (DC-Chol).

The polymer may be one or more micelles selected from, for example, protein, albumin, dextran, polyfect, chitosan, dextran sulfate; and polymers, for example, such as poly-L-lysine, polyethyleneimine, polyaspartic acid, a copolymer of styrene and maleic acid, a copolymer of isopropylacrylamide and acrylpyrrolidone, polyethylene glycol (PEG)-modified dendrimer, polylactic acid, polylactic acid polyglycolic acid, and polyethylene glycolated polylactic acid, and a salt thereof.

Here, the salt of the polymer includes, for example, a metal salt, an ammonium salt, an acid addition salt, an organic amine addition salt, an amino acid addition salt, and the like. Examples of the metal salt include alkali metal salts such as a lithium salt, a sodium salt and a potassium salt; alkaline earth metal salts such as a magnesium salt and a calcium salt; an aluminum salt; a zinc salt, and the like. Examples of the ammonium salt include salts of ammonium, tetramethylammonium, and the like. Examples of the acid addition salt include inorganates such as a hydrochloride, a sulfate, a nitrate, and a phosphate, and organates such as an acetate, a maleate, a fumarate, and a citrate. Examples of the organic amine addition salt include addition salts of morpholine, piperidine, and the like, and examples of the amino acid addition salt include addition salts of glycine, phenylalanine, aspartic acid, glutamic acid, lysine, and the like.

Further, the composition of the present invention may comprise, for example, a lipid conjugate or a fatty acid conjugate of at least one substance selected from sugar, peptide, nucleic acid, and water-soluble polymer. The composition may also comprise a surfactant or the like. A lipid conjugate or a fatty acid conjugate of at least one substance selected from sugar, peptide, nucleic acid, and water-soluble polymer, or a surfactant may be comprised in the composite particle, or may be added external to the composite particle.

The lipid conjugate or fatty acid conjugate of at least one substance selected from sugar, peptide, nucleic acid, and water-soluble polymer, or the surfactant is preferably a glycolipid, or a lipid conjugate or a fatty acid conjugate of a water-soluble polymer, more preferably a lipid conjugate or a fatty acid conjugate of a water-soluble polymer. Preferably, the lipid conjugate or fatty acid conjugate of at least one substance selected from sugar, peptide, nucleic acid, and water-soluble polymer, or the surfactant is a substance having dual properties in which a part of the molecule has the property to bind to the other constituent components of the composition through, for example, hydrophobic affinity, electrostatic interaction, and the like, whereas other parts of the molecule have the property to bind to the solvent used for the production of the composition, through, for example, hydrophilic affinity, electrostatic interaction, and the like.

Examples of the lipid conjugate or fatty acid conjugate of sugar, peptide or nucleic acid include products formed by means of binding of sugars (such as sucrose, sorbitol, lactose, etc), peptides (such as casein-derived peptides, egg white-derived peptides, soybean-derived peptides, glutathione, etc) or nucleic acids (such as DNA, RNA, plasmids, siRNA ODN, etc) with the neutral lipids as exemplified above in the definition of the composition or the cationic lipids of the present invention, or with fatty acids (such as stearic acid, palmitic acid, myristic acid, lauric acid, etc).

Examples of the lipid conjugate or fatty acid conjugate of sugar include the glyceroglycolipids, the sphingoglycolipids, and the like as exemplified above in the definition of the composition.

Examples of the lipid conjugate or fatty acid conjugate of water-soluble polymer include products formed by means of binding of, for example, polyethylene glycol, polyglycerin, polyethyleneimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartamide, poly-L-lysine, mannan, pullulan, oligoglycerol, etc, and derivatives thereof with the neutral lipids as exemplified above in the definition of the composition, the cationic lipids of the present invention, or fatty acids (such as stearic acid, palmitic acid, myristic acid, lauric acid, etc). More preferred examples thereof include lipid conjugates or fatty acid conjugates of polyethylene glycol derivatives, polyglycerin derivatives, and the like. Further preferred examples thereof include lipid conjugates or fatty acid conjugates of polyethylene glycol derivatives.

Examples of the lipid conjugate or fatty acid conjugate of a polyethylene glycol derivative include a polyethylene glycolated lipid (specifically, polyethylene glycol-phosphatidylethanolamines (more specifically, 1,2-distearoyl-sn-glycero-3-phosphoethanolamine-N-[methoxy(polyethylene glycol)-2000] (PEG-DSPE), 1,2-dimyristoyl-sn-glycero-3-phosphoethanolamine-N-[methoxy(polyethylene glycol)-2000] (PEG-DMPE), etc.)), polyoxyethylene hydrogenated castor oil 60, CREMOPHOR EL, and the like), a polyethylene glycol sorbitan fatty acid ester (specifically, polyoxyethylenesorbitanmonooleate, etc.), and a polyethylene glycol fatty acid ester; preferred examples thereof include a polyethylene glycolated lipid.

Examples of the lipid conjugate or the fatty acid conjugate of a polyglycerol derivative include a polyglycerolated lipid (specifically, polyglycerol phosphatidyl ethanolamine and the like), a polyglycerol fatty acid ester and the like, and more preferred examples include a polyglycerolated lipid.

Examples of the surfactant include polyoxyethylene sorbitan monooleates (specifically, Polysorbate 80, and the like), polyoxyethylene polyoxypropylene glycols (specifically, Pluronic F68, and the like), sorbitan fatty acid esters (specifically, sorbitan monolaurate, sorbitan monooleate, and the like), polyoxyethylene derivatives (specifically, polyoxyethylene hydrogenated castor oil 60, polyoxyethylene lauryl alcohol, and the like), glycerin fatty acid esters, and polyethylene glycolalkyl ethers. Preferred examples thereof include polyoxyethylene polyoxypropylene glycols, glycerin fatty acid esters, polyethylene glycolalkyl ethers, and the like.

When the composition of the present invention is a liposome, the composition of the liposome may be subjected to any surface modification with, for example, a polymer, a polyoxyethylene derivative, and the like. [see D. D. Lasic, F. Martin], *Stealth Liposomes*, CRC Press Inc., US, 1995, p. 93-102]. Examples of polymers usable for the surface modification include dextran, pullulan, mannan, amylopectin, hydroxyethyl starch, and the like. Examples of the polyoxyethylene derivatives include Polysorbate 80, Pluronic F68, polyoxyethylene hydrogenated castor oil 60, polyoxyethylene lauryl alcohol, PEG-DSPE, and the like. The surface modification of the composition such as the liposome enables the composition to comprise a lipid conjugate or a fatty acid conjugate of at least one substance selected from sugar, peptide, nucleic acid, and water-soluble polymer, or a surfactant.

The average particle diameter of the composition in the present invention may be freely selected as desired. Preferably, the average particle diameter of the liposome is adjusted as follows. Examples of a method for adjusting the average particle diameter include an extrusion method, a method in which a large multilamellar liposome vesicle (MLV) and like is mechanically pulverized (specifically, by using Manton-gaulin, a microfluidizer or the like) (see *Emulsion and Nanosuspensions for the Formulation of Poorly Soluble Drugs*, edited by R. H. Muller, S. Benita and B. Bohm, Scientific Publishers, Stuttgart, Germany, pp. 267-294, 1998), and the like.

A complex as a combination of two or more selected from, for example, a lipid assembly, a liposome, a polymer micelle, and the like used as the composition may be produced simply by mixing the lipid, polymer, and the like, for example, in water. Other step such as a granulating step and a sterilizing step may be added, as desired. The complex may be produced in various solvents, for example, acetone, ether, and the like.

As for the size of the composition in the present invention, an average particle diameter is preferably about 10 nm to 1,000 nm, more preferably about 30 nm to 300 nm, and still more preferably about 50 nm to 200 nm.

By administering the composition in the present invention to a mammalian cell, the nucleic acid in the composition in the present invention can be introduced into the cell.

A method for administering the composition in the present invention to a mammalian cell in vitro may be carried out according to the procedures of known transfection capable of being carried out in vitro.

A method for administering the composition of the present invention to a mammalian cell in vivo may be carried out according to the procedures of known transfection that can be performed in vivo. For example, by the intravenous administration of the composition of the present invention to mammals including humans, the composition is delivered to, for example, an organ or a site involving cancer or inflammation, and the nucleic acid in the composition of the present invention can be introduced into the cells at these organs or sites. The organs or sites involving cancer or inflammation are not particularly limited. Examples thereof include stomach, large intestine, liver, lungs, spleen, pancreas, kidneys, bladder, skin, blood vessel, and eye ball. In addition, by the intravenous administration of the composition of the present invention to mammals including humans, the composition can be delivered to, for example, blood vessel, liver, lungs, spleen, and/or kidneys, and the nucleic acid in the composition of the present invention can be introduced into the cells at these organs or sites. The liver, lung, spleen, and/or kidney cells may be any of normal cells, cells associated with cancer or inflammation, and cells associated with other diseases.

When the nucleic acid in the composition in the present invention is a nucleic acid having an activity of suppressing the expression of the target gene by utilizing RNA interference (RNAi), nucleic acids such as RNA that suppress the expression of the gene can be introduced to mammalian cells in vivo, and expression of genes can be suppressed. The administration target is preferably human.

In addition, when the target gene of composition in the present invention is, for example, a gene associated with tumor or inflammation, the composition of the present invention can be used as a therapeutic agent or a preventive agent for cancer or inflammatory disease, preferably a therapeutic agent or a preventive agent for solid cancer or for inflammation in blood vessels or in the vicinity of blood vessels. Specifically, when the target gene of the composition of the present invention is, for example, a gene associated with angiogenesis, the composition of the present invention can suppress the proliferation, angiogenesis, or the like in the vascular smooth muscle, and can thus be used as a therapeutic agent or a preventive agent for cancer or inflammatory disease that involves, for example, proliferation or angiogenesis in the vascular smooth muscle.

Specifically, the present invention also provides a cancer or inflammatory disease therapeutic method that includes administering the composition of the present invention to a mammal. The administration target is preferably human, more preferably humans having cancer or inflammatory disease.

Further, the composition of the present invention also can be used as a tool for acquiring a POC (proof of concept) in an in vivo screening system concerning the cancer or inflammatory disease therapeutic or preventive agent.

The composition of the present invention also can be used as a preparation for, for example, stabilizing the nucleic acid in biogenic substances (for example, blood, digestive tract, and the like) such as blood components, reducing side effects, or increasing drug accumulation in tissues or organs containing the expression site of the target gene.

When the composition of the present invention is used as a medicament, specifically a therapeutic agent or a preventive agent for cancer, inflammatory disease, or the like, it is desirable to use an administration route that is most effective for the treatment. The administration route may be parenteral or oral, including buccal administration, airway administration, rectal administration, subcutaneous administration, intramuscular administration, intravenous administration, and the like. Intravenous administration and intramuscular administration are preferable, and intravenous administration is more preferable.

The dose may vary depending upon factors such as the conditions and the age of a subject, and the administration route. For example, the administration may be made in a daily dose of, for example, about 0.1 µg to 1,000 mg in terms of the nucleic acid.

As a preparation suitable for the intravenous administration or intramuscular administration, for example, an injection can be exemplified, and it is also possible to use a dispersion liquid of the composition prepared by the foregoing method as it is in the form of, for example, an injection or the like. However, it can also be used after removing the solvent from the dispersion liquid by, for example, filtration, centrifugation, or the like, or after lyophilizing the dispersion liquid or the dispersion liquid supplemented with an excipient such as mannitol, lactose, trehalose, maltose, and glycine.

In the case of an injection, it is preferable that an injection is prepared by mixing, for example, water, an acid, an alkali, a variety of buffer solution, a saline, an amino acid infusion, or the like with the foregoing dispersion liquid of the composition or the foregoing composition obtained by removing the solvent or lyophilization. In addition, it is also possible to prepare an injection by adding an antioxidant such as citric acid, ascorbic acid, cysteine, and EDTA, an isotonic agent such as glycerin, glucose, and sodium chloride, or the like. In addition, it can also be cryopreserved by adding a cryopreservation agent such as glycerin.

Next, the present invention is specifically described with reference to the following Examples and Test Examples. However, it should not be construed that the present invention is limited to these Examples and Test Examples.

Incidentally, proton nuclear magnetic resonance spectra ($^1$H NMR) shown in Examples and Referential Examples are those measured at 270 MHz, 300 MHz or 400 MHz, and there may be the case where an exchangeable proton is not distinctly observed depending upon the compound and measuring conditions. Incidentally, the expression for multiplicity of a signal is a usually used expression. The term "br" indicates an apparently broad signal.

Reference Example 1

(3R,4R)-1-Benzyl-3,4-bis((9Z,12Z)-octadec-9,12-dienyloxy)pyrrolidine (compound VI-1)

A toluene (70 mL) solution of (3R,4R)-1-benzylpyrrolidine-3,4-diol (Diverchim S.A.; 3.50 g, 18.1 mmol) was slowly added to a toluene (100 mL) suspension of sodium hydride (oily, 60%, 5.80 g, 145 mmol) while being stirred. A toluene (30 mL) solution of (9Z,12Z)-octadec-9,12-dienyl methanesulfonate (Nu-Chek Prep., Inc.; 15.6 g, 45.3 mmol) was then dropped on the mixture. The resulting mixture was stirred overnight under heat and reflux. After cooling the mixture to room temperature, the reaction was stopped with a saturated ammonium chloride aqueous solution. After adding saturated brine, the mixture was extracted twice with ethyl acetate. The organic layers were combined, dried over anhydrous magnesium sulfate, and concentrated under reduced pressure. The residue was purified by silica gel column chromatography (methanol/chloroform=0/100 to 2/98) to give compound VI-1 (6.96 g, 55.7%).

ESI-MS m/z: 691 (M+H)$^+$; $^1$H-NMR (CDCl$_3$) δ: 0.89 (t, J=6.9 Hz, 6H), 1.26-1.38 (m, 30H), 1.52-1.62 (m, 6H), 2.05 (q, J=6.3 Hz, 8H), 2.50 (dd, J=9.9, 4.3 Hz, 2H), 2.77 (t, J=5.8

Hz, 4H), 2.85 (dd, J=9.6, 5.9 Hz, 2H), 3.37-3.45 (m, 4H), 3.52-3.66 (m, 2H), 3.83 (t, J=4.6 Hz, 2H), 5.28-5.43 (m, 8H), 7.23-7.33 (m, 5H).

Reference Example 2

(3R,4R)-1-Benzylpyrrolidine-3,4-diyl di((9Z,12Z)-octadec-9,12-dienoate) (compound VI-2)

(3R,4R)-1-Benzylpyrrolidine-3,4-diol (Diverchim S.A.; 350 mg, 1.81 mmol) was dissolved in dichloromethane (18 mL). After adding linoleic acid (Aldrich; 1.24 mL, 3.98 mmol), dicyclohexylcarbodiimide (Kokusan Chemical Co., Ltd.; 860 mg, 4.17 mmol), and 4-dimethylaminopyridine (Tokyo Chemical Industry Co., Ltd.; 55.3 mg, 0.453 mmol), the mixture was stirred overnight at room temperature. After adding hexane (18 mL), the reaction mixture was filtered, and concentrated under reduced pressure. The resulting residue was purified by silica gel column chromatography (hexane/chloroform=40/60 to 20/80) to give compound VI-2 (1.21 g, 93.0%).
ESI-MS m/z: 719 (M+H)$^+$; $^1$H-NMR (CDCl$_3$) δ: 0.89 (t, J=6.8 Hz, 6H), 1.30-1.40 (m, 28H), 1.55-1.64 (m, 4H), 2.05 (q, J=6.6 Hz, 8H), 2.30 (t, J=7.5 Hz, 4H), 2.50 (dd, J=10.3, 4.0 Hz, 2H), 2.77 (t, J=6.1 Hz, 4H), 3.06 (dd, J=10.3, 6.1 Hz, 2H), 3.62 (q, J=13.8 Hz, 2H), 5.12 (dd, J=5.3, 4.0 Hz, 2H), 5.28-5.43 (m, 8H), 7.23-7.34 (m, 5H).

Reference Example 3

(3R,4R)-1-Benzyl-3,4-bis((9Z,12Z)-octadec-9,12-dienyloxy)pyrrolidine (Compound VI-3)

Compound VI-3 (398 mg, 40.7%) was obtained in the same manner as that in Reference Example 1, by using (3R,4S)-1-benzylpyrrolidine-3,4-diol (Diverchim S.A.; 274 mg, 1.42 mmol) and (9Z,12Z)-octadec-9,12-dienyl methanesulfonate (Nu-Chek Prep, Inc; 1.22 g, 3.54 mmol).
ESI-MS m/z: 691 (M+H)$^+$; $^1$H-NMR (CDCl$_3$) δ: 0.89 (t, J=6.6 Hz, 6H), 1.29-1.40 (m, 30H), 1.56 (dd, J=13.0, 7.1 Hz, 6H), 2.05 (q, J=6.6 Hz, 8H), 2.46 (dd, J=9.5, 6.0 Hz, 2H), 2.77 (t, J=6.0 Hz, 4H), 3.08 (dd, J=9.5, 6.0 Hz, 2H), 3.37-3.53 (m, 4H), 3.63 (s, 2H), 3.85-3.92 (m, 2H), 5.28-5.43 (m, 8H), 7.20-7.30 (m, 5H).

Reference Example 4

(3R,4R)-1-Benzyl-3,4-bis((Z)-octadec-9-enyloxy)pyrrolidine (Compound VI-4)

Compound VI-4 (507 mg, 56.4%) was obtained in the same manner as that in Reference Example 1, by using (3R,4R)-1-benzylpyrrolidine-3,4-diol (Diverchim S.A.; 250 mg, 1.29 mmol) and (Z)-octadec-9-enyl methanesulfonate (Nu-Chek Prep, Inc; 1.79 g, 5.17 mmol).
ESI-MS m/z: 695 (M+H)$^+$; $^1$H-NMR (CDCl$_3$) δ: 0.88 (t, J=6.6 Hz, 6H), 1.26-1.36 (m, 44H), 1.53-1.58 (m, 4H), 2.01 (q, J=5.9 Hz, 8H), 2.50 (dd, J=9.9, 4.7 Hz, 2H), 2.85 (dd, J=9.9, 6.1 Hz, 2H), 3.34-3.47 (m, 4H), 3.59 (q, J=12.6 Hz, 2H), 3.83 (t, J=4.7 Hz, 2H), 5.29-5.40 (m, 4H), 7.23-7.32 (m, 5H).

Reference Example 5

(3R,4R)-1-Benzyl-3,4-bis(tetradecyloxy)pyrrolidine (compound VI-5)

(3R,4R)-1-Benzylpyrrolidine-3,4-diol (Diverchim S.A.; 150 mg, 0.776 mmol) was dissolved in dimethylsulfoxide (4 mL). After adding potassium hydroxide (348 mg, 6.21 mmol), the solution was stirred at 100° C. for 15 minutes. The reaction solution was further stirred at 100° C. for 4 hours after adding a dimethylsulfoxide (4 mL) solution of tetradecyl methanesulfonate (Nu-Chek Prep., Inc.; 568 mg, 1.94 mmol). The mixture was cooled to room temperature, and, after adding water, the aqueous layer was extracted with ethyl acetate. The organic layer was washed with water and a saturated sodium chloride aqueous solution, dried over anhydrous magnesium sulfate, and concentrated under reduced pressure after filtration. The resulting residue was purified by silica gel column chromatography (chloroform 100%) to give compound VI-5 (449 mg, 98.6%).
ESI-MS m/z: 587 (M+H)$^+$; $^1$H-NMR (CDCl$_3$) δ: 0.88 (t, J=6.6 Hz, 6H), 1.25-1.33 (m, 44H), 1.51-1.60 (m, 4H), 2.50 (dd, J=9.9, 4.7 Hz, 2H), 2.85 (dd, J=9.9, 6.0 Hz, 2H), 3.35-3.47 (m, 4H), 3.59 (q, J=12.8 Hz, 2H), 3.83 (t, J=4.7 Hz, 2H), 7.21-7.33 (m, 5H).

Reference Example 6

(3R,4R)-1-Benzyl-3,4-bis((Z)-hexadec-9-enyloxy)pyrrolidine (Compound VI-6)

Compound VI-6 (231 mg, 48.0%) was obtained in the same manner as that in Reference Example 1, by using (3R,4R)-1-benzylpyrrolidine-3,4-diol (Diverchim S.A.; 146 mg, 0.753 mmol) and (Z)-hexadec-9-enyl methanesulfonate (Nu-Chek Prep, Inc; 600 mg, 1.88 mmol).
ESI-MS m/z: 639 (M+H)$^+$; $^1$H-NMR (CDCl$_3$) δ: 0.88 (t, J=6.8 Hz, 6H), 1.28-1.37 (m, 36H), 1.50-1.60 (m, 4H), 2.01 (q, J=5.9 Hz, 8H), 2.50 (dd, J=9.8, 4.6 Hz, 2H), 2.85 (dd, J=9.8, 5.9 Hz, 2H), 3.34-3.47 (m, 4H), 3.59 (q, J=12.6 Hz, 2H), 3.83 (t, J=4.6 Hz, 2H), 5.29-5.40 (m, 4H), 7.20-7.34 (m, 5H).

Reference Example 7

(3R,4R)-1-Benzyl-3,4-bis((Z)-octadec-6-enyloxy)pyrrolidine (Compound VI-7)

Compound VI-7 (196 mg, 40.7%) was obtained in the same manner as that in Reference Example 1, by using (3R,4R)-1-benzylpyrrolidine-3,4-diol (Diverchim S.A.; 134 mg, 0.693 mmol) and (Z)-octadec-6-enyl methanesulfonate (Nu-Chek Prep, Inc; 600 mg, 1.73 mmol).
ESI-MS m/z: 695 (M+H)$^+$; $^1$H-NMR (CDCl$_3$) δ: 0.88 (t, J=6.6 Hz, 6H), 1.26-1.37 (m, 44H), 1.52-1.61 (m, 4H), 1.97-2.05 (m, 8H), 2.50 (dd, J=9.9, 4.6 Hz, 2H), 2.85 (dd, J=9.9, 5.9 Hz, 2H), 3.34-3.48 (m, 4H), 3.59 (q, J=11.8 Hz, 2H), 3.83 (t, J=4.6 Hz, 2H), 5.28-5.41 (m, 4H), 7.22-7.34 (m, 5H).

Reference Example 8

(3R,4R)-1-Benzyl-3,4-bis((11Z,14Z)-icos-11,14-dienyloxy)pyrrolidine (Compound VI-8)

Compound VI-8 (210 mg, 43.7%) was obtained in the same manner as that in Reference Example 1, by using (3R,4R)-1-benzylpyrrolidine-3,4-diol (Diverchim S.A.; 124 mg, 0.644 mmol) and (11Z,14Z)-icos-11,14-dienyl methanesulfonate (Nu-Chek Prep, Inc; 600 mg, 1.61 mmol).
ESI-MS m/z: 747 (M+H)$^+$; $^1$H-NMR (CDCl$_3$) δ: 0.89 (t, J=6.8 Hz, 6H), 1.27-1.40 (m, 40H), 1.51-1.60 (m, 4H), 2.05 (q, J=6.5 Hz, 8H), 2.50 (dd, J=10.0, 4.5 Hz, 2H), 2.77 (t, J=6.1 Hz, 4H), 2.85 (dd, J=10.0, 6.1 Hz, 2H), 3.35-3.47 (m, 4H), 3.59 (q, J=12.8 Hz, 2H), 3.83 (t, J=4.5 Hz, 2H), 5.29-5.43 (m, 8H), 7.22-7.33 (m, 5H).

Reference Example 9

(3R,4R)-1-Benzylpyrrolidine-3,4-diyl di((Z)-octadec-9-enoate) (Compound VI-9)

Compound VI-9 (1.85 g, 98.8%) was obtained in the same manner as that in Reference Example 2, by using (3R,4R)-1-benzylpyrrolidine-3,4-diol (Diverchim S.A.; 500 mg, 2.59 mmol) and oleic acid (Tokyo Chemical Industry Co., Ltd.; 1.61 g, 5.69 mmol).
ESI-MS m/z: 723 (M+H)$^+$; $^1$H-NMR (CDCl$_3$) δ: 0.88 (t, J=6.6 Hz, 6H), 1.27-1.35 (m, 40H), 1.55-1.65 (m, 4H), 2.01 (q, J=5.6 Hz, 8H), 2.30 (t, J=7.4 Hz, 4H), 2.50 (dd, J=10.2, 4.1 Hz, 2H), 3.06 (dd, J=10.2, 6.3 Hz, 2H), 3.63 (q, J=12.9 Hz, 2H), 5.12 (dd, J=5.1, 4.1 Hz, 2H), 5.28-5.40 (m, 4H), 7.23-7.34 (m, 5H).

Reference Example 10

(3S,4S)-1-Benzyl-3,4-bis((9Z,12Z)-octadec-9,12-dienyloxy)pyrrolidine (Compound VI-10)

Compound VI-10 (966 mg, 54.1%) was obtained in the same manner as that in Reference Example 1, by using (3S,4S)-1-benzylpyrrolidine-3,4-diol (Diverchim S.A.; 500 mg, 2.59 mmol) and (9Z,12Z)-octadec-9,12-dienyl methanesulfonate (Nu-Chek Prep, Inc; 2.23 g, 6.47 mmol).
ESI-MS m/z: 691 (M+H)$^+$; $^1$H-NMR (CDCl$_3$) δ: 0.89 (t, J=6.4 Hz, 6H), 1.28-1.38 (m, 32H), 1.50-1.60 (m, 4H), 2.04 (q, J=6.6 Hz, 8H), 2.49 (dd, J=10.0, 4.1 Hz, 2H), 2.75-2.88 (m, 6H), 3.34-3.47 (m, 4H), 3.59 (q, J=11.2 Hz, 2H), 3.82 (t, J=4.9 Hz, 2H), 5.27-5.43 (m, 8H), 7.21-7.31 (m, 5H).

Reference Example 11

(3R,4R)-1-Benzyl-3,4-bis(hexadecyloxy)pyrrolidine (Compound VI-11)

Compound VI-11 (324 mg, 97.6%) was obtained in the same manner as that in Reference Example 5, by using (3R,4R)-1-benzylpyrrolidine-3,4-diol (Diverchim S.A.; 100 mg, 0.517 mmol) and hexadecyl methanesulfonate (Nu-Chek Prep, Inc; 415 mg, 1.29 mmol).
ESI-MS m/z: 643 (M+H)$^+$; $^1$H-NMR (CDCl$_3$) δ: 0.88 (t, J=6.8 Hz, 6H), 1.25-1.33 (m, 52H), 1.50-1.58 (m, 4H), 2.50 (dd, J=9.9, 4.8 Hz, 2H), 2.85 (dd, J=9.9, 6.0 Hz, 2H), 3.35-3.47 (m, 4H), 3.59 (q, J=12.8 Hz, 2H), 3.83 (t, J=4.8 Hz, 2H), 7.20-7.33 (m, 5H).

Reference Example 12

(3R,4R)-1-Benzyl-3,4-bis(octadecyloxy)pyrrolidine (Compound VI-12)

Compound VI-12 (319 mg, 88.3%) was obtained in the same manner as that in Reference Example 5, by using (3R,4R)-1-benzylpyrrolidine-3,4-diol (Diverchim S.A.; 100 mg, 0.517 mmol) and octadecyl methanesulfonate (Nu-Chek Prep, Inc; 451 mg, 1.29 mmol).
ESI-MS m/z: 699 (M+H)$^+$; $^1$H-NMR (CDCl$_3$) δ: 0.88 (t, J=6.8 Hz, 6H), 1.25-1.33 (m, 60H), 1.51-1.59 (m, 4H), 2.50 (dd, J=9.8, 4.5 Hz, 2H), 2.85 (dd, J=9.8, 6.2 Hz, 2H), 3.35-3.47 (m, 4H), 3.59 (q, J=12.7 Hz, 2H), 3.83 (t, J=4.5 Hz, 2H), 7.21-7.33 (m, 5H).

Reference Example 13

(3R,4R)-1-Benzyl-3,4-bis((Z)-tetradec-9-enyloxy)pyrrolidine (Compound VI-13)

Compound VI-13 (119 mg, 49.5%) was obtained in the same manner as that in Reference Example 1, by using (3R,4R)-1-benzylpyrrolidine-3,4-diol (Diverchim S.A.; 80.0 mg, 0.414 mmol) and (Z)-tetradec-9-enyl methanesulfonate (Nu-Chek Prep, Inc; 301 mg, 1.04 mmol).
ESI-MS m/z: 583 (M+H)$^+$; $^1$H-NMR (CDCl$_3$) δ: 0.89 (t, J=7.0 Hz, 6H), 1.28-1.37 (m, 28H), 1.51-1.60 (m, 4H), 1.98-2.05 (m, 8H), 2.50 (dd, J=9.8, 4.6 Hz, 2H), 2.85 (dd, J=9.8, 6.0 Hz, 2H), 3.35-3.47 (m, 4H), 3.59 (q, J=12.6 Hz, 2H), 3.83 (t, J=4.6 Hz, 2H), 5.29-5.40 (m, 4H), 7.21-7.34 (m, 5H).

Reference Example 14

(3R,4R)-1-Benzyl-3,4-bis((Z)-octadec-11-enyloxy)pyrrolidine (Compound VI-14)

Compound VI-14 (244 mg, 60.8%) was obtained in the same manner as that in Reference Example 1, by using (3R,4R)-1-benzylpyrrolidine-3,4-diol (Diverchim S.A.; 112 mg, 0.577 mmol) and (Z)-octadec-11-enyl methanesulfonate (Nu-Chek Prep, Inc; 500 mg, 1.44 mmol).
ESI-MS m/z: 695 (M+H)$^+$; $^1$H-NMR (CDCl$_3$) δ: 0.88 (t, J=6.6 Hz, 6H), 1.26-1.35 (m, 44H), 1.51-1.59 (m, 4H), 2.01 (q, J=6.1 Hz, 8H), 2.50 (dd, J=9.9, 4.6 Hz, 2H), 2.85 (dd, J=9.9, 6.0 Hz, 2H), 3.35-3.47 (m, 4H), 3.59 (q, J=12.8 Hz, 2H), 3.83 (t, J=4.6 Hz, 2H), 5.30-5.40 (m, 4H), 7.21-7.34 (m, 5H).

Reference Example 15

(3R,4R)-1-Benzyl-3,4-bis((Z)-icos-11-enyloxy)pyrrolidine (Compound VI-15)

Compound VI-15 (251 mg, 62.7%) was obtained in the same manner as that in Reference Example 1, by using (3R,4R)-1-benzylpyrrolidine-3,4-diol (Diverchim S.A.; 103 mg, 0.534 mmol) and (Z)-icos-11-enyl methanesulfonate (Nu-Chek Prep, Inc; 500 mg, 1.34 mmol).
ESI-MS m/z: 751 (M+H)$^+$; $^1$H-NMR (CDCl$_3$) δ: 0.88 (t, J=6.8 Hz, 6H), 1.27-1.35 (m, 52H), 1.50-1.60 (m, 4H), 2.01 (q, J=6.0 Hz, 8H), 2.50 (dd, J=9.8, 4.4 Hz, 2H), 2.85 (dd, J=9.8, 6.2 Hz, 2H), 3.35-3.47 (m, 4H), 3.59 (q, J=12.8 Hz, 2H), 3.83 (t, J=4.4 Hz, 2H), 5.30-5.40 (m, 4H), 7.21-7.34 (m, 5H).

Reference Example 16

(trans-1-Benzylpyrrolidine-3,4-diyl)dimethanol trans-Diethyl 1-benzylpyrrolidine-3,4-dicarboxylate (830 mg, 2.72 mmol) synthesized by using WO2009/027820 as a reference was dissolved in THF (24 mL). After adding lithium aluminum hydride (206 mg, 5.44 mmol) at 0° C., the solution was stirred at room temperature for 1.3 hours. The reaction mixture was further stirred at room temperature after adding sodium sulfate decahydrate, chloroform, and Celite. The mixture was filtered after adding anhydrous magnesium sulfate, and the filtrate was concentrated under reduced pressure. Hexane was added, and the solid was removed by filtration to give (trans-1-benzylpyrrolidine-3,4-diyl)dimethanol (565 mg, 93.9%).

ESI-MS m/z: 222 (M+H)⁺; ¹H-NMR (CDCl₃) δ: 2.17-2.28 (m, 2H), 2.35 (dd, J=9.0, 5.1 Hz, 2H), 2.77 (dd, J=9.0, 7.1 Hz, 2H), 3.56-3.68 (m, 6H), 7.22-7.34 (m, 5H).

Reference Example 17 trans-1-Benzyl-3,4-bis(((Z)-hexadec-9-enyloxy)methyl)pyrrolidine (compound VI-16)

Compound VI-16 (372 mg, 82.3%) was obtained in the same manner as that in Reference Example 1, by using the (trans-1-benzylpyrrolidine-3,4-diyl)dimethanol (150 mg, 0.678 mmol) obtained in Reference Example 16, and (Z)-hexadec-9-enyl methanesulfonate (Nu-Chek Prep., Inc.; 540 mg, 1.70 mmol).

ESI-MS m/z: 667 (M+H)⁺; ¹H-NMR (CDCl₃) δ: 0.88 (t, J=6.8 Hz, 6H), 1.28-1.35 (m, 36H), 1.49-1.57 (m, 4H), 1.95-2.10 (m, 10H), 2.37 (dd, J=9.2, 5.5 Hz, 2H), 2.67 (dd, J=9.2, 7.0 Hz, 2H), 3.31-3.44 (m, 8H), 3.57 (dd, J=18.1, 13.0 Hz, 2H), 5.29-5.40 (m, 4H), 7.19-7.32 (m, 5H).

Reference Example 18

N-Benzyldiethanolamine

Diisopropylethylamine (2.99 mL, 17.1 mmol) and benzyl bromide (1.36 mL, 11.4 mmol) were added to a chloroform (46 mL) solution of diethanolamine (1.80 g, 17.1 mmol), and the solution was stirred for 5 hours under heat and reflux. The reaction solution was washed with water, saturated sodium bicarbonate water, and saturated brine, dried over magnesium sulfate, and evaporated after filtration. The resulting residue was purified by silica gel column chromatography (methanol/chloroform=0/100 to 12/88) to give N-benzyldiethanolamine (1.77 g, 79.4%).

ESI-MS m/z: 196 (M+H)⁺; ¹H-NMR (CDCl₃) δ: 2.29 (br s, 2H), 2.73 (t, J=5.3 Hz, 4H), 3.63 (t, J=5.3 Hz, 4H), 3.71 (s, 2H), 7.24-7.37 (m, 5H).

Reference Example 19

N-Benzyl-N,N-bis(2-((Z)-octadec-9-enyloxy)ethyl)amine (Compound VI-17)

Compound VI-17 (257 mg, 48.4%) was obtained in the same manner as that in Reference Example 1, by using N-benzyldiethanolamine (149 mg, 0.763 mmol) obtained in Reference Example 18 and (Z)-octadec-9-enyl methanesulfonate (Nu-Chek Prep, Inc; 661 mg, 1.91 mmol).

ESI-MS m/z: 697 (M+H)⁺; ¹H-NMR (CDCl₃) δ: 0.88 (t, J=6.8 Hz, 6H), 1.27 (br s, 44H), 1.50-1.58 (m, 4H), 1.97-2.04 (m, 8H), 2.74 (t, J=6.2 Hz, 4H), 3.37 (t, J=6.6 Hz, 4H), 3.50 (t, J=6.2 Hz, 4H), 3.71 (s, 2H), 5.29-5.40 (m, 4H), 7.21-7.35 (m, 5H).

Reference Example 20

N-Benzyl-N,N-bis(2-((Z)-tetradec-9-enyloxy)ethyl)amine (Compound VI-18)

Compound VI-18 (424 mg, 82.9%) was obtained in the same manner as that in Reference Example 1, by using N-benzyldiethanolamine (171 mg, 0.876 mmol) obtained in Reference Example 18 and (Z)-tetradec-9-enyl methanesulfonate (Nu-Chek Prep, Inc; 636 mg, 2.19 mmol).

ESI-MS m/z: 585 (M+H)⁺; ¹H-NMR (CDCl₃) δ: 0.89 (t, J=7.1 Hz, 6H), 1.25-1.35 (m, 28H), 1.50-1.57 (m, 4H), 1.97-2.05 (m, 8H), 2.74 (t, J=6.3 Hz, 4H), 3.37 (t, J=6.7 Hz, 4H), 3.50 (t, J=6.3 Hz, 4H), 3.71 (s, 2H), 5.29-5.40 (m, 4H), 7.19-7.36 (m, 5H).

Reference Example 21

N-Benzyl-N,N-bis(2-(tetradecyloxy)ethyl)amine (Compound VI-19)

Compound VI-19 (173 mg, 33.6%) was obtained in the same manner as that in Reference Example 5, by using N-benzyldiethanolamine (171 mg, 0.876 mmol) obtained in Reference Example 18 and tetradecyl methanesulfonate (Nu-Chek Prep, Inc; 640 mg, 2.19 mmol).

ESI-MS m/z: 589 (M+H)⁺; ¹H-NMR (CDCl₃) δ: 0.88 (t, J=6.6 Hz, 6H), 1.25 (br s, 44H), 1.50-1.58 (m, 4H), 2.74 (t, J=6.1 Hz, 4H), 3.37 (t, J=6.6 Hz, 4H), 3.50 (t, J=6.3 Hz, 4H), 3.71 (s, 2H), 7.21-7.36 (m, 5H).

Reference Example 22

N-Benzyl-N,N-bis(2-(hexadecyloxy)ethyl)amine (Compound VI-20)

Compound VI-20 (411 mg, 72.9%) was obtained in the same manner as that in Reference Example 5, by using N-benzyldiethanolamine (171 mg, 0.876 mmol) obtained in Reference Example 18 and hexadecyl methanesulfonate (Nu-Chek Prep, Inc; 702 mg, 2.19 mmol).

ESI-MS m/z: 645 (M+H)⁺; ¹H-NMR (CDCl₃) δ: 0.88 (t, J=6.6 Hz, 6H), 1.25 (br s, 52H), 1.50-1.58 (m, 4H), 2.74 (t, J=6.3 Hz, 4H), 3.37 (t, J=6.6 Hz, 4H), 3.50 (t, J=6.3 Hz, 4H), 3.71 (s, 2H), 7.21-7.36 (m, 5H).

Reference Example 23

N-Benzyl-N,N-bis(2-(octadecyloxy)ethyl)amine (Compound VI-21)

Compound VI-21 (421 mg, 68.7%) was obtained in the same manner as that in Reference Example 5, by using N-benzyldiethanolamine (171 mg, 0.876 mmol) obtained in Reference Example 18 and octadecyl methanesulfonate (Nu-Chek Prep, Inc; 763 mg, 2.19 mmol).

ESI-MS m/z: 701 (M+H)⁺; ¹H-NMR (CDCl₃) δ: 0.88 (t, J=6.6 Hz, 6H), 1.25 (br s, 60H), 1.49-1.58 (m, 4H), 2.74 (t, J=6.3 Hz, 4H), 3.37 (t, J=6.6 Hz, 4H), 3.50 (t, J=6.3 Hz, 4H), 3.71 (s, 2H), 7.19-7.35 (m, 5H).

Reference Example 24

N-Benzyl-N,N-bis(2-((Z)-hexadec-9-enyloxy)ethyl)amine (Compound VI-22)

Compound VI-22 (739 mg, 81.4%) was obtained in the same manner as that in Reference Example 1, by using N-benzyldiethanolamine (277 mg, 1.42 mmol) obtained in Reference Example 18 and (Z)-hexadec-9-enyl methanesulfonate (Nu-Chek Prep, Inc; 1.13 g, 3.55 mmol).

ESI-MS m/z: 641 (M+H)⁺; ¹H-NMR (CDCl₃) δ: 0.88 (t, J=6.6 Hz, 6H), 1.28-1.35 (m, 36H), 1.49-1.58 (m, 4H), 2.01

(q, J=5.5 Hz, 8H), 2.74 (t, J=6.2 Hz, 4H), 3.37 (t, J=6.6 Hz, 4H), 3.50 (t, J=6.2 Hz, 4H), 3.71 (s, 2H), 5.29-5.40 (m, 4H), 7.19-7.35 (m, 5H).

Reference Example 25 trans-1-Benzyl-3,4-bis(((Z)-octadec-9-enyloxy) methyl)pyrrolidine (Compound VI-23)

Compound VI-23 (359 mg, 73.4%) was obtained in the same manner as that in Reference Example 1, by using (trans-1-benzylpyrrolidine-3,4-diyl)dimethanol (150 mg, 0.678 mmol) obtained in Reference Example 16 and (Z)-octadec-9-enyl methanesulfonate (Nu-Chek Prep, Inc; 597 mg, 1.70 mmol).

ESI-MS m/z: 723 (M+H)$^+$; $^1$H-NMR (CDCl$_3$) δ: 0.88 (t, J=6.6 Hz, 6H), 1.27-1.36 (m, 44H), 1.48-1.57 (m, 4H), 1.98-2.08 (m, 10H), 2.37 (dd, J=9.0, 5.1 Hz, 2H), 2.67 (dd, J=9.0, 7.2 Hz, 2H), 3.31-3.43 (m, 8H), 3.52-3.63 (m, 2H), 5.29-5.40 (m, 4H), 7.21-7.31 (m, 5H).

Reference Example 26 trans-1-Benzyl-3,4-bis(((9Z,12Z)-octadec-9,12-dienyloxy)methyl)pyrrolidine (Compound VI-24)

Compound VI-24 (384 mg, 78.9%) was obtained in the same manner as that in Reference Example 1, by using (trans-1-benzylpyrrolidine-3,4-diyl)dimethanol (150 mg, 0.678 mmol) obtained in Reference Example 16 and (9Z, 12Z)-octadec-9,12-dienyl methanesulfonate (Nu-Chek Prep, Inc; 584 mg, 1.70 mmol).

ESI-MS m/z: 719 (M+H)$^+$; $^1$H-NMR (CDCl$_3$) δ: 0.89 (t, J=6.4 Hz, 6H), 1.28-1.40 (m, 32H), 1.48-1.57 (m, 4H), 2.05 (q, J=6.6 Hz, 10H), 2.37 (dd, J=9.0, 4.9 Hz, 2H), 2.67 (dd, J=9.0, 7.1 Hz, 2H), 2.77 (t, J=5.9 Hz, 4H), 3.30-3.43 (m, 8H), 3.51-3.63 (m, 2H), 5.28-5.43 (m, 8H), 7.20-7.31 (m, 5H).

Reference Example 27 trans-1-3,4-bis(((11Z,14Z)-icos-11,14-dienyloxy) methyl)pyrrolidine (Compound VI-25)

Compound VI-25 (423 mg, 80.6%) was obtained in the same manner as that in Reference Example 1, by using (trans-1-benzylpyrrolidine-3,4-diyl)dimethanol (150 mg, 0.678 mmol) obtained in Reference Example 16 and (11Z, 14Z)-icos-9,12-dienyl methanesulfonate (Nu-Chek Prep, Inc; 631 mg, 1.70 mmol).

ESI-MS m/z: 775 (M+H)$^+$; $^1$H-NMR (CDCl$_3$) δ: 0.89 (t, J=6.8 Hz, 6H), 1.27-1.38 (m, 40H), 1.49-1.57 (m, 4H), 2.05 (q, J=6.7 Hz, 10H), 2.37 (dd, J=9.2, 5.1 Hz, 2H), 2.67 (dd, J=9.1, 7.1 Hz, 2H), 2.77 (t, J=6.0 Hz, 4H), 3.31-3.43 (m, 8H), 3.52-3.62 (m, 2H), 5.29-5.43 (m, 8H), 7.21-7.31 (m, 5H).

Reference Example 28 trans-1-(tert-Butoxycarbonyl)-3,4-bis(((Z)-octadec-9-enyloxy)methyl)pyrrolidine (Compound XIII-1)

Compound XIII-1 (280 mg, 54.6%) was obtained in the same manner as that in Reference Example 2, by using trans-3,4-bis(hydroxymethyl)pyrrolidine-1-carboxylic acid tert-butyl ester (156 mg, 0.674 mmol) obtained by using the method described in WO2006/100036 and oleic acid (Tokyo Chemical Industry Co., Ltd.; 419 mg, 1.48 mmol).

ESI-MS m/z: 761 (M+H)$^+$; $^1$H-NMR (CDCl$_3$) δ: 0.88 (t, J=6.6 Hz, 6H), 1.25-1.46 (m, 36H), 1.46 (s, 9H), 1.46-1.66 (m, 8H), 1.97-2.04 (m, 8H), 2.27-2.38 (m, 6H), 3.10-3.23 (m, 2H), 3.53-3.66 (m, 2H), 4.03 (dd, J=10.8, 6.0 Hz, 2H), 4.14 (dd, J=10.8, 6.0 Hz, 2H), 5.28-5.40 (m, 4H).

Reference Example 29 trans-1-(tert-Butoxycarbonyl)-3,4-bis(((9Z,12Z)-octadec-9,12-dienoyloxy)methyl)pyrrolidine (Compound XIII-2)

Compound XIII-2 (351 mg, 71.7%) was obtained in the same manner as that in Reference Example 2, by using trans-3,4-bis(hydroxymethyl)pyrrolidine-1-carboxylic acid tert-butyl ester (150 mg, 0.674 mmol) obtained by using the method described in WO2006/100036 and linoleic acid (Aldrich; 400 mg, 1.48 mmol).

ESI-MS m/z: 757 (M+H)$^+$; $^1$H-NMR (CDCl$_3$) δ: 0.89 (t, J=6.8 Hz, 6H), 1.21-1.45 (m, 26H), 1.46 (s, 9H), 1.47-1.68 (m, 6H), 2.05 (q, J=6.7 Hz, 8H), 2.26-2.38 (m, 6H), 2.77 (t, J=5.9 Hz, 4H), 3.10-3.23 (m, 2H), 3.53-3.66 (m, 2H), 4.03 (dd, J=11.0, 6.0 Hz, 2H), 4.14 (dd, J=11.0, 6.0 Hz, 2H), 5.28-5.43 (m, 8H).

Example 1

(3R,4R)-3,4-bis((9Z,12Z)-Octadec-9,12-dienyloxy) pyrrolidine (compound 1)

Compound VI-1 (6.96 g, 10.1 mmol) obtained in Reference Example 1 was dissolved in 1,2-dichloroethane (100 mL), and stirred at 130° C. for 1 hour after adding 1-chloroethyl chloroformate (Tokyo Chemical Industry Co., Ltd.; 3.30 mL, 30.3 mmol). After adding methanol (100 mL), the reaction solution was further stirred at 130° C. for 1 hour. After being cooled to room temperature, the solution was concentrated under reduced pressure, and the resulting residue was purified by silica gel column chromatography (chloroform/methanol=100/0 to 92/8). Fractions comprising the compound were collected, washed with a saturated sodium bicarbonate aqueous solution and a saturated sodium chloride aqueous solution, and dried over anhydrous magnesium sulfate. After filtration, the residue was concentrated under reduced pressure to give compound 1 (5.56 g, 92.0%).

ESI-MS m/z: 601 (M+H)$^+$; $^1$H-NMR (CDCl$_3$) δ: 0.89 (t, J=6.9 Hz, 6H), 1.29-1.41 (m, 30H), 1.49-1.60 (m, 4H), 1.67 (br s, 3H), 2.05 (q, J=6.5 Hz, 8H), 2.75-2.85 (m, 6H), 3.09 (dd, J=12.4, 5.1 Hz, 2H), 3.37-3.49 (m, 4H), 3.76 (dd, J=5.0, 3.3 Hz, 2H), 5.28-5.43 (m, 8H).

Example 2

(3R,4R)-Pyrrolidine-3,4-diyl di((9Z,12Z)-octadec-9, 12-dienoate) (Compound 2)

Compound 2 (1.20 g, 90.9%) was obtained in the same manner as that in Example 1, by using Compound VI-2 (1.51 g, 2.10 mmol) obtained in Reference Example 2.

ESI-MS m/z: 629 (M+H)$^+$; $^1$H-NMR (CDCl$_3$) δ: 0.89 (t, J=6.8 Hz, 6H), 1.26-1.41 (m, 29H), 1.56-1.68 (m, 4H), 2.05 (q, J=6.4 Hz, 8H), 2.30 (t, J=7.6 Hz, 4H), 2.77 (t, J=5.8 Hz, 4H), 2.87 (dd, J=13.0, 3.0 Hz, 2H), 3.32 (dd, J=13.0, 5.0 Hz, 2H), 5.08 (dd, J=5.0, 3.0 Hz, 2H), 5.28-5.44 (m, 8H).

Example 3

(3R,4S)-3,4-bis((9Z,12Z)-Octadec-9,12-dienyloxy)pyrrolidine (Compound 3)

Compound 3 (245 mg, 81.3%) was obtained in the same manner as that in Example 1, by using Compound VI-3 (346 mg, 0.501 mmol) obtained in Reference Example 3.

ESI-MS m/z: 601 (M+H)$^+$; $^1$H-NMR (CDCl$_3$) δ: 0.89 (t, J=6.7 Hz, 6H), 1.30-1.40 (m, 30H), 1.54-1.68 (m, 8H), 2.05 (q, J=6.7 Hz, 8H), 2.77 (t, J=5.8 Hz, 4H), 3.00 (d, J=5.0 Hz, 3H), 3.41-3.55 (m, 4H), 3.83 (t, J=3.8 Hz, 2H), 5.28-5.43 (m, 8H).

Example 4

(3R,4R)-3,4-bis((Z)-Octadec-9-enyloxy)pyrrolidine (Compound 4)

Compound 4 (333 mg, 84.1%) was obtained in the same manner as that in Example 1, by using Compound VI-4 (455 mg, 0.655 mmol) obtained in Reference Example 4.

ESI-MS m/z: 605 (M+H)$^+$; $^1$H-NMR (CDCl$_3$) δ: 0.88 (t, J=6.5 Hz, 6H), 1.26-1.35 (m, 38H), 1.50-1.58 (m, 11H), 2.01 (q, J=6.5 Hz, 8H), 2.82 (dd, J=12.4, 3.0 Hz, 2H), 3.09 (dd, J=12.4, 5.0 Hz, 2H), 3.43 (td, J=6.5, 1.3 Hz, 4H), 3.76 (dd, J=5.0, 3.0 Hz, 2H), 5.30-5.40 (m, 4H).

Example 5

(3R,4R)-3,4-bis(Tetradecyloxy)pyrrolidine (Compound 5)

Compound 5 (331 mg, 86.1%) was obtained in the same manner as that in Example 1, by using Compound VI-5 (454 mg, 0.775 mmol) obtained in Reference Example 5.

ESI-MS m/z: 497 (M+H)$^+$; $^1$H-NMR (CDCl$_3$) δ: 0.88 (t, J=6.6 Hz, 6H), 1.26-1.34 (m, 41H), 1.50-1.59 (m, 4H), 1.66 (br s, 4H), 2.82 (dd, J=12.6, 3.0 Hz, 2H), 3.09 (dd, J=12.6, 5.0 Hz, 2H), 3.40-3.46 (m, 4H), 3.76 (dd, J=5.0, 3.0 Hz, 2H).

Example 6

(3R,4R)-3,4-bis((Z)-Hexadec-9-enyloxy)pyrrolidine (Compound 6)

Compound 6 (160 mg, 89.2%) was obtained in the same manner as that in Example 1, by using Compound VI-6 (208 mg, 0.326 mmol) obtained in Reference Example 6.

ESI-MS m/z: 549 (M+H)$^+$; $^1$H-NMR (CDCl$_3$) δ: 0.88 (t, J=6.6 Hz, 6H), 1.27-1.36 (m, 34H), 1.50-1.59 (m, 4H), 1.82 (br s, 3H), 2.01 (q, J=6.2 Hz, 8H), 2.84 (dd, J=12.5, 3.0 Hz, 2H), 3.10 (dd, J=12.5, 5.0 Hz, 2H), 3.43 (t, J=6.8 Hz, 4H), 3.77 (dd, J=5.0, 3.0 Hz, 2H), 5.29-5.40 (m, 4H).

Example 7

(3R,4R)-3,4-bis((Z)-Octadec-6-enyloxy)pyrrolidine (Compound 7)

Compound 7 (123 mg, 82.2%) was obtained in the same manner as that in Example 1, by using Compound VI-7 (171 mg, 0.246 mmol) obtained in Reference Example 7.

ESI-MS m/z: 605 (M+H)$^+$; $^1$H-NMR (CDCl$_3$) δ: 0.88 (t, J=6.6 Hz, 6H), 1.26-1.38 (m, 40H), 1.51-1.61 (m, 4H), 1.64 (s, 5H), 1.97-2.06 (m, 8H), 2.82 (dd, J=12.5, 3.3 Hz, 2H), 3.09 (dd, J=12.5, 5.1 Hz, 2H), 3.41-3.46 (m, 4H), 3.76 (dd, J=4.6, 3.3 Hz, 2H), 5.29-5.41 (m, 4H).

Example 8

(3R,4R)-3,4-bis((11Z,14Z)-Icos-11,14-dienyloxy)pyrrolidine (Compound 8)

Compound 8 (144 mg, 87.5%) was obtained in the same manner as that in Example 1, by using Compound VI-8 (186 mg, 0.249 mmol) obtained in Reference Example 8.

ESI-MS m/z: 657 (M+H)$^+$; $^1$H-NMR (CDCl$_3$) δ: 0.89 (t, J=6.8 Hz, 6H), 1.27-1.40 (m, 36H), 1.50-1.59 (m, 4H), 1.64 (s, 5H), 2.05 (q, J=6.6 Hz, 8H), 2.75-2.85 (m, 6H), 3.09 (dd, J=12.5, 5.0 Hz, 2H), 3.43 (td, J=6.7, 1.3 Hz, 4H), 3.76 (dd, J=5.0, 2.9 Hz, 2H), 5.29-5.43 (m, 8H).

Example 9

(3R,4R)-Pyrrolidine-3,4-diyl di((Z)-octadec-9-enoate) (Compound 9)

Compound 9 (965 mg, 61.6%) was obtained in the same manner as that in Example 1, by using Compound VI-9 (1.79 g, 2.48 mmol) obtained in Reference Example 9.

ESI-MS m/z: 633 (M+H)$^+$; $^1$H-NMR (CDCl$_3$) δ: 0.88 (t, J=6.8 Hz, 6H), 1.27-1.36 (m, 38H), 1.56-1.64 (m, 7H), 2.01 (q, J=5.9 Hz, 8H), 2.30 (t, J=7.6 Hz, 4H), 2.87 (dd, J=13.1, 2.8 Hz, 2H), 3.32 (dd, J=13.1, 5.1 Hz, 2H), 5.09 (dd, J=5.1, 2.8 Hz, 2H), 5.28-5.41 (m, 4H).

Example 10

(3R,4R)-1-Methyl-3,4-bis((9Z,12Z)-octadec-9,12-dienyloxy)pyrrolidine (compound 10)

Compound 1 (4.00 g, 6.67 mmol) obtained in Example 1 was dissolved in 1,2-dichloroethane (50 mL) and methanol (50 mL), and stirred at room temperature for hour after adding formaldehyde (4.96 mL, 66.7 mmol) and sodium triacetoxyborohydride (Acros Organics; 7.06 g, 33.3 mmol). The reaction mixture was further stirred at room temperature for 2.5 hours after adding sodium triacetoxyborohydride (Acros Organics; 7.06 g, 33.3 mmol). The aqueous layer was extracted with ethyl acetate after adding a saturated sodium bicarbonate aqueous solution to the reaction solution. The organic layer was washed with a saturated sodium chloride aqueous solution, dried over anhydrous magnesium sulfate, and concentrated under reduced pressure after filtration. The resulting residue was purified by silica gel column chromatography (chloroform/methanol=100/0 to 95/5) to give compound 10 (3.99 g, 97.4%).

ESI-MS m/z: 615 (M+H)$^+$; $^1$H-NMR (CDCl$_3$) δ: 0.89 (t, J=6.8 Hz, 6H), 1.30-1.41 (m, 30H), 1.52-1.62 (m, 4H), 1.70 (br s, 2H), 2.05 (q, J=6.5 Hz, 8H), 2.31 (s, 3H), 2.47 (dd, J=9.9, 4.0 Hz, 2H), 2.75-2.86 (m, 6H), 3.36-3.49 (m, 4H), 3.81 (dd, J=5.5, 4.5 Hz, 2H), 5.28-5.44 (m, 8H). [Example 11]

(3R,4S)-1-Methyl-3,4-bis((9Z,12Z)-octadec-9,12-dienyloxy)pyrrolidine (Compound 11)

Compound 11 (129 mg, 64.6%) was obtained in the same manner as that in Example 10, by using Compound 3 (194 mg, 0.323 mmol) obtained in Example 3.

ESI-MS m/z: 615 (M+H)$^+$; $^1$H-NMR (CDCl$_3$) δ: 0.89 (t, J=6.8 Hz, 6H), 1.30-1.40 (m, 28H), 1.54-1.62 (m, 4H), 1.76

(br s, 4H), 2.05 (q, J=5.9 Hz, 8H), 2.38 (s, 3H), 2.46-2.51 (m, 2H), 2.77 (t, J=5.9 Hz, 4H), 3.06-3.11 (m, 2H), 3.39-3.55 (m, 4H), 3.90 (t, J=3.8 Hz, 2H), 5.28-5.43 (m, 8H).

Example 12

(3R,4R)-1-Methyl-3,4-bis((Z)-octadec-9-enyloxy) pyrrolidine (Compound 12)

Compound 12 (81.0 mg, 79.4%) was obtained in the same manner as that in Example 10, by using Compound 4 (100 mg, 0.166 mmol) obtained in Example 4.

ESI-MS m/z: 619 (M+H)$^+$; $^1$H-NMR (CDCl$_3$) δ: 0.88 (t, J=6.8 Hz, 6H), 1.23-1.35 (m, 44H), 1.52-1.61 (m, 4H), 2.01 (q, J=5.8 Hz, 8H), 2.31 (s, 3H), 2.46 (dd, J=9.8, 4.4 Hz, 2H), 2.82 (dd, J=9.8, 5.8 Hz, 2H), 3.37-3.48 (m, 4H), 3.81 (t, J=4.4 Hz, 2H), 5.30-5.40 (m, 4H).

Example 13

(3R,4R)-1-Methyl-3,4-bis(tetradecyloxy)pyrrolidine (Compound 13)

Compound 13 (73.6 mg, 96.8%) was obtained in the same manner as that in Example 10, by using Compound 5 (74.0 mg, 0.149 mmol) obtained in Example 5.

ESI-MS m/z: 511 (M+H)$^+$; $^1$H-NMR (CDCl$_3$) δ: 0.88 (t, J=6.8 Hz, 6H), 1.26-1.35 (m, 44H), 1.52-1.61 (m, 4H), 2.31 (s, 3H), 2.47 (dd, J=9.8, 4.2 Hz, 2H), 2.83 (dd, J=9.8, 5.5 Hz, 2H), 3.37-3.48 (m, 4H), 3.81 (dd, J=5.5, 4.2 Hz, 2H).

Example 14

(3R,4R)-3,4-bis((Z)-Hexadec-9-enyloxy)-1-methyl-pyrrolidine (Compound 14)

Compound 14 (107 mg, 97.4%) was obtained in the same manner as that in Example 10, by using Compound 6 (107 mg, 0.195 mmol) obtained in Example 6.

ESI-MS m/z: 563 (M+H)$^+$; $^1$H-NMR (CDCl$_3$) δ: 0.88 (t, J=6.8 Hz, 6H), 1.27-1.38 (m, 34H), 1.52-1.62 (m, 4H), 1.67 (br s, 2H), 2.01 (q, J=6.1 Hz, 8H), 2.32 (s, 3H), 2.47 (dd, J=9.8, 4.4 Hz, 2H), 2.83 (dd, J=9.8, 5.8 Hz, 2H), 3.36-3.49 (m, 4H), 3.81 (t, J=4.4 Hz, 2H), 5.29-5.41 (m, 4H).

Example 15

(3R,4R)-1-Methyl-3,4-bis((Z)-octadec-6-enyloxy) pyrrolidine (Compound 15)

Compound 14 (75.3 mg, 91.8%) was obtained in the same manner as that in Example 10, by using Compound 7 (80.0 mg, 0.132 mmol) obtained in Example 7.

ESI-MS m/z: 619 (M+H)$^+$; $^1$H-NMR (CDCl$_3$) δ: 0.88 (t, J=6.6 Hz, 6H), 1.26-1.41 (m, 44H), 1.53-1.63 (m, 4H), 1.97-2.06 (m, 8H), 2.31 (s, 3H), 2.46 (dd, J=9.6, 4.2 Hz, 2H), 2.82 (dd, J=9.6, 5.6 Hz, 2H), 3.36-3.49 (m, 4H), 3.81 (dd, J=5.6, 4.2 Hz, 2H), 5.28-5.41 (m, 4H).

Example 16

(3R,4R)-3,4-bis((11Z,14Z)-Icos-11,14-dienyloxy)-1-methylpyrrolidine (Compound 16)

Compound 16 (87.4 mg, 95.0%) was obtained in the same manner as that in Example 10, by using Compound 8 (90.0 mg, 0.137 mmol) obtained in Example 8.

ESI-MS m/z: 671 (M+H)$^+$; $^1$H-NMR (CDCl$_3$) δ: 0.89 (t, J=6.8 Hz, 6H), 1.27-1.41 (m, 40H), 1.52-1.61 (m, 4H), 2.05 (q, J=6.5 Hz, 8H), 2.31 (s, 3H), 2.46 (dd, J=10.0, 4.5 Hz, 2H), 2.77 (t, J=5.7 Hz, 4H), 2.82 (dd, J=10.0, 5.7 Hz, 2H), 3.36-3.49 (m, 4H), 3.81 (t, J=4.5 Hz, 2H), 5.28-5.43 (m, 8H).

Example 17

(3R,4R)-1-Ethyl-3,4-bis((9Z,12Z)-octadec-9,12-dienyloxy)pyrrolidine (Compound 17)

Compound 1 (70.0 mg, 0.117 mmol) obtained in Example 1 was dissolved in ethanol (2 mL), and stirred at room temperature for 2 days after adding potassium carbonate (32.2 mg, 0.233 mmol), iodoethane (0.0104 mL, 0.128 mmol). The reaction solution was concentrated under reduced pressure. The resulting residue was purified by silica gel column chromatography (chloroform/methanol=100/0 to 96/4) to give compound 17 (33.3 mg, 45.4%).

ESI-MS m/z: 629 (M+H)$^+$; $^1$H-NMR (CDCl$_3$) δ: 0.89 (t, J=6.9 Hz, 6H), 1.11 (t, J=6.8 Hz, 2H), 1.30-1.38 (m, 29H), 1.55 (br s, 10H), 2.05 (q, J=6.6 Hz, 8H), 2.53 (br s, 2H), 2.77 (t, J=5.6 Hz, 4H), 2.88 (br s, 2H), 3.44 (t, J=6.6 Hz, 4H), 3.83 (t, J=4.6 Hz, 2H), 5.28-5.44 (m, 8H).

Example 18

(3R,4R)-1-Ethyl-3,4-bis((Z)-octadec-9-enyloxy) pyrrolidine (Compound 18)

Compound 18 (13.4 mg, 32.0%) was obtained in the same manner as that in Example 17, by using Compound 4 (40.0 mg, 0.066 mmol) obtained in Example 4.

ESI-MS m/z: 633 (M+H)$^+$; $^1$H-NMR (CDCl$_3$) δ: 0.88 (t, J=6.8 Hz, 6H), 1.08 (t, J=7.1 Hz, 3H), 1.23-1.35 (m, 44H), 1.52-1.59 (m, 4H), 2.01 (q, J=6.2 Hz, 8H), 2.37-2.52 (m, 4H), 2.84 (dd, J=9.5, 6.2 Hz, 2H), 3.41-3.45 (m, 4H), 3.81 (t, J=4.9 Hz, 2H), 5.29-5.40 (m, 4H).

Example 19

(3R,4R)-1,1-Dimethyl-3,4-bis((9Z,12Z)-octadec-9,12-dienyloxy)pyrrolidinium chloride (compound 19)

Iodomethane (1 mL) was added to compound 10 (24.6 mg, 0.0401 mmol) obtained in Example 10, and the mixture was stirred at room temperature for 4 hours. The reaction mixture was concentrated under reduced pressure, and the residue was loaded into an anion-exchange resin (Dowex 1×-200 chloride type; The Dow Chemical Company; 0.5 mL; prewashed with water and methanol), and eluted with methanol. The eluate was concentrated under reduced pressure, and the residue was purified by silica gel column chromatography (methanol/chloroform=0/100 to 25/75) to give compound 19 (24.9 mg, 93.5%).

ESI-MS m/z: 629 M$^+$; $^1$H-NMR (CDCl$_3$) δ: 0.89 (t, J=6.8 Hz, 6H), 1.29 (s, 32H), 1.50-1.57 (m, 4H), 1.58 (s, 4H), 2.05 (q, J=6.7 Hz, 8H), 2.77 (t, J=5.9 Hz, 4H), 3.44-3.57 (m, 4H), 3.67 (s, 6H), 3.86 (dd, J=13.4, 3.8 Hz, 2H), 4.04-4.13 (m, 4H), 5.29-5.42 (m, 8H).

Example 20

(3R,4R)-1,1-Dimethyl-3,4-bis((9Z,12Z)-octadec-9,12-dienoyloxy)pyrrolidinium chloride (compound 20)

Compound 20 (1.21 g, 96.4%) was obtained in the same manner as that in Example 19, by using compound A-3 (1.16 g, 1.81 mmol) obtained in Reference Example 30.

ESI-MS m/z: 657 M+; $^1$H-NMR (CDCl$_3$) δ: 0.89 (t, J=6.8 Hz, 6H), 1.29-1.38 (m, 26H), 1.57-1.67 (m, 4H), 1.78 (s, 2H), 2.05 (q, J=6.6 Hz, 8H), 2.39 (t, J=7.6 Hz, 4H), 2.77 (t, J=5.8 Hz, 4H), 3.78 (s, 6H), 4.15 (dd, J=14.0, 3.0 Hz, 2H), 4.38 (dd, J=14.0, 5.8 Hz, 2H), 5.27-5.46 (m, 10H).

Example 21

(3R,4S)-1,1-Dimethyl-3,4-bis((9Z,12Z)-octadec-9,12-dienyloxy)pyrrolidinium chloride (compound 21)

Compound 21 (62.8 mg, 76.6%) was obtained in the same manner as that in Example 19, by using compound 11 (76.0 mg, 0.124 mmol) obtained in Example 11.

ESI-MS m/z: 629 M+; $^1$H-NMR (CDCl$_3$) δ: 0.89 (t, J=6.7 Hz, 6H), 1.23-1.41 (m, 30H), 1.52-1.61 (m, 4H), 1.93-2.17 (m, 2H), 2.05 (q, J=6.7 Hz, 8H), 2.77 (t, J=5.8 Hz, 4H), 3.41 (s, 3H), 3.47-3.64 (m, 9H), 4.43-4.50 (m, 2H), 4.58 (br s, 2H), 5.28-5.44 (m, 8H).

Example 22

(3R,4R)-1,1-Dimethyl-3,4-bis((Z)-octadec-9-enyloxy)pyrrolidinium chloride (compound 22)

Compound 4 (135 mg, 0.223 mmol) obtained in Example 4 was dissolved in methanol (2 mL), and stirred overnight at room temperature after adding potassium carbonate (154 mg, 1.12 mmol), and iodomethane (0.699 mL, 11.2 mmol). The reaction solution was concentrated under reduced pressure, and the residue was loaded into an anion-exchange resin (Dowex 1x-200 chloride type; The Dow Chemical Company; 1 mL; prewashed with water and methanol), and eluted with methanol. The eluate was concentrated under reduced pressure, and the residue was purified by silica gel column chromatography (methanol/chloroform=0/100 to 70/30) to give compound 22 (27.8 mg, 18.6%).

ESI-MS m/z: 633 M+; $^1$H-NMR (CDCl$_3$) δ: 0.88 (t, J=6.8 Hz, 6H), 1.26-1.36 (m, 40H), 1.50-1.59 (m, 4H), 1.62 (s, 4H), 2.01 (q, J=5.9 Hz, 8H), 3.44-3.58 (m, 4H), 3.66 (s, 6H), 3.86 (dd, J=13.2, 4.0 Hz, 2H), 4.02-4.13 (m, 4H), 5.29-5.41 (m, 4H).

Example 23

(3R,4R)-1,1-Dimethyl-3,4-bis((Z)-octadec-9-enoyloxy)pyrrolidinium chloride (compound 23)

Compound 23 (442 mg, 95.2%) was obtained in the same manner as that in Example 19, by using compound A-4 (430 mg, 0.666 mmol) obtained in Reference Example 31.

ESI-MS m/z: 661 M+; $^1$H-NMR (CDCl$_3$) δ: 0.88 (t, J=6.6 Hz, 6H), 1.26-1.35 (m, 38H), 1.58-1.67 (m, 4H), 1.76 (br s, 2H), 2.01 (q, J=5.1 Hz, 8H), 2.38 (t, J=7.5 Hz, 4H), 3.78 (s, 6H), 4.15 (dd, J=13.6, 2.6 Hz, 2H), 4.37 (dd, J=13.6, 5.7 Hz, 2H), 5.29-5.40 (m, 4H), 5.43-5.46 (m, 2H).

Example 24

3-((3R,4R)-3,4-bis((9Z,12Z)-Octadec-9,12-dienyloxy)pyrrolidin-1-yl) propane-1,2-diol (compound 24)

Compound 1 (100 mg, 0.167 mmol) obtained in Example 1 was dissolved in 1-propanol (1 mL), and irradiated with microwave (300 W, 100° C., 2 hours) after adding glycidol (0.111 mL, 1.67 mmol). The reaction solution was concentrated under reduced pressure after adding water. The resulting residue was purified by silica gel column chromatography (chloroform/methanol=100/0 to 87/13) to give compound 24 (30.4 mg, 27.1%).

ESI-MS m/z: 675 (M+H)+; $^1$H-NMR (CDCl$_3$) δ: 0.89 (t, J=6.9 Hz, 3. OH), 0.93 (t, J=7.3 Hz, 3. OH), 1.26-1.38 (m, 22. OH), 1.51-1.67 (m, 8. OH), 2.05 (q, J=6.4 Hz, 8. OH), 2.33-2.42 (m, 1. OH), 2.54 (dd, J=10.2, 4.3 Hz, 1. OH), 2.66-2.90 (m, 7. OH), 3.04 (dd, J=9.9, 5.9 Hz, 1. OH), 3.40-3.58 (m, 9.5H), 3.63-3.88 (m, 7.5H), 5.28-5.44 (m, 8. OH).

Example 25

(3R,4R)-1-(2-(Dimethylamino) acetyl)-3,4-bis((9Z,12Z)-octadec-9,12-dienyloxy)pyrrolidine (compound 25)

Compound 1 (100 mg, 0.167 mmol) obtained in Example 1 was dissolved in chloroform (2 mL), and stirred at room temperature for 1.5 hours after adding N,N-dimethylglycine hydrochloride (Tokyo Chemical Industry Co.; 46.5 mg, 0.333 mmol), diisopropylethylamine (0.146 mL, 0.833 mmol), and (benzotriazol-1-yloxy)tripyrrolizinophosphonium hexafluorophosphate (Watanabe Chemical Industries, Ltd.; 217 mg, 0.417 mmol). The aqueous layer was extracted with chloroform after adding a saturated sodium bicarbonate aqueous solution to the reaction mixture. The organic layer was washed with a saturated sodium chloride aqueous solution, dried over anhydrous magnesium sulfate, and concentrated under reduced pressure after filtration. The resulting residue was purified by silica gel column chromatography (chloroform/methanol=100/0 to 95/5) to give compound 25 (98.9 mg, 86.8%).

ESI-MS m/z: 686 (M+H)+; $^1$H-NMR (CDCl$_3$) δ: 0.89 (t, J=6.8 Hz, 6H), 1.29-1.41 (m, 32H), 1.49-1.57 (m, 4H), 2.05 (q, J=6.5 Hz, 8H), 2.31 (s, 6H), 2.77 (t, J=5.8 Hz, 4H), 3.06 (s, 2H), 3.37-3.70 (m, 8H), 3.84-3.91 (m, 2H), 5.28-5.43 (m, 8H).

Example 26

(3R,4R)-1-(2-(Dimethylamino) acetyl)pyrrolidine-3,4-diyl di((9Z,12Z)-octadec-9,12-dienoate) (compound 26)

Compound 26 (297 mg, 87.2%) was obtained in the same manner as that in Example 25, by using compound 2 (300 mg, 0.478 mmol) obtained in Example 2, and N,N-dimethylglycine hydrochloride (Tokyo Chemical Industry Co., Ltd.; 133 mg, 0.955 mmol).

ESI-MS m/z: 714 (M+H)+; $^1$H-NMR (CDCl$_3$) δ: 0.89 (t, J=6.8 Hz, 6H), 1.29-1.40 (m, 28H), 1.56-1.64 (m, 4H), 2.05 (q, J=6.6 Hz, 8H), 2.27-2.35 (m, 10H), 2.77 (t, J=5.7 Hz, 4H), 3.06 (s, 2H), 3.66-3.91 (m, 4H), 5.18 (d, J=4.0 Hz, 2H), 5.28-5.43 (m, 8H).

Example 27

(3R,4R)-1-(2-(Dimethylamino) acetyl)pyrrolidine-3, 4-diyl di((Z)-octadec-9-enoate) (Compound 27)

Compound 27 (210 mg, 92.5%) was obtained in the same manner as that in Example 25, by using compound 9 (200 mg, 0.316 mmol) obtained in Example 9 and N,N-dimethylglycine hydrochloride (Tokyo Chemical Industry Co., Ltd.; 88 mg, 0.633 mmol).

ESI-MS m/z: 718 (M+H)$^+$; $^1$H-NMR (CDCl$_3$) δ: 0.88 (t, J=6.8 Hz, 6H), 1.27-1.35 (m, 40H), 1.56-1.64 (m, 4H), 2.01 (q, J=6.2 Hz, 8H), 2.27-2.34 (m, 10H), 3.06 (s, 2H), 3.66-3.91 (m, 4H), 5.18 (d, J=3.7 Hz, 2H), 5.34 (tt, J=11.2, 4.6 Hz, 4H).

Example 28

(3R,4R)-1-(3-(Dimethylamino) propanoyl)-3,4-bis((9Z,12Z)-octadec-9,12-dienyloxy)pyrrolidine (Compound 28)

Compound 28 (43.2 mg, 58.8%) was obtained in the same manner as that in Example 25, by using compound 1 (63.0 mg, 0.105 mmol) obtained in Example 1 and 3-(dimethylamino)propionic acid (MATRIX Scientific; 24.6 mg, 0.210 mmol).

ESI-MS m/z: 700 (M+H)$^+$; $^1$H-NMR (CDCl$_3$) δ: 0.89 (t, J=6.8 Hz, 6H), 1.28-1.38 (m, 32H), 1.48-1.57 (m, 4H), 2.05 (q, J=6.5 Hz, 8H), 2.75-2.85 (m, 6H), 2.95 (s, 6H), 3.42-3.53 (m, 8H), 3.59-3.66 (m, 2H), 3.86-3.95 (m, 2H), 5.28-5.44 (m, 8H).

Example 29

(3R,4R)-1-(3-(dimethylamino) propanoyl)pyrrolidine-3,4-diyl di((9Z,12Z)-octadec-9,12-dienoate) (Compound 29)

Compound 29 (57.6 mg, 82.9%) was obtained in the same manner as that in Example 25, by using compound 2 (60.0 mg, 0.096 mmol) obtained in Example 2 and 3-(dimethylamino)propionic acid (MATRIX Scientific; 22.4 mg, 0.191 mmol).

ESI-MS m/z: 728 (M+H)$^+$; $^1$H-NMR (CDCl$_3$) δ: 0.89 (t, J=7.0 Hz, 6H), 1.26-1.40 (m, 28H), 1.55-1.63 (m, 4H), 2.05 (q, J=6.7 Hz, 8H), 2.27-2.34 (m, 10H), 2.44 (t, J=7.4 Hz, 2H), 2.68 (t, J=7.4 Hz, 2H), 2.77 (t, J=5.7 Hz, 4H), 3.55 (d, J=12.1 Hz, 1H), 3.64-3.78 (m, 2H), 3.82 (dd, J=12.1, 4.0 Hz, 1H), 5.18 (d, J=4.0 Hz, 2H), 5.28-5.43 (m, 8H).

Example 30

(3R,4R)-1-(3-(Dimethylamino) propanoyl)pyrrolidine-3,4-diyl di((Z)-octadec-9-enoate) (Compound 30)

Compound 35 (209 mg, 90.3%) was obtained in the same manner as that in Example 25, by using compound 9 (200 mg, 0.316 mmol) obtained in Example 9 and 3-(dimethylamino)propionic acid (MATRIX Scientific; 74.1 mg, 0.633 mmol).

ESI-MS m/z: 732 (M+H)$^+$; $^1$H-NMR (CDCl$_3$) δ: 0.88 (t, J=6.8 Hz, 6H), 1.27-1.35 (m, 38H), 1.56-1.65 (m, 4H), 1.74 (br s, 2H), 2.01 (q, J=5.5 Hz, 8H), 2.28-2.34 (m, 10H), 2.46 (t, J=7.3 Hz, 2H), 2.72 (t, J=7.3 Hz, 2H), 3.55 (d, J=12.1 Hz, 1H), 3.67-3.85 (m, 3H), 5.19 (d, J=3.7 Hz, 2H), 5.29-5.40 (m, 4H).

Example 31

(3R,4R)-1-((S)-2,6-Diaminohexanoyl)-3,4-bis((9Z,12Z)-octadec-9,12-dienyloxy)pyrrolidine (compound 31)

Nε-(tert-Butoxycarbonyl)-Nα-[(9H-fluoren-9-ylmethoxy)carbonyl]-L-lysine (Tokyo Chemical Industry Co., Ltd.; 125 mg, 0.267 mmol), and (benzotriazol-1-yloxy)tripyrrolizinophosphonium hexafluorophosphate (Watanabe Chemical Industries, Ltd.; 146 mg, 0.280 mmol) were dissolved in chloroform (1 mL), and stirred at room temperature for 1 hour. A chloroform (2 mL) solution of compound 1 (80.0 mg, 0.133 mmol) obtained in Example 1 was added to the reaction solution, and the mixture was stirred at room temperature for 7 hours. The reaction mixture was stirred overnight at room temperature after adding Nε-(tert-butoxycarbonyl)-Nα-[(9H-fluoren-9-ylmethoxy)carbonyl]-L-lysine (Tokyo Chemical Industry Co., Ltd.; 187 mg, 0.400 mmol), and (benzotriazol-1-yloxy)tripyrrolizinophosphonium hexafluorophosphate (Watanabe Chemical Industries, Ltd.; 222 mg, 0.427 mmol). The reaction mixture was further stirred overnight at room temperature, and at 80° C. for 3 hours after adding Nε-(tert-butoxycarbonyl)-Nα-[(9H-fluoren-9-ylmethoxy)carbonyl]-L-lysine (Tokyo Chemical Industry Co., Ltd.; 156 mg, 0.333 mmol), and O-(7-azabenzotriazol-1-yl)-N,N,N',N'-tetramethyluronium hexafluorophosphate (Aldrich; 152 mg, 0.400 mmol). A saturated sodium bicarbonate aqueous solution was added after cooling the mixture to room temperature, and the aqueous layer was extracted with ethyl acetate. The organic layer was washed with a saturated sodium chloride aqueous solution, dried over anhydrous magnesium sulfate, and concentrated under reduced pressure after filtration. The resulting residue was then passed through a silica gel pad to give a crude product of (5S)-5-(((9H-fluoren-9-yl) methoxy)carbonylamino)-6-(3,4-bis((9Z,12Z)-octadec-9,12-dienyloxy)pyrrolidin-1-yl)-6-oxohexylcarbamic acid tert-butyl ester.

The resulting crude product was dissolved in dichloromethane (2 mL), and the solution was stirred at room temperature for 4 hours after adding trifluoroacetic acid (0.103 mL, 1.33 mmol). The reaction mixture was stirred at room temperature for 4.5 hours after adding trifluoroacetic acid (0.205 mL, 2.67 mmol). The aqueous layer was extracted with chloroform after adding a saturated sodium bicarbonate aqueous solution to the reaction solution. The organic layer was washed with a saturated sodium chloride aqueous solution, dried over anhydrous magnesium sulfate, and concentrated under reduced pressure after filtration. The resulting residue was purified by silica gel column chromatography (chloroform/methanol=100/0 to 87/13) to give (9H-fluoren-9-yl)methyl(2S)-6-amino-1-(3,4-bis((9Z,12Z)-octadec-9,12-dienyloxy)pyrrolidin-1-yl)-1-oxohexan-2-yl carbamate (66.1 mg, 52.2% in 2 steps).

The resulting (9H-fluoren-9-yl)methyl(2S)-6-amino-1-(3,4-bis((9Z,12Z)-octadec-9,12-dienyloxy)pyrrolidin-1-yl)-1-oxohexan-2-yl carbamate (65 mg, 0.068 mmol) was dissolved in tetrahydrofuran (2 mL), and stirred at room temperature for 5 hours after adding pyrrolidine (0.5 mL). The reaction mixture was concentrated under reduced pressure, and the resulting residue was purified by silica gel column chromatography (chloroform/methanol=100/0 to 60/40) to give compound 31 (24.0 mg, 48.2%).

ESI-MS m/z: 729 (M+H)$^+$; $^1$H-NMR (CDCl$_3$) δ: 0.89 (t, J=6.9 Hz, 6H), 1.26-1.38 (m, 32H), 1.50-1.74 (m, 10H), 2.05 (q, J=6.5 Hz, 8H), 2.77 (t, J=5.8 Hz, 4H), 3.01 (br s, 2H), 3.32-3.72 (m, 8H), 3.86 (br s, 2H), 3.93 (br s, 1H), 5.28-5.43 (m, 8H).

Example 32

N-Methyl-N,N-bis(2-((9Z,12Z)-octadec-9,12-dienyloxy)ethyl)amine (Compound 32)

Compound 32 (68.3 mg, 11.1%) was obtained in the same manner as that in Reference Example 1, by using N-methyldiethanolamine (Tokyo Chemical Industry Co., Ltd.; 119 mg, 0.999 mmol) and (9Z,12Z)-octadec-9,12-dienyl methanesulfonate (Nu-Chek Prep, Inc; 861 mg, 2.50 mmol).

ESI-MS m/z: 617 (M+H)$^+$; $^1$H-NMR (CDCl$_3$) δ: 0.89 (t, J=6.9 Hz, 6H), 1.29 (br s, 32H), 1.50-1.61 (m, 4H), 2.00-2.09 (m, 8H), 2.33 (s, 3H), 2.64 (t, J=6.1 Hz, 4H), 2.77 (t, J=5.6 Hz, 4H), 3.41 (t, J=6.8 Hz, 4H), 3.52 (t, J=6.1 Hz, 4H), 5.27-5.44 (m, 8H).

Example 33

N-Methyl-N,N-bis(2-((Z)-octadec-9-enyloxy)ethyl)amine (Compound 33)

Compound 33 (156 mg, 25.2%) was obtained in the same manner as that in Reference Example 1, by using N-methyldiethanolamine (Tokyo Chemical Industry Co., Ltd.; 119 mg, 0.999 mmol) and (Z)-octadec-9-enyl methanesulfonate (Nu-Chek Prep, Inc; 865 mg, 2.50 mmol).

ESI-MS m/z: 621 (M+H)$^+$; $^1$H-NMR (CDCl$_3$) δ: 0.88 (t, J=6.6 Hz, 6H), 1.25-1.34 (m, 44H), 1.51-1.60 (m, 4H), 1.97-2.04 (m, 8H), 2.33 (s, 3H), 2.63 (t, J=6.1 Hz, 4H), 3.41 (t, J=6.8 Hz, 4H), 3.52 (t, J=6.1 Hz, 4H), 5.28-5.40 (m, 4H).

Example 34

N-Methyl-N,N-bis(2-(tetradecyloxy)ethyl)amine (Compound 34)

Compound 34 (99.3 mg, 0.194 mmol) was obtained in the same manner as that in Reference Example 1, by using N-methyldiethanolamine (Tokyo Chemical Industry Co., Ltd.; 119 mg, 0.999 mmol) and tetradecyl methanesulfonate (Nu-Chek Prep, Inc; 731 mg, 2.50 mmol).

ESI-MS m/z: 513 (M+H)$^+$; $^1$H-NMR (CDCl$_3$) δ: 0.88 (t, J=6.8 Hz, 6H), 1.26 (br s, 44H), 1.51-1.60 (m, 4H), 2.33 (s, 3H), 2.64 (t, J=6.1 Hz, 4H), 3.41 (t, J=6.8 Hz, 4H), 3.52 (t, J=5.9 Hz, 4H).

Example 35

N-Methyl-N,N-bis(2-((Z)-hexadec-9-enyloxy)ethyl)amine (Compound 35)

Compound 35 (199 mg, 50.9%) was obtained in the same manner as that in Reference Example 1, by using N-methyldiethanolamine (Tokyo Chemical Industry Co., Ltd.; 82.6 mg, 0.693 mmol) and (Z)-hexadec-9-enyl methanesulfonate (Nu-Chek Prep, Inc; 530 mg, 1.66 mmol).

ESI-MS m/z: 565 (M+H)$^+$; $^1$H-NMR (CDCl$_3$) δ: 0.88 (t, J=6.8 Hz, 6H), 1.29 (br s, 36H), 1.51-1.56 (m, 4H), 1.97-2.04 (m, 8H), 2.33 (s, 3H), 2.64 (t, J=6.1 Hz, 4H), 3.41 (t, J=6.8 Hz, 4H), 3.52 (t, J=6.1 Hz, 4H), 5.28-5.40 (m, 4H).

Example 36

N-Methyl-N,N-bis(2-((Z)-octadec-6-enyloxy)ethyl)amine (Compound 36)

Compound 36 (205 mg, 59.4%) was obtained in the same manner as that in Reference Example 1, by using N-methyldiethanolamine (Tokyo Chemical Industry Co., Ltd.; 66.3 mg, 0.557 mmol) and (Z)-octadec-6-enyl methanesulfonate (Nu-Chek Prep, Inc; 463 mg, 1.34 mmol).

ESI-MS m/z: 621 (M+H)$^+$; $^1$H-NMR (CDCl$_3$) δ: 0.88 (t, J=6.6 Hz, 6H), 1.24-1.37 (m, 44H), 1.52-1.63 (m, 4H), 1.97-2.06 (m, 8H), 2.33 (s, 3H), 2.64 (t, J=6.1 Hz, 4H), 3.41 (t, J=6.6 Hz, 4H), 3.52 (t, J=6.1 Hz, 4H), 5.29-5.40 (m, 4H).

Example 37

N-Methyl-N,N-bis(2-(octadecyloxy)ethyl)amine (Compound 37)

Compound 37 (218 mg, 23.3%) was obtained in the same manner as that in Reference Example 5, by using N-methyldiethanolamine (Tokyo Chemical Industry Co., Ltd.; 179 mg, 1.50 mmol) and 1-bromooctadecane (Tokyo Chemical Industry Co., Ltd.; 1.20 g, 3.60 mmol).

ESI-MS m/z: 625 (M+H)$^+$; $^1$H-NMR (CDCl$_3$) δ: 0.88 (t, J=6.6 Hz, 6H), 1.26 (s, 60H), 1.51-1.60 (m, 4H), 2.33 (s, 3H), 2.64 (t, J=6.1 Hz, 4H), 3.41 (t, J=6.6 Hz, 4H), 3.52 (t, J=6.1 Hz, 4H).

Example 38

(3R,4R)-3,4-bis(Hexadecyloxy)pyrrolidine (Compound 38)

Compound 38 (210 mg, 84.8%) was obtained in the same manner as that in Example 1, by using Compound VI-11 (288 mg, 0.449 mmol) obtained in Reference Example 11.

ESI-MS m/z: 553 (M+H)$^+$; $^1$H-NMR (CDCl$_3$) δ: 0.88 (t, J=6.6 Hz, 6H), 1.26-1.34 (m, 50H), 1.50-1.59 (m, 4H), 1.66-1.68 (m, 3H), 2.82 (dd, J=12.5, 3.0 Hz, 2H), 3.09 (dd, J=12.5, 5.0 Hz, 2H), 3.43 (td, J=6.6, 0.7 Hz, 4H), 3.76 (dd, J=5.0, 3.0 Hz, 2H).

Example 39

(3R,4R)-3,4-bis(Octadecyloxy)pyrrolidine (Compound 39)

Compound 39 (209 mg, 82.6%) was obtained in the same manner as that in Example 1, by using Compound VI-12 (290 mg, 0.415 mmol) obtained in Reference Example 12.

ESI-MS m/z: 609 (M+H)$^+$; $^1$H-NMR (CDCl$_3$) δ: 0.88 (t, J=6.6 Hz, 6H), 1.26-1.34 (m, 58H), 1.50-1.59 (m, 4H), 1.64 (br s, 3H), 2.82 (dd, J=12.3, 3.1 Hz, 2H), 3.09 (dd, J=12.3, 5.0 Hz, 2H), 3.43 (t, J=6.6 Hz, 4H), 3.77 (dd, J=5.0, 3.1 Hz, 2H).

Example 40

(3R,4R)-3,4-bis((Z)-Tetradec-9-enyloxy)pyrrolidine (Compound 40)

Compound 40 (71.4 mg, 84.0%) was obtained in the same manner as that in Example 1, by using Compound VI-13 (100 mg, 0.172 mmol) obtained in Reference Example 13.

ESI-MS m/z: 492 (M+H)$^+$; $^1$H-NMR (CDCl$_3$) δ: 0.87-0.92 (m, 6H), 1.29-1.35 (m, 26H), 1.50-1.59 (m, 4H), 1.64 (br s, 3H), 2.02 (q, J=5.9 Hz, 8H), 2.82 (dd, J=12.5, 2.9 Hz, 2H), 3.09 (dd, J=12.5, 4.9 Hz, 2H), 3.37-3.49 (m, 4H), 3.76 (dd, J=4.9, 2.9 Hz, 2H), 5.30-5.40 (m, 4H).

Example 41

(3R,4R)-3,4-bis((Z)-Octadec-11-enyloxy)pyrrolidine (Compound 41)

Compound 41 (157 mg, 82.0%) was obtained in the same manner as that in Example 1, by using Compound VI-14 (220 mg, 0.317 mmol) obtained in Reference Example 14.

ESI-MS m/z: 605 (M+H)$^+$; $^1$H-NMR (CDCl$_3$) δ: 0.88 (t, J=6.8 Hz, 6H), 1.27-1.37 (m, 42H), 1.50-1.59 (m, 4H), 1.87 (br s, 2H), 2.01 (q, J=6.1 Hz, 8H), 2.83 (dd, J=12.5, 2.9 Hz, 2H), 3.10 (dd, J=12.5, 5.0 Hz, 2H), 3.43 (t, J=6.8 Hz, 4H), 3.77 (dd, J=5.0, 2.9 Hz, 2H), 5.30-5.40 (m, 4H).

Example 42

(3R,4R)-3,4-bis((Z)-Icos-11-enyloxy)pyrrolidine (Compound 42)

Compound 42 (168 mg, 84.6%) was obtained in the same manner as that in Example 1, by using Compound VI-15 (225 mg, 0.300 mmol) obtained in Reference Example 15.

ESI-MS m/z: 661 (M+H)$^+$; $^1$H-NMR (CDCl$_3$) δ: 0.88 (t, J=6.8 Hz, 6H), 1.27-1.36 (m, 50H), 1.50-1.59 (m, 4H), 1.78 (br s, 2H), 2.01 (q, J=6.2 Hz, 8H), 2.82 (dd, J=12.5, 2.9 Hz, 2H), 3.09 (dd, J=12.5, 5.0 Hz, 2H), 3.43 (td, J=6.7, 0.9 Hz, 4H), 3.76 (dd, J=5.0, 2.9 Hz, 2H), 5.30-5.40 (m, 4H).

Example 43

(3S,4S)-3,4-bis((9Z,12Z)-Octadec-9,12-dienyloxy)pyrrolidine (Compound 43)

Compound 43 (728 mg, 90.1%) was obtained in the same manner as that in Example 1, by using Compound VI-10 (929 mg, 1.35 mmol) obtained in Reference Example 10.

ESI-MS m/z: 601 (M+H)$^+$; $^1$H-NMR (CDCl$_3$) δ: 0.89 (t, J=6.9 Hz, 6H), 1.30-1.41 (m, 30H), 1.50-1.60 (m, 4H), 1.65 (br s, 3H), 2.05 (q, J=6.6 Hz, 8H), 2.75-2.85 (m, 6H), 3.09 (dd, J=12.5, 5.3 Hz, 2H), 3.43 (t, J=6.6 Hz, 4H), 3.75-3.78 (m, 2H), 5.28-5.43 (m, 8H).

Example 44 trans-3,4-bis(((Z)-Hexadec-9-enyloxy)methyl)pyrrolidine (Compound 44)

Compound 44 (260 mg, 89.7%) was obtained in the same manner as that in Example 1, by using Compound VI-16 (335 mg, 0.503 mmol) obtained in Reference Example 17.

ESI-MS m/z: 577 (M+H)$^+$; $^1$H-NMR (CDCl$_3$) δ: 0.88 (t, J=6.8 Hz, 6H), 1.29-1.35 (m, 36H), 1.50-1.59 (m, 4H), 1.96-2.07 (m, 10H), 2.70 (dd, J=11.1, 5.7 Hz, 2H), 3.06 (dd, J=11.1, 7.3 Hz, 2H), 3.28-3.46 (m, 8H), 5.30-5.40 (m, 4H).

Example 45

(3R,4R)-3,4-bis(Hexadecyloxy)-1-methylpyrrolidine (Compound 45)

Compound 45 (182 mg) was obtained in the same manner as that in Example 10, by using Compound 38 (175 mg, 0.317 mmol) obtained in Example 38.

ESI-MS m/z: 567 (M+H)$^+$; $^1$H-NMR (CDCl$_3$) δ: 0.88 (t, J=6.6 Hz, 6H), 1.26-1.35 (m, 52H), 1.52-1.61 (m, 4H), 2.31 (s, 3H), 2.46 (dd, J=9.6, 4.3 Hz, 2H), 2.82 (dd, J=9.6, 5.5 Hz, 2H), 3.37-3.48 (m, 4H), 3.81 (dd, J=5.5, 4.3 Hz, 2H).

Example 46

(3R,4R)-1-Methyl-3,4-bis(octadecyloxy)pyrrolidine (Compound 46)

Compound 46 (169 mg, 95.0%) was obtained in the same manner as that in Example 10, by using Compound 39 (174 mg, 0.286 mmol) obtained in Example 39.

ESI-MS m/z: 623 (M+H)$^+$; $^1$H-NMR (CDCl$_3$) δ: 0.88 (t, J=6.6 Hz, 6H), 1.26-1.35 (m, 60H), 1.52-1.61 (m, 4H), 2.31 (s, 3H), 2.46 (dd, J=9.9, 4.3 Hz, 2H), 2.82 (dd, J=9.9, 5.6 Hz, 2H), 3.37-3.48 (m, 4H), 3.81 (dd, J=5.6, 4.3 Hz, 2H).

Example 47

(3R,4R)-1-Methyl-3,4-bis((Z)-tetradec-9-enyloxy)pyrrolidine (Compound 47)

Compound 47 (53.4 mg, 93.6%) was obtained in the same manner as that in Example 10, by using Compound 40 (55 mg, 0.112 mmol) obtained in Example 40.

ESI-MS m/z: 507 (M+H)$^+$; $^1$H-NMR (CDCl$_3$) δ: 0.87-0.92 (m, 6H), 1.26-1.35 (m, 28H), 1.52-1.61 (m, 4H), 1.98-2.05 (m, 8H), 2.31 (s, 3H), 2.46 (dd, J=9.9, 4.2 Hz, 2H), 2.82 (dd, J=9.9, 5.6 Hz, 2H), 3.37-3.48 (m, 4H), 3.81 (dd, J=5.6, 4.2 Hz, 2H), 5.30-5.40 (m, 4H).

Example 48

(3R,4R)-1-Methyl-3,4-bis((Z)-octadec-11-enyloxy)pyrrolidine (Compound 48)

Compound 48 (125 mg, 94.3%) was obtained in the same manner as that in Example 10, by using Compound 41 (130 mg, 0.215 mmol) obtained in Example 41.

ESI-MS m/z: 619 (M+H)$^+$; $^1$H-NMR (CDCl$_3$) δ: 0.88 (t, J=6.8 Hz, 6H), 1.27-1.36 (m, 44H), 1.52-1.61 (m, 4H), 2.01 (q, J=6.1 Hz, 8H), 2.31 (s, 3H), 2.46 (dd, J=9.9, 4.0 Hz, 2H), 2.82 (dd, J=9.9, 5.9 Hz, 2H), 3.37-3.48 (m, 4H), 3.81 (t, J=4.9 Hz, 2H), 5.30-5.40 (m, 4H).

Example 49

(3R,4R)-3,4-bis((Z)-Icos-11-enyloxy)-1-methylpyrrolidine (Compound 49)

Compound 49 (132 mg, 91.7%) was obtained in the same manner as that in Example 10, by using Compound 42 (141 mg, 0.214 mmol) obtained in Example 42.

ESI-MS m/z: 675 (M+H)$^+$; $^1$H-NMR (CDCl$_3$) δ: 0.88 (t, J=6.8 Hz, 6H), 1.27-1.36 (m, 52H), 1.52-1.61 (m, 4H), 2.01 (q, J=6.1 Hz, 8H), 2.31 (s, 3H), 2.46 (dd, J=10.0, 4.2 Hz, 2H), 2.82 (dd, J=10.0, 5.9 Hz, 2H), 3.37-3.48 (m, 4H), 3.81 (t, J=4.8 Hz, 2H), 5.30-5.40 (m, 4H).

Example 50

(3S,4S)-1-Methyl-3,4-bis((9Z,12Z)-octadec-9,12-dienyloxy)pyrrolidine (Compound 50)

Compound 50 (330 mg, 99.2%) was obtained in the same manner as that in Example 10, by using Compound 43 (325 mg, 0.542 mmol) obtained in Example 43.

ESI-MS m/z: 615 (M+H)⁺; ¹H-NMR (CDCl₃) δ: 0.89 (t, J=6.7 Hz, 6H), 1.29-1.38 (m, 30H), 1.51-1.62 (m, 4H), 1.71 (br s, 2H), 2.05 (q, J=6.5 Hz, 8H), 2.31 (s, 3H), 2.46 (dd, J=10.0, 4.5 Hz, 2H), 2.75-2.86 (m, 6H), 3.36-3.49 (m, 4H), 3.81 (t, J=4.5 Hz, 2H), 5.28-5.43 (m, 8H).

Example 51 trans-3,4-bis(((Z)-Hexadec-9-enyloxy)methyl)-1-methylpyrrolidine (Compound 51)

Compound 51 (174 mg, 97.1%) was obtained in the same manner as that in Example 10, by using Compound 44 (175 mg, 0.304 mmol) obtained in Example 44.

ESI-MS m/z: 591 (M+H)⁺; ¹H-NMR (CDCl₃) δ: 0.88 (t, J=6.8 Hz, 6H), 1.26-1.35 (m, 36H), 1.50-1.59 (m, 4H), 1.98-2.11 (m, 10H), 2.33 (s, 3H), 2.39 (dd, J=9.2, 5.3 Hz, 2H), 2.67 (dd, J=9.2, 7.3 Hz, 2H), 3.31-3.45 (m, 8H), 5.30-5.40 (m, 4H).

Example 52

(3S,4S)-1,1-Dimethyl-3,4-bis((9Z,12Z)-octadec-9,12-dienyloxy)pyrrolidinium chloride (Compound 52)

Compound 52 (135 mg, 99.8%) was obtained in the same manner as that in Example 19, by using Compound 50 (125 mg, 0.204 mmol) obtained in Example 50.

ESI-MS m/z: 629 M⁺; ¹H-NMR (CDCl₃) δ: 0.89 (t, J=6.7 Hz, 6H), 1.29-1.38 (m, 30H), 1.50-1.59 (m, 4H), 1.72 (br s, 2H), 2.05 (q, J=6.5 Hz, 8H), 2.77 (t, J=5.9 Hz, 4H), 3.43-3.57 (m, 4H), 3.68 (s, 6H), 3.87 (dd, J=13.2, 3.6 Hz, 2H), 4.03-4.13 (m, 4H), 5.28-5.44 (m, 8H).

Example 53

(3R,4R)-1-(2,3-diHydroxypropyl)pyrrolidine-3,4-diyl di((9Z,12Z)-octadec-9,12-enoate) (Compound 53)

Compound 53 (95.4 mg, 85.2%) was obtained in the same manner as that in Example 10, by using Compound 2 (100 mg, 0.159 mmol) obtained in Example 2 and DL-2,3-dihydroxypropanal (Aldrich; 143 mg, 1.59 mmol).

ESI-MS m/z: 703 (M+H)⁺; ¹H-NMR (CDCl₃) δ: 0.89 (t, J=6.8 Hz, 6H), 1.25-1.40 (m, 28H), 1.56-1.66 (m, 4H), 2.05 (q, J=6.7 Hz, 8H), 2.31 (t, J=7.5 Hz, 4H), 2.39-2.48 (m, 1H), 2.56 (dd, J=10.8, 3.8 Hz, 1H), 2.67-2.85 (m, 6H), 3.09 (dd, J=10.3, 5.9 Hz, 1H), 3.24 (dd, J=10.3, 5.9 Hz, 1H), 3.50-3.56 (m, 1H), 3.72-3.80 (m, 2H), 5.11 (dd, J=8.8, 5.1 Hz, 2H), 5.28-5.43 (m, 8H).

Example 54

1-((3R,4R)-3,4-bis((9Z,12Z)-Octadec-9,12-dienyloxy)pyrrolidine-1-yl)propan-2-ol (Compound 54)

Compound 54 (94.7 mg, 86.1%) was obtained in the same manner as that in Example 24, by using Compound 1 (100 mg, 0.167 mmol) obtained in Example 1 and 1,2-epoxypropane (0.023 mL, 0.333 mmol).

ESI-MS m/z: 659 (M+H)⁺; ¹H-NMR (CDCl₃) δ: 0.89 (t, J=6.8 Hz, 6H), 1.12 (d, J=6.2 Hz, 3H), 1.26-1.40 (m, 28H), 1.52-1.61 (m, 8H), 2.05 (q, J=6.6 Hz, 8H), 2.22-2.30 (m, 1H), 2.41-2.52 (m, 2H), 2.67 (dd, J=10.1, 4.6 Hz, 1H), 2.75-2.85 (m, 5H), 3.03 (dd, J=9.5, 5.9 Hz, 1H), 3.38-3.49 (m, 4H), 3.73-3.85 (m, 3H), 5.29-5.43 (m, 8H).

Example 55

1-(3R,4R)-3,4-bis(((9Z,12Z)-Octadec-9,12-dienyloxy)pyrrolidine-1-yl)-3-methoxypropan-2-ol (Compound 55)

Compound 55 (92.9 mg, 80.8%) was obtained in the same manner as that in Example 24, by using Compound 1 (100 mg, 0.167 mmol) obtained in Example 1 and 2-(methoxymethyl)oxirane (0.035 mL, 0.333 mmol).

ESI-MS m/z: 689 (M+H)⁺; ¹H-NMR (CDCl₃) δ: 0.89 (t, J=6.8 Hz, 6H), 1.30-1.38 (m, 28H), 1.52-1.60 (m, 8H), 2.05 (q, J=6.6 Hz, 8H), 2.33-2.43 (m, 1H), 2.50-2.56 (m, 1H), 2.59-2.68 (m, 2H), 2.77 (t, J=5.9 Hz, 4H), 2.86 (dd, J=9.7, 6.0 Hz, 1H), 3.01 (dd, J=9.7, 6.0 Hz, 1H), 3.33-3.49 (m, 9H), 3.79-3.87 (m, 3H), 5.28-5.43 (m, 8H).

Example 56

3-((3R,4R)-3,4-bis((9Z,12Z)-Octadec-9,12-dienyloxy)pyrrolidin-1-yl)propan-1-ol (compound 56)

Compound 1 (100 mg, 0.167 mmol) obtained in Example 1 was dissolved in ethanol (2 mL), and stirred for 5.5 hours under heat and reflux after adding ethyl acrylate (0.181 mL, 1.67 mmol) and sodium ethoxide (5.7 mg, 0.083 mmol). After cooling the reaction solution, the solvent was distilled away under reduced pressure. The resulting residue was purified by silica gel column chromatography (chloroform/methanol=100/0 to 97/3) to give ethyl 3-((3R,4R)-3,4-bis((9Z,12Z)-octadec-9,12-dienyloxy)pyrrolidin-1-yl)propanoate (107 mg, 91.2%).

The resulting ethyl 3-((3R,4R)-3,4-bis((9Z,12Z)-octadec-9,12-dienyloxy)pyrrolidin-1-yl)propanoate (220 mg, 0.314 mmol) was dissolved in THF (4 mL), and a 1.0 mol/L dibutylaluminum hydride toluene solution (0.943 mL, 0.943 mmol) was added at −78° C. The mixture was stirred for 2 hours under gradually increasing temperatures of −78° C. to 0° C., and a saturated ammonium chloride aqueous solution was added to the reaction mixture. The aqueous layer was extracted with ethyl acetate. The organic layer was washed with saturated brine, dried over magnesium sulfate, and concentrated under reduced pressure after filtration. The resulting residue was purified by silica gel column chromatography (chloroform/methanol=100/3 to 93/7) to give compound 56 (113 mg, 54.5%).

ESI-MS m/z: 659 (M+H)⁺; ¹H-NMR (CDCl₃) δ: 0.89 (dd, J=7.5, 6.0 Hz, 6H), 1.26-1.40 (m, 32H), 1.50-1.59 (m, 4H), 1.66-1.73 (m, 2H), 2.05 (q, J=6.6 Hz, 8H), 2.56-2.79 (m, 8H), 2.90 (dd, J=9.7, 5.7 Hz, 2H), 3.41 (t, J=6.6 Hz, 4H), 3.76-3.81 (m, 4H), 5.28-5.43 (m, 8H).

Example 57

3-((3R,4R)-3,4-bis((9Z,12Z)-Octadec-9,12-dienyloxy)pyrrolidin-1-yl)propanamide (compound 57)

The ethyl 3-((3R,4R)-3,4-bis((9Z,12Z)-octadec-9,12-dienyloxy)pyrrolidin-1-yl)propanoate (180 mg, 0.257 mmol) obtained in Example 56 was dissolved in ethanol (2 mL). The solution was stirred at room temperature for 2 hours after adding a 2 mol/L sodium hydroxide aqueous solution (2 mL). The pH was brought to 4 by adding a 1 mol/L hydrochloric acid aqueous solution to the reaction solution, and the aqueous layer was extracted with chloroform. The organic layer was dried over anhydrous magnesium sulfate, and concentrated under reduced pressure after filtration to give 3-((3R,4R)-3,4-bis((9Z,12Z)-octadec-9,12-dienyloxy)pyrrolidin-1-yl)propanoic acid (148 mg, 85.8%).

The resulting 3-((3R,4R)-3,4-bis((9Z,12Z)-octadec-9,12-dienyloxy)pyrrolidin-1-yl)propanoic acid (64 mg, 0.095 mmol) was dissolved in chloroform (2 mL), and stirred overnight at room temperature after adding O-(7-azabenzotriazol-1-yl)-N,N,N',N'-tetramethyluronium hexafluorophosphate (HATU; Aldrich; 72 mg, 0.190 mmol), diisopropylethylamine (0.083 mL, 0.476 mmol), and a 2 mol/L ammonia methanol solution (0.238 mL, 0.476 mmol). The aqueous layer was extracted with ethyl acetate after adding a saturated sodium bicarbonate aqueous solution to the reaction mixture. The organic layer was washed with water and saturated brine, dried over anhydrous magnesium sulfate, and concentrated under reduced pressure after filtration. The resulting residue was purified by silica gel column chromatography (chloroform/methanol=100/0 to 90/10) to give compound 57 (46.1 mg, 72.1%).

ESI-MS m/z: 672 (M+H)$^+$; $^1$H-NMR (CDCl$_3$) δ: 0.89 (t, J=6.8 Hz, 6H), 1.26-1.40 (m, 32H), 1.51-1.60 (m, 4H), 2.05 (q, J=6.6 Hz, 8H), 2.39 (t, J=6.0 Hz, 2H), 2.56 (dd, J=9.7, 4.2 Hz, 2H), 2.63-2.80 (m, 6H), 2.90 (dd, J=9.7, 5.9 Hz, 2H), 3.37-3.49 (m, 4H), 3.81 (t, J=4.2 Hz, 2H), 5.24 (br s, 1H), 5.28-5.43 (m, 8H), 8.07 (br s, 1H).

Example 58

3-((3R,4R)-3,4-bis((9Z,12Z)-Octadec-9,12-dienyloxy)pyrrolidin-1-yl)-N,N-dimethyl propanamide (compound 58)

The 3-((3R,4R)-3,4-bis((9Z,12Z)-octadec-9,12-dienyloxy)pyrrolidin-1-yl)propanoic acid (63 mg, 0.094 mmol) obtained in Example 57 was dissolved in chloroform (2 mL), and stirred overnight at room temperature after adding O-(7-azabenzotriazol-1-yl)-N,N,N',N'-tetramethyluronium hexafluorophosphate (HATU; Aldrich; 71 mg, 0.187 mmol), a 2 mol/L dimethylamine THF solution (0.234 mL, 0.469 mmol), and diisopropylethylamine (0.082 mL, 0.469 mmol). The aqueous layer was extracted with ethyl acetate after adding a saturated sodium bicarbonate aqueous solution to the reaction mixture. The organic layer was washed with water and saturated brine, dried over anhydrous magnesium sulfate, and concentrated under reduced pressure after filtration. The resulting residue was purified by silica gel column chromatography (chloroform/methanol=100/0 to 95/5) to give compound 58 (60.7 mg, 92.6%).

ESI-MS m/z: 700 (M+H)$^+$; $^1$H-NMR (CDCl$_3$) δ: 0.89 (t, J=7.0 Hz, 6H), 1.26-1.40 (m, 32H), 1.52-1.61 (m, 4H), 2.05 (q, J=6.6 Hz, 8H), 2.51-2.56 (m, 4H), 2.70-2.83 (m, 6H), 2.87-2.95 (m, 2H), 2.93 (s, 3H), 3.00 (s, 3H), 3.37-3.49 (m, 4H), 3.81 (t, J=4.8 Hz, 2H), 5.29-5.43 (m, 8H).

Example 59

(3R,4R)-1-(3-N,N-Dimethylaminopropyl)-3,4-bis((9Z,12Z)-octadec-9,12-dienyloxy)pyrrolidine (compound 59)

Compound 56 (110 mg, 0.167 mmol) obtained in Example 56 was dissolved in dichloromethane (3 mL), and stirred at room temperature for 4 hours after adding triethylamine (0.082 mL, 0.585 mmol) and anhydrous methanesulfonic acid (58 mg, 0.334 mmol). The reaction solution was washed with water and saturated brine, dried over anhydrous magnesium sulfate, and concentrated under reduced pressure after filtration to give a crude product of 3-((3R,4R)-3,4-bis((9Z,12Z)-octadec-9,12-dienyloxy)pyrrolidin-1-yl)propyl methanesulfonate.

The resulting crude product was dissolved in THF (1 mL), and irradiated with microwave (300 W, 100° C., 1 hour) after adding a 2.0 mol/L dimethylamine THF solution (0.835 mL, 1.67 mmol). The reaction solution was concentrated, and the resulting residue was purified by silica gel column chromatography (chloroform/methanol=100/0 to 75/25) to give compound 59 (96.6 mg, 84.4%).

ESI-MS m/z: 686 (M+H)$^+$; $^1$H-NMR (CDCl$_3$) δ: 0.89 (t, J=6.8 Hz, 6H), 1.26-1.40 (m, 32H), 1.52-1.62 (m, 4H), 1.63-1.76 (m, 2H), 2.05 (q, J=6.7 Hz, 8H), 2.23 (s, 6H), 2.29-2.52 (m, 6H), 2.75-2.87 (m, 6H), 3.37-3.49 (m, 4H), 3.81 (t, J=4.8 Hz, 2H), 5.28-5.43 (m, 8H).

Example 60

4-((3R,4R)-3,4-bis((9Z,12Z)-Octadec-9,12-dienyloxy)pyrrolidin-1-yl)-1-methylpiperidine (compound 60)

Compound 60 (72.0 mg, 62.0%) was obtained in the same manner as that in Example 10, by using compound 1 (100 mg, 0.167 mmol) obtained in Example 1, and 1-methylpiperidin-4-one (Aldrich; 0.205 mL, 1.67 mmol).

ESI-MS m/z: 698 (M+H)$^+$; $^1$H-NMR (CDCl$_3$) δ: 0.89 (t, J=6.8 Hz, 6H), 1.29-1.40 (m, 32H), 1.52-1.62 (m, 6H), 1.77-1.83 (m, 2H), 1.89-2.08 (m, 11H), 2.24 (s, 3H), 2.53 (dd, J=9.6, 4.7 Hz, 2H), 2.75-2.85 (m, 6H), 2.92 (dd, J=9.6, 6.2 Hz, 2H), 3.37-3.49 (m, 4H), 3.81 (t, J=4.7 Hz, 2H), 5.28-5.43 (m, 8H).

Example 61

(3R,4R)-1-(2-Aminoacetyl)-3,4-bis((9Z,12Z)-octadec-9,12-dienyloxy)pyrrolidine (compound 61)

Compound 1 (100 mg, 0.167 mmol) obtained in Example 1 was dissolved in chloroform (2 mL), and stirred at room temperature for 4 hours after adding N-(tert-butoxycarbonyl)glycine (Tokyo Chemical Industry Co., Ltd.; 55 mg, 0.250 mmol), diisopropylethylamine (0.146 mL, 0.833 mmol), and HATU (O-(7-azabenzotriazol-1-yl)-N,N,N',N'-tetramethyluronium hexafluorophosphate) (Aldrich; 127 mg, 0.333 mmol). The aqueous layer was extracted with ethyl acetate after adding a saturated sodium bicarbonate aqueous solution to the reaction mixture. The organic layer was washed with water and saturated brine, dried over anhydrous magnesium sulfate, and concentrated under reduced pressure after filtration. The resulting residue was purified by silica gel column chromatography (chloroform/methanol=100/0 to 97/3) to give tert-butyl 2-((3R,4R)-3,4-bis((9Z,12Z)-octadec-9,12-dienyloxy)pyrrolidin-1-yl)-2-oxoethylcarbamate.

The resulting tert-butyl 2-((3R,4R)-3,4-bis((9Z,12Z)-octadec-9,12-dienyloxy)pyrrolidin-1-yl)-2-oxoethylcarbamate was dissolved in dichloromethane (2 mL), and stirred at room temperature for 1.5 hours after adding trifluoroacetic acid (0.256 mL, 3.33 mmol). The aqueous layer was extracted with chloroform after adding a saturated sodium bicarbonate aqueous solution to the reaction mixture. The organic layer was washed with saturated brine, dried over anhydrous magnesium sulfate, and concentrated under reduced pressure after filtration. The resulting residue was purified by silica gel column chromatography (chloroform/methanol=100/0 to 85/15) to give compound 61 (60.5 mg, 55.3%).

ESI-MS m/z: 658 (M+H)+; 1H-NMR (CDCl3) δ: 0.89 (t, J=6.8 Hz, 6H), 1.28-1.40 (m, 32H), 1.49-1.58 (m, 6H), 2.05 (q, J=6.6 Hz, 8H), 2.77 (t, J=5.9 Hz, 4H), 3.30-3.56 (m, 9H), 3.69 (d, J=12.5 Hz, 1H), 3.86 (d, J=4.8 Hz, 1H), 3.92 (d, J=3.7 Hz, 1H), 5.29-5.43 (m, 8H).

Example 62

(3R,4R)-1-(3-Aminopropanoyl)-3,4-bis((9Z,12Z)-octadec-9,12-dienyloxy)pyrrolidine (Compound 62)

Compound 62 (52.5 mg, 49.1%) was obtained in the same manner as that in Example 61, by using Compound 1 (96 mg, 0.160 mmol) obtained in Example 1 and N-(tert-butoxycarbonyl)-β-alanine (Tokyo Chemical Industry Co., Ltd.; 45 mg, 0.240 mmol).

ESI-MS m/z: 672 (M+H)+; 1H-NMR (CDCl3) δ: 0.89 (t, J=7.0 Hz, 6H), 1.26-1.38 (m, 32H), 1.49-1.57 (m, 4H), 1.88 (br s, 2H), 2.05 (q, J=6.7 Hz, 8H), 2.43 (td, J=6.0, 1.5 Hz, 2H), 2.77 (t, J=6.0 Hz, 4H), 3.03 (t, J=6.0 Hz, 2H), 3.37-3.67 (m, 8H), 3.85-3.91 (m, 2H), 5.28-5.43 (m, 8H).

Example 63

(3R,4R)-1-((S)-2,5-Diaminopentanoyl)-3,4-bis((9Z,12Z)-octadec-9,12-dienyloxy) pyrrolidine (Compound 63)

Compound 63 (70.5 mg, 59.4%) was obtained in the same manner as that in Example 61, by using Compound 1 (100 mg, 0.167 mmol) obtained in Example 1 and (S)-2,5-bis(tert-butoxycarbonylamino)pentanoic acid (WATANABE CHEMICAL INDUSTRIES, LTD.; 83 mg, 0.250 mmol).

ESI-MS m/z: 715 (M+H)+; 1H-NMR (CDCl3) δ: 0.89 (t, J=7.0 Hz, 6H), 1.29-1.68 (m, 40H), 2.05 (q, J=6.7 Hz, 8H), 2.69-2.79 (m, 6H), 3.37-3.56 (m, 7H), 3.64-3.69 (m, 2H), 3.85-3.92 (m, 2H), 5.28-5.43 (m, 8H).

Example 64

(3R,4R)-1-(6-Aminohexanoyl)-3,4-bis((9Z,12Z)-octadec-9,12-dienyloxy)pyrrolidine (Compound 64)

Compound 64 (85.5 mg, 71.7%) was obtained in the same manner as that in Example 61, by using Compound 1 (100 mg, 0.167 mmol) obtained in Example 1 and 6-(tert-butoxycarbonylamino)hexanoic acid (WATANABE CHEMICAL INDUSTRIES, LTD.; 58 mg, 0.250 mmol).

ESI-MS m/z: 714 (M+H)+; 1H-NMR (CDCl3) δ: 0.89 (t, J=6.8 Hz, 6H), 1.26-1.71 (m, 42H), 2.05 (q, J=6.6 Hz, 8H), 2.25 (t, J=7.5 Hz, 2H), 2.70-2.79 (m, 6H), 3.37-3.65 (m, 8H), 3.84-3.90 (m, 2H), 5.28-5.43 (m, 8H).

Example 65

(3R,4R)-1-(2-aminoacetyl)pyrrolidine-3,4-diyl di((9Z,12Z)-octadec-9,12-enoate) (Compound 65)

Compound 65 (73.4 mg, 67.3%) was obtained in the same manner as that in Example 61, by using Compound 2 (100 mg, 0.159 mmol) obtained in Example 2 and N-(tert-butoxycarbonyl)glycine (Tokyo Chemical Industry Co., Ltd.; 41.8 mg, 0.239 mmol).

ESI-MS m/z: 686 (M+H)+; 1H-NMR (CDCl3) δ: 0.89 (t, J=6.8 Hz, 6H), 1.26-1.40 (m, 28H), 1.56-1.65 (m, 4H), 2.05 (q, J=6.7 Hz, 8H), 2.27-2.34 (m, 4H), 2.77 (t, J=5.9 Hz, 4H), 3.38-3.53 (m, 3H), 3.68-3.81 (m, 3H), 5.20 (br s, 2H), 5.28-5.43 (m, 8H).

Example 66

(3R,4R)-1-((S)-2,6-Diaminohexanoyl)pyrrolidine-3,4-diyl di((9Z,12Z)-octadec-9,12-enoate) (Compound 66)

Compound 66 (73.0 mg, 60.7%) was obtained in the same manner as that in Example 61, by using Compound 2 (100 mg, 0.159 mmol) obtained in Example 2 and (S)-2,6-bis(tert-butoxycarbonylamino)hexanoic acid (WATANABE CHEMICAL INDUSTRIES, LTD.; 87 mg, 0.239 mmol).

ESI-MS m/z: 757 (M+H)+; 1H-NMR (CDCl3) δ: 0.89 (t, J=6.8 Hz, 6H), 1.26-1.65 (m, 38H), 2.05 (q, J=6.7 Hz, 8H), 2.28-2.34 (m, 4H), 2.70 (t, J=6.1 Hz, 2H), 2.77 (t, J=6.1 Hz, 4H), 3.43 (dd, J=7.3, 4.8 Hz, 1H), 3.54 (d, J=11.9 Hz, 1H), 3.74 (br s, 2H), 3.88 (dd, J=11.9, 4.0 Hz, 1H), 5.20-5.21 (m, 2H), 5.29-5.43 (m, 8H).

Example 67 bis(2-((Z)-Octadec-9-enyloxy)ethyl)amine (Compound 67)

Compound 67 (212 mg, 69.5%) was obtained in the same manner as that in Example 1, by using Compound VI-17 (243 mg, 0.349 mmol) obtained in Reference Example 19.

ESI-MS m/z: 607 (M+H)+; 1H-NMR (CDCl3) δ: 0.88 (t, J=6.8 Hz, 6H), 1.25-1.35 (m, 44H), 1.54-1.59 (m, 4H), 1.65 (s, 1H), 1.98-2.05 (m, 8H), 2.80 (t, J=5.3 Hz, 4H), 3.42 (t, J=6.8 Hz, 4H), 3.53 (t, J=5.3 Hz, 4H), 5.29-5.40 (m, 4H).

Example 68 bis(2-((Z)-Tetradec-9-enyloxy)ethyl)amine (Compound 68)

Compound 68 (291 mg, 85.6%) was obtained in the same manner as that in Example 1, by using Compound VI-18 (402 mg, 0.688 mmol) obtained in Reference Example 20.

ESI-MS m/z: 494 (M+H)+; 1H-NMR (CDCl3) δ: 0.90 (t, J=7.1 Hz, 6H), 1.29 (br s, 28H), 1.53-1.62 (m, 4H), 1.97-2.06 (m, 9H), 2.81 (t, J=5.3 Hz, 4H), 3.42 (t, J=6.7 Hz, 4H), 3.53 (t, J=5.4 Hz, 4H), 5.29-5.40 (m, 4H).

Example 69 bis(2-(Tetradecyloxy)ethyl)amine (Compound 69)

Compound 69 (79.2 mg, 62.4%) was obtained in the same manner as that in Example 1, by using Compound VI-19 (150 mg, 0.255 mmol) obtained in Reference Example 21.

ESI-MS m/z: 499 (M+H)+; 1H-NMR (CDCl3) δ: 0.88 (t, J=6.6 Hz, 6H), 1.26 (br s, 44H), 1.52-1.60 (m, 4H), 1.89 (br s, 1H), 2.81 (t, J=5.4 Hz, 4H), 3.43 (t, J=6.7 Hz, 4H), 3.54 (t, J=5.3 Hz, 4H).

Example 70 bis(2-(Hexadecyloxy)ethyl)amine (Compound 70)

Compound 70 (244 mg, 72.9%) was obtained in the same manner as that in Example 1, by using Compound VI-20 (389 mg, 0.604 mmol) obtained in Reference Example 22.

ESI-MS m/z: 555 (M+H)$^+$; $^1$H-NMR (CDCl$_3$) δ: 0.88 (t, J=6.6 Hz, 6H), 1.26 (br s, 52H), 1.52-1.61 (m, 4H), 1.91 (br s, 1H), 2.82 (t, J=5.4 Hz, 4H), 3.43 (t, J=6.7 Hz, 4H), 3.54 (t, J=5.4 Hz, 4H).

Example 71 bis(2-(Octadecyloxy)ethyl)amine (Compound 71)

Compound 71 (151 mg, 43.4%) was obtained in the same manner as that in Example 1, by using Compound VI-21 (399 mg, 0.570 mmol) obtained in Reference Example 23.
ESI-MS m/z: 611 (M+H)$^+$; $^1$H-NMR (CDCl$_3$) δ: 0.88 (t, J=6.7 Hz, 6H), 1.25 (br s, 60H), 1.51-1.60 (m, 4H), 2.08 (br s, 1H), 2.84 (t, J=5.3 Hz, 4H), 3.43 (t, J=6.6 Hz, 4H), 3.55 (t, J=5.4 Hz, 4H).

Example 72 bis(2-((Z)-Hexadec-9-enyloxy)ethyl)amine (Compound 72)

Compound 72 (516 mg, 85.9%) was obtained in the same manner as that in Example 1, by using Compound VI-22 (700 mg, 1.09 mmol) obtained in Reference Example 24.
ESI-MS m/z: 550 (M+H)$^+$; $^1$H-NMR (CDCl$_3$) δ: 0.88 (t, J=6.8 Hz, 6H), 1.26-1.35 (m, 36H), 1.52-1.63 (m, 4H), 2.01 (q, J=5.5 Hz, 8H), 2.80 (t, J=5.3 Hz, 4H), 3.42 (t, J=6.6 Hz, 4H), 3.53 (t, J=5.3 Hz, 4H), 5.30-5.40 (m, 4H).

Example 73

N,N-bis(2-((Z)-Octadec-9-enoyloxy)ethyl)amine (compound 73)

tert-Butyl bis(2-hydroxyethyl)carbamate (Aldrich; 600 mg, 2.92 mmol) was dissolved in dichloromethane (30 mL), and stirred overnight at room temperature after adding oleic acid (Tokyo Chemical Industry Co., Ltd.; 1.82 g, 6.43 mmol), 1-ethyl-3-(3-dimethylaminopropyl)carbodiimide hydrochloride (1.29 g, 6.72 mmol), and 4-dimethylaminopyridine (89 mg, 0.731 mmol). The aqueous layer was extracted with ethyl acetate after adding a saturated sodium bicarbonate aqueous solution to the reaction mixture. The organic layer was washed with saturated brine, dried over magnesium sulfate, and concentrated under reduced pressure after filtration. The resulting residue was purified by silica gel column chromatography (hexane/chloroform=50/50 to 0/100) to give tert-butyl N,N-bis(2-(0-octadec-9-enoyloxy)ethyl)carbamate (1.26 g, 58.7%).
The resulting tert-butyl N,N-bis(2-((Z)-octadec-9-enoyloxy)ethyl)carbamate (1.22 g, 1.66 mmol) was dissolved in dichloromethane (30 mL), and stirred at room temperature for 3.5 hours after adding trifluoroacetic acid (2.56 mL, 33.2 mmol). The aqueous layer was extracted with chloroform after adding a saturated sodium bicarbonate aqueous solution to the reaction solution. The organic layer was washed with saturated brine, dried over anhydrous magnesium sulfate, and concentrated under reduced pressure after filtration. The resulting residue was purified by silica gel column chromatography (chloroform/methanol=100/0 to 96/4) to give compound 73 (998 mg, 94.6%).
ESI-MS m/z: 635 (M+H)$^+$; $^1$H-NMR (CDCl$_3$) δ: 0.88 (t, J=6.8 Hz, 6H), 1.27-1.35 (m, 40H), 1.58-1.67 (m, 4H), 2.01 (q, J=5.5 Hz, 8H), 2.32 (t, J=7.7 Hz, 4H), 2.89 (t, J=5.5 Hz, 4H), 4.18 (t, J=5.5 Hz, 4H), 5.29-5.40 (m, 4H).

Example 74

N,N-bis(2-((9Z,12Z)-Octadec-9,12-dienoyloxy)ethyl)amine (Compound 74)

Compound 74 (494 mg, 82.6%) was obtained in the same manner as that in Example 73, by using tert-butyl bis(2-hydroxyethyl) carbamate (Aldrich; 415 mg, 2.02 mmol) and linoleic acid (Aldrich; 1.25 g, 4.45 mmol).
ESI-MS m/z: 631 (M+H)$^+$; $^1$H-NMR (CDCl$_3$) δ: 0.89 (t, J=6.7 Hz, 6H), 1.31 (br s, 28H), 1.54 (br s, 1H), 1.58-1.66 (m, 4H), 2.00-2.09 (m, 8H), 2.32 (t, J=7.6 Hz, 4H), 2.77 (t, J=5.9 Hz, 4H), 2.89 (t, J=5.4 Hz, 4H), 4.17 (t, J=5.6 Hz, 4H), 5.28-5.43 (m, 8H).

Example 75

N-Methyl-N,N-bis(2-((Z)-Tetradec-9-enyloxy)ethyl)amine (Compound 75)

Compound 75 (25.5 mg, 23.9%) was obtained in the same manner as that in Reference Example 1, by using N-methyldiethanolamine (Tokyo Chemical Industry Co., Ltd.; 25.0 mg, 0.210 mmol) and (Z)-tetradec-9-enyl methanesulfonate (Nu-Chek Prep, Inc; 152 mg, 0.524 mmol).
ESI-MS m/z: 509 (M+H)$^+$; $^1$H-NMR (CDCl$_3$) δ: 0.90 (t, J=7.1 Hz, 6H), 1.25-1.37 (m, 28H), 1.51-1.62 (m, 4H), 1.98-2.06 (m, 8H), 2.33 (s, 3H), 2.64 (t, J=6.1 Hz, 4H), 3.41 (t, J=6.7 Hz, 4H), 3.52 (t, J=6.1 Hz, 4H), 5.29-5.41 (m, 4H).

Example 76

N,N-bis(2-(Hexadecyloxy)ethyl)-N-methylamine (Compound 76)

Compound 76 (135 mg, 47.2%) was obtained in the same manner as that in Reference Example 5, by using N-methyldiethanolamine (Tokyo Chemical Industry Co., Ltd.; 60.0 mg, 0.504 mmol) and hexadecyl methanesulfonate (Nu-Chek Prep, Inc; 403 mg, 1.26 mmol).
ESI-MS m/z: 569 (M+H)$^+$; $^1$H-NMR (CDCl$_3$) δ: 0.88 (t, J=6.8 Hz, 6H), 1.26 (br s, 52H), 1.52-1.61 (m, 4H), 2.33 (s, 3H), 2.64 (t, J=6.0 Hz, 4H), 3.41 (t, J=6.8 Hz, 4H), 3.52 (t, J=6.0 Hz, 4H).

Example 77

N-Methyl-N,N-bis(2-((Z)-octadec-11-enyloxy)ethyl)amine (Compound 77)

Compound 77 (198 mg, 47.5%) was obtained in the same manner as that in Reference Example 1, by using N-methyldiethanolamine (Tokyo Chemical Industry Co., Ltd.; 80 mg, 0.671 mmol) and (Z)-octadec-11-enyl methanesulfonate (Nu-Chek Prep, Inc; 582 mg, 1.68 mmol).
ESI-MS m/z: 621 (M+H)$^+$; $^1$H-NMR (CDCl$_3$) δ: 0.88 (t, J=6.6 Hz, 6H), 1.26-1.35 (m, 44H), 1.56 (dd, J=16.9, 10.3 Hz, 4H), 2.01 (q, J=5.5 Hz, 8H), 2.33 (s, 3H), 2.64 (t, J=6.0 Hz, 4H), 3.41 (t, J=6.8 Hz, 4H), 3.52 (t, J=6.0 Hz, 4H), 5.30-5.40 (m, 4H).

Example 78

N,N-bis(2-((Z)-Icos-11-enyloxy)ethyl)-N-methylamine (Compound 78)

Compound 78 (164 mg, 45.1%) was obtained in the same manner as that in Reference Example 1, by using N-methyldiethanolamine (Tokyo Chemical Industry Co., Ltd.; 64.1 mg, 0.538 mmol) and (Z)-icos-11-enyl methanesulfonate (Nu-Chek Prep, Inc; 504 mg, 1.35 mmol).

ESI-MS m/z: 677 (M+H)$^+$; $^1$H-NMR (CDCl$_3$) δ: 0.88 (t, J=6.7 Hz, 6H), 1.27 (br s, 52H), 1.50-1.61 (m, 4H), 1.96-2.06 (m, 8H), 2.33 (s, 3H), 2.64 (t, J=6.1 Hz, 4H), 3.41 (t, J=6.7 Hz, 4H), 3.52 (t, J=6.1 Hz, 4H), 5.29-5.40 (m, 4H).

Example 79

N,N-bis(2-((11Z,14Z)-Icos-11,14-dienyloxy)ethyl)-N-methylamine (Compound 79)

Compound 79 (204 mg, 62.4%) was obtained in the same manner as that in Reference Example 1, by using N-methyldiethanolamine (Tokyo Chemical Industry Co., Ltd.; 58.0 mg, 0.487 mmol) and (11Z,14Z)-icos-11,14-dienyl methanesulfonate (Nu-Chek Prep, Inc; 453 mg, 1.22 mmol).

ESI-MS m/z: 673 (M+H)$^+$; $^1$H-NMR (CDCl$_3$) δ: 0.89 (t, J=6.7 Hz, 6H), 1.29 (br s, 40H), 1.51-1.60 (m, 4H), 2.01-2.09 (m, 8H), 2.33 (s, 3H), 2.64 (t, J=6.1 Hz, 4H), 2.77 (t, J=5.6 Hz, 4H), 3.41 (t, J=6.7 Hz, 4H), 3.52 (t, J=6.1 Hz, 4H), 5.28-5.43 (m, 8H).

Example 80

N,N-diMethyl-N,N-bis(2-((Z)-octadec-9-enyloxy) ethyl) aminium chloride (Compound 80)

Compound 80 (114 mg, 99.0%) was obtained in the same manner as that in Example 22, by using Compound 67 (104 mg, 0.172 mmol) obtained in Example 67.

ESI-MS m/z: 635 M$^+$; $^1$H-NMR (CDCl$_3$) δ: 0.88 (t, J=6.6 Hz, 6H), 1.27-1.35 (m, 44H), 1.51-1.60 (m, 4H), 2.01 (q, J=5.9 Hz, 8H), 3.44 (s, 6H), 3.46 (t, J=6.6 Hz, 4H), 3.87-3.91 (m, 4H), 3.97-4.01 (m, 4H), 5.29-5.40 (m, 4H).

Example 81

N,N-diMethyl-N,N-bis(2-((Z)-octadec-9-enoyloxy) ethyl) aminium chloride (Compound 81)

Compound 81 (86.9 mg, 79.0%) was obtained in the same manner as that in Example 22, by using Compound 73 (100 mg, 0.158 mmol) obtained in Example 73.

ESI-MS m/z: 663 M$^+$; $^1$H-NMR (CDCl$_3$) δ: 0.88 (t, J=6.8 Hz, 6H), 1.26-1.35 (m, 40H), 1.56-1.65 (m, 4H), 2.01 (q, J=5.9 Hz, 8H), 2.35 (t, J=7.7 Hz, 4H), 3.53 (s, 6H), 4.12-4.15 (m, 4H), 4.58-4.62 (m, 4H), 5.29-5.40 (m, 4H).

Example 82

3-(bis(2-((Z)-Octadec-9-enyloxy)ethyl)amino) propan-1,2-diol (Compound 82)

Compound 82 (24.2 mg, 14.4%) was obtained in the same manner as that in Example 10, by using Compound 67 (150 mg, 0.247 mmol) obtained in Example 67 and DL-2,3-dihydroxypropanal (Aldrich; 223 mg, 2.48 mmol).

ESI-MS m/z: 681 (M+H)$^+$; $^1$H-NMR (CDCl$_3$) δ: 0.88 (t, J=6.8 Hz, 6H), 1.27-1.36 (m, 44H), 1.52-1.61 (m, 4H), 2.01 (q, J=5.9 Hz, 8H), 2.67-2.69 (m, 2H), 2.73-2.88 (m, 4H), 3.41 (t, J=6.8 Hz, 4H), 3.45-3.54 (m, 5H), 3.64-3.74 (m, 2H), 5.30-5.40 (m, 4H).

Example 83

3-(bis(2-((Z)-Octadec-9-enoyloxy)ethyl)amino) propan-1,2-diol (Compound 83)

Compound 83 (42.2 mg, 24.2%) was obtained in the same manner as that in Example 10, by using Compound 73 (150 mg, 0.246 mmol) obtained in Example 73 and DL-2,3-dihydroxypropanal (Aldrich; 222 mg, 2.46 mmol).

ESI-MS m/z: 709 (M+H)$^+$; $^1$H-NMR (CDCl$_3$) δ: 0.88 (t, J=6.8 Hz, 6H), 1.27-1.35 (m, 40H), 1.56-1.66 (m, 4H), 2.01 (q, J=5.9 Hz, 8H), 2.31 (t, J=7.5 Hz, 4H), 2.59-2.72 (m, 2H), 2.76-2.93 (m, 4H), 3.45-3.52 (m, 1H), 3.66-3.78 (m, 2H), 4.09-4.21 (m, 4H), 5.29-5.40 (m, 4H).

Example 84

3-(bis(2-((Z)-Octadec-9-enyloxy)ethyl)amino) propanamide (compound 84)

Compound 67 (400 mg, 0.660 mmol) obtained in Example 67 was dissolved in ethanol (8 mL), and stirred overnight under heat and reflux after adding ethyl acrylate (3.59 mL, 33.0 mmol) and sodium ethoxide (22.5 mg, 0.330 mmol). After cooling the reaction solution, the solvent was distilled away under reduced pressure. The resulting residue was purified by silica gel column chromatography (chloroform/methanol 100/0 to 98/2) to give ethyl 3-(bis(2-((Z)-octadec-9-enyloxy)ethyl)amino) propanoate (399 mg, 85.6%).

The resulting ethyl 3-(bis(2-((Z)-octadec-9-enyloxy)ethyl)amino) propanoate (200 mg, 0.283 mmol) was dissolved in ethanol (4 mL), and stirred at room temperature for 6 hours after adding a 2 mol/L sodium hydroxide aqueous solution (3 mL). The pH was brought to 6 by adding a 1 mol/L hydrochloric acid aqueous solution to the reaction solution, and the aqueous layer was extracted with chloroform. The organic layer was dried over anhydrous magnesium sulfate, and concentrated under reduced pressure after filtration to give 3-(bis(2-(0-octadec-9-enyloxy)ethyl) amino)propanoic acid (188 mg, 98.0%).

The resulting 3-(bis(2-(0-octadec-9-enyloxy)ethyl) amino)propanoic acid (85 mg, 0.125 mmol) was dissolved in chloroform (3 mL), and stirred overnight at room temperature after adding O-(7-azabenzotriazol-1-yl)-N,N,N',N'-tetramethyluronium hexafluorophosphate (HATU; Aldrich; 95 mg, 0.251 mmol), a 7 mol/L ammonia methanol solution (0.090 mL, 0.627 mmol), and diisopropylethylamine (0.109 mL, 0.627 mmol). The aqueous layer was extracted with ethyl acetate after adding a saturated sodium bicarbonate aqueous solution to the reaction mixture. The organic layer was washed with water and saturated brine, dried over anhydrous magnesium sulfate, and concentrated under reduced pressure after filtration. The resulting residue was purified by silica gel column chromatography (chloroform/methanol=100/0 to 88/12) to give compound 84 (72.3 mg, 85.0%).

ESI-MS m/z: 678 (M+H)$^+$; $^1$H-NMR (CDCl$_3$) δ: 0.88 (t, J=6.8 Hz, 6H), 1.27-1.35 (m, 44H), 1.48-1.57 (m, 4H), 2.01 (q, J=5.9 Hz, 8H), 2.36 (t, J=5.7 Hz, 2H), 2.72-2.80 (m, 6H), 3.39 (t, J=6.8 Hz, 4H), 3.48 (t, J=5.7 Hz, 4H), 5.18 (br s, 1H), 5.29-5.40 (m, 4H), 8.22 (br s, 1H).

Example 85

3-(bis(2-((Z)-Octadec-9-enyloxy)ethyl)amino)N-dimethylpropanamide (compound 85)

The 3-(bis(2-(0-octadec-9-enyloxy)ethyl)amino)propanoic acid (80 mg, 0.118 mmol) obtained in Example 84 was dissolved in chloroform (3 mL), and stirred overnight at room temperature after adding O-(7-azabenzotriazol-1-yl)-N,N,N',N'-tetramethyluronium hexafluorophosphate (HATU; Aldrich; 90 mg, 0.236 mmol), a 2 mol/L dimethylamine THF solution (0.295 mL, 0.590 mmol), and diisopropylethylamine (0.103 mL, 0.590 mmol). The aqueous layer was extracted with ethyl acetate after adding a saturated sodium bicarbonate aqueous solution to the reaction mixture. The organic layer was washed with water and saturated brine, dried over anhydrous magnesium sulfate, and concentrated under reduced pressure after filtration. The resulting residue was purified by silica gel column chromatography (chloroform/methanol=100/0 to 94/6) to give compound 85 (71.1 mg, 85.6%).

ESI-MS m/z: 706 (M+H)$^+$; $^1$H-NMR (CDCl$_3$) δ: 0.88 (t, J=6.8 Hz, 6H), 1.27-1.35 (m, 44H), 1.51-1.59 (m, 4H), 2.01 (q, J=5.5 Hz, 8H), 2.56 (br s, 2H), 2.79-2.96 (m, 6H), 2.94 (s, 3H), 3.02 (s, 3H), 3.41 (t, J=6.8 Hz, 4H), 3.53 (br s, 4H), 5.29-5.40 (m, 4H).

Example 86

2-Amino-N,N-bis(2-((Z)-octadec-9-enyloxy)ethyl) acetamide (Compound 89)

Compound 86 (83.0 mg, 76.1%) was obtained in the same manner as that in Example 61, by using Compound 67 (100 mg, 0.165 mmol) obtained in Example 67 and N-(tert-butoxycarbonyl)glycine (Tokyo Chemical Industry Co., Ltd.; 43 mg, 0.247 mmol).

ESI-MS m/z: 664 (M+H)$^+$; $^1$H-NMR (CDCl$_3$) δ: 0.88 (t, J=6.8 Hz, 6H), 1.27-1.35 (m, 44H), 1.49-1.57 (m, 4H), 2.01 (q, J=5.9 Hz, 8H), 3.39 (td, J=6.6, 2.2 Hz, 4H), 3.48-3.51 (m, 4H), 3.53 (s, 2H), 3.56 (s, 4H), 5.29-5.40 (m, 4H).

Example 87

3-Amino-N,N-bis(2-((Z)-octadec-9-enyloxy)ethyl) propanamido (Compound 87)

Compound 87 (84.2 mg, 75.2%) was obtained in the same manner as that in Example 61, by using Compound 67 (100 mg, 0.165 mmol) obtained in Example 67 and N-(tert-butoxycarbonyl)-β-alanine (Tokyo Chemical Industry Co., Ltd.; 47 mg, 0.247 mmol).

ESI-MS m/z: 678 (M+H)$^+$; $^1$H-NMR (CDCl$_3$) δ: 0.88 (t, J=6.6 Hz, 6H), 1.27-1.35 (m, 44H), 1.49-1.58 (m, 4H), 2.01 (q, J=5.9 Hz, 8H), 2.55 (t, J=6.0 Hz, 2H), 2.99 (t, J=6.0 Hz, 2H), 3.39 (t, J=6.8 Hz, 4H), 3.51-3.57 (m, 8H), 5.29-5.40 (m, 4H).

Example 88

6-Amino-N,N-bis(2-((Z)-octadec-9-enyloxy)ethyl) (Compound 88)

Compound 88 (87.8 mg, 74.1%) was obtained in the same manner as that in Example 61, by using Compound 67 (100 mg, 0.165 mmol) obtained in Example 67 and 6-(tert-butoxycarbonylamino)hexanoic acid (WATANABE CHEMICAL INDUSTRIES, LTD.; 57 mg, 0.247 mmol).

ESI-MS m/z: 720 (M+H)$^+$; $^1$H-NMR (CDCl$_3$) δ: 0.88 (t, J=6.8 Hz, 6H), 1.27-1.38 (m, 44H), 1.41-1.56 (m, 8H), 1.60-1.70 (m, 2H), 2.01 (q, J=5.5 Hz, 8H), 2.39 (t, J=7.5 Hz, 2H), 2.69 (t, J=6.8 Hz, 2H), 3.39 (t, J=6.4 Hz, 4H), 3.49-3.56 (m, 8H), 5.29-5.40 (m, 4H).

Example 89

2-(Dimethylamino)-N,N-bis(2-((Z)-octadec-9-enyloxy)ethyl)acetamide (Compound 89)

Compound 89 (92.1 mg, 80.8%) was obtained in the same manner as that in Example 25, by using Compound 67 (100 mg, 0.165 mmol) obtained in Example 67 and N,N-dimethylglycine hydrochloride (Tokyo Chemical Industry Co., Ltd.; 26 mg, 0.247 mmol).

ESI-MS m/z: 692 (M+H)$^+$; $^1$H-NMR (CDCl$_3$) δ: 0.88 (t, J=6.6 Hz, 6H), 1.27-1.35 (m, 44H), 1.49-1.58 (m, 4H), 2.01 (q, J=5.5 Hz, 8H), 2.29 (s, 6H), 3.20 (s, 2H), 3.39 (t, J=6.6 Hz, 4H), 3.50-3.57 (m, 6H), 3.68 (t, J=5.5 Hz, 2H), 5.30-5.40 (m, 4H).

Example 90

3-(Dimethylamino)-N,N-bis(2-((Z)-octadec-9-enyloxy)ethyl) propanamido (Compound 90)

Compound 90 (53.7 mg, 46.2%) was obtained in the same manner as that in Example 25, by using Compound 67 (100 mg, 0.165 mmol) obtained in Example 67 and 3-(dimethylamino) propionic acid (MATRIX Scientific; 29 mg, 0.247 mmol).

ESI-MS m/z: 706 (M+H)$^+$; $^1$H-NMR (CDCl$_3$) δ: 0.88 (t, J=6.8 Hz, 6H), 1.27-1.35 (m, 44H), 1.49-1.58 (m, 4H), 2.01 (q, J=5.5 Hz, 8H), 2.26 (s, 6H), 2.55-2.68 (m, 4H), 3.39 (t, J=6.6 Hz, 4H), 3.50-3.59 (m, 8H), 5.30-5.40 (m, 4H).

Example 91

(S)-2-Amino-3-hydroxy-N,N-bis(2-((Z)-octadec-9-enyloxy)ethyl) propanamido (Compound 91)

Compound 91 (31.0 mg, 27.1%) was obtained in the same manner as that in Example 61, by using Compound 67 (100 mg, 0.165 mmol) obtained in Example 67 and (S)-2-(tert-butoxycarbonylamino)-3-hydroxypropanoic acid (WATANABE CHEMICAL INDUSTRIES, LTD.; 51 mg, 0.247 mmol).

ESI-MS m/z: 694 (M+H)$^+$; $^1$H-NMR (CDCl$_3$) δ: 0.88 (t, J=6.8 Hz, 6H), 1.27-1.35 (m, 44H), 1.49-1.58 (m, 4H), 2.01 (q, J=5.9 Hz, 8H), 3.37-3.45 (m, 5H), 3.49-3.77 (m, 9H), 3.92 (dd, J=6.4, 4.9 Hz, 1H), 5.29-5.40 (m, 4H).

Example 92

(S)-2,3-Diamino-N,N-bis(2-((Z)-octadec-9-enyloxy) ethyl) propanamido (Compound 92)

Compound 92 (91.3 mg, 80.1%) was obtained in the same manner as that in Example 61, by using Compound 67 (100 mg, 0.165 mmol) obtained in Example 67 and (S)-2,3-bis (tert-butoxycarbonylamino) propanoic acid dicyclohexylamine salt (WATANABE CHEMICAL INDUSTRIES, LTD.; 120 mg, 0.247 mmol).

ESI-MS m/z: 693 (M+H)⁺; ¹H-NMR (CDCl₃) δ: 0.88 (t, J=6.8 Hz, 6H), 1.28-1.35 (m, 44H), 1.50-1.58 (m, 4H), 2.01 (q, J=5.9 Hz, 8H), 2.70 (dd, J=12.6, 7.3 Hz, 1H), 2.86 (dd, J=12.6, 5.1 Hz, 1H), 3.32-3.43 (m, 5H), 3.47-3.58 (m, 5H), 3.71-3.81 (m, 3H), 5.29-5.40 (m, 4H).

Example 93

(S)-2,5-Diamino-N,N-bis(2-((Z)-octadec-9-enyloxy)ethyl)pentanamido (Compound 93)

Compound 93 (57.5 mg, 48.3%) was obtained in the same manner as that in Example 61, by using Compound 67 (100 mg, 0.165 mmol) obtained in Example 67 and (S)-2,5-bis(tert-butoxycarbonylamino)pentanoic acid (WATANABE CHEMICAL INDUSTRIES, LTD.; 82 mg, 0.247 mmol).

ESI-MS m/z: 721 (M+H)⁺; ¹H-NMR (CDCl₃) δ: 0.88 (t, J=6.6 Hz, 6H), 1.27-1.35 (m, 44H), 1.43-1.70 (m, 8H), 2.01 (q, J=5.5 Hz, 8H), 2.68-2.73 (m, 2H), 3.29-3.57 (m, 10H), 3.65-3.81 (m, 3H), 5.29-5.40 (m, 4H).

Example 94

(S)-2,6-Diamino-N,N-bis(2-((Z)-octadec-9-enyloxy)ethyl) hexanamido (Compound 94)

Compound 94 (55.7 mg, 46.0%) was obtained in the same manner as that in Example 61, by using Compound 67 (100 mg, 0.165 mmol) obtained in Example 67 and (S)-2,6-bis(tert-butoxycarbonylamino)hexanoic acid (WATANABE CHEMICAL INDUSTRIES, LTD.; 90 mg, 0.247 mmol).

ESI-MS m/z: 735 (M+H)⁺; ¹H-NMR (CDCl₃) δ: 0.88 (t, J=6.8 Hz, 6H), 1.27-1.38 (m, 46H), 1.41-1.62 (m, 8H), 2.01 (q, J=5.5 Hz, 8H), 2.69 (t, J=6.6 Hz, 2H), 3.28-3.57 (m, 10H), 3.65-3.82 (m, 3H), 5.29-5.40 (m, 4H).

Example 95

2-Amino-N,N-bis(2-((Z)-octadec-9-enoyloxy)ethyl)acetamide (Compound 95)

Compound 95 (72.8 mg, 66.7%) was obtained in the same manner as that in Example 61, by using Compound 73 (100 mg, 0.158 mmol) obtained in Example 73 and N-(tert-butoxycarbonyl)glycine (Tokyo Chemical Industry Co., Ltd.; 41.4 mg, 0.237 mmol).

ESI-MS m/z: 692 (M+H)⁺; ¹H-NMR (CDCl₃) δ: 0.88 (t, J=6.8 Hz, 6H), 1.27-1.35 (m, 40H), 1.55-1.64 (m, 4H), 2.01 (q, J=5.5 Hz, 8H), 2.30 (td, J=7.7, 2.6 Hz, 4H), 3.51 (s, 2H), 3.53 (t, J=7.0 Hz, 2H), 3.63 (t, J=5.7 Hz, 2H), 4.17-4.25 (m, 4H), 5.29-5.40 (m, 4H).

Example 96

2-Amino-N,N-bis(2-((9Z,12Z)-octadec-9,12-dienoyloxy)ethyl)acetamide (Compound 96)

Compound 96 (36.3 mg, 33.3%) was obtained in the same manner as that in Example 61, by using Compound 74 (100 mg, 0.159 mmol) obtained in Example 74.

ESI-MS m/z: 688 (M+H)⁺; ¹H-NMR (CDCl₃) δ: 0.89 (t, J=6.8 Hz, 6H), 1.30 (br s, 28H), 1.55-1.65 (m, 4H), 2.01-2.08 (m, 8H), 2.27-2.34 (m, 4H), 2.77 (t, J=5.9 Hz, 4H), 3.50-3.66 (m, 6H), 4.16-4.27 (m, 4H), 5.28-5.43 (m, 8H).

Example 97

(S)-2,6-Diamino-N,N-bis(2-((Z)-octadec-9-enoyloxy)ethyl) hexanamido (Compound 97)

Compound 97 (49.1 mg, 40.8%) was obtained in the same manner as that in Example 61, by using Compound 73 (100 mg, 0.158 mmol) obtained in Example 73 and (S)-2,6-bis(tert-butoxycarbonylamino)hexanoic acid (WATANABE CHEMICAL INDUSTRIES, LTD.; 86 mg, 0.237 mmol).

ESI-MS m/z: 763 (M+H)⁺; ¹H-NMR (CDCl₃) δ: 0.88 (t, J=6.8 Hz, 6H), 1.27-1.65 (m, 50H), 2.01 (q, J=5.5 Hz, 8H), 2.27-2.33 (m, 4H), 2.70 (t, J=6.2 Hz, 2H), 3.37-3.56 (m, 2H), 3.64-3.87 (m, 3H), 4.18-4.24 (m, 4H), 5.29-5.40 (m, 4H).

Example 98

2-(Dimethylamino)-N,N-bis(2-((Z)-octadec-9-enoyloxy)ethyl)acetamide (Compound 98)

Compound 98 (72.1 mg, 60.5%) was obtained in the same manner as that in Example 25, by using Compound 73 (105 mg, 0.166 mmol) obtained in Example 73 and N,N-dimethylglycine hydrochloride (Tokyo Chemical Industry Co., Ltd.; 25.6 mg, 0.248 mmol).

ESI-MS m/z: 720 (M+H)⁺; ¹H-NMR (CDCl₃) δ: 0.88 (t, J=6.8 Hz, 6H), 1.27-1.34 (m, 40H), 1.57-1.64 (m, 4H), 2.01 (q, J=5.9 Hz, 8H), 2.27-2.35 (m, 10H), 3.15 (s, 2H), 3.61 (t, J=5.9 Hz, 2H), 3.78 (t, J=5.9 Hz, 2H), 4.22 (q, J=5.5 Hz, 4H), 5.30-5.39 (m, 4H).

Example 99

3-(Dimethylamino)-N,N-bis(2-((Z)-octadec-9-enoyloxy)ethyl) propanamido (Compound 99)

Compound 99 (25.3 mg, 21.9%) was obtained in the same manner as that in Example 25, by using Compound 73 (100 mg, 0.158 mmol) obtained in Example 73 and 3-(dimethylamino) propionic acid (MATRIX Scientific; 36.2 mg, 0.309 mmol).

ESI-MS m/z: 734 (M+H)⁺; ¹H-NMR (CDCl₃) δ: 0.88 (t, J=6.8 Hz, 6H), 1.27-1.35 (m, 40H), 1.56-1.63 (m, 4H), 2.01 (q, J=5.9 Hz, 8H), 2.27-2.33 (m, 10H), 2.52-2.68 (m, 4H), 3.59-3.64 (m, 4H), 4.18-4.23 (m, 4H), 5.29-5.40 (m, 4H).

Example 100

(S)-2,6-Diamino-N,N-bis(2-((9Z,12Z)-octadec-9,12-dienoyloxy)ethyl) hexanamido (Compound 100)

Compound 100 (85.1 mg, 70.8%) was obtained in the same manner as that in Example 61, by using Compound 74 (100 mg, 0.159 mmol) obtained in Example 74 and (S)-2,6-bis(tert-butoxycarbonylamino)hexanoic acid (WATANABE CHEMICAL INDUSTRIES, LTD.; 87 mg, 0.238 mmol).

ESI-MS m/z: 759 (M+H)⁺; ¹H-NMR (CDCl₃) δ: 0.89 (t, J=6.8 Hz, 6H), 1.26-1.65 (m, 38H), 2.05 (q, J=6.7 Hz, 8H), 2.30 (td, J=7.4, 6.0 Hz, 4H), 2.70 (t, J=6.4 Hz, 2H), 2.77 (t, J=5.7 Hz, 4H), 3.37-3.57 (m, 2H), 3.64-3.87 (m, 3H), 4.21 (q, J=5.7 Hz, 4H), 5.28-5.44 (m, 8H).

Example 101 trans-3,4-bis(((Z)-Octadec-9-enyloxy)methyl)pyrrolidine (Compound 101)

Compound 101 (252 mg, 80.6%) was obtained in the same manner as that in Example 1, by using Compound VI-23 (357 mg, 0.494 mmol) obtained in Reference Example 25.

ESI-MS m/z: 633 (M+H)$^+$; $^1$H-NMR (CDCl$_3$) δ: 0.88 (t, J=6.8 Hz, 6H), 1.27-1.35 (m, 44H), 1.50-1.59 (m, 4H), 2.01 (q, J=5.5 Hz, 10H), 2.69 (dd, J=11.3, 5.5 Hz, 2H), 3.06 (dd, J=11.3, 7.1 Hz, 2H), 3.28-3.46 (m, 8H), 5.30-5.40 (m, 4H).

Example 102 trans-3,4-bis(((9Z,12Z)-Octadec-9,12-dienyloxy)methyl)pyrrolidine (Compound 102)

Compound 102 (276 mg, 82.7%) was obtained in the same manner as that in Example 1, by using Compound VI-24 (382 mg, 0.532 mmol) obtained in Reference Example 26.

ESI-MS m/z: 629 (M+H)$^+$; $^1$H-NMR (CDCl$_3$) δ: 0.89 (t, J=6.8 Hz, 6H), 1.29-1.40 (m, 32H), 1.50-1.59 (m, 4H), 1.97-2.08 (m, 10H), 2.69 (dd, J=11.2, 5.7 Hz, 2H), 2.77 (t, J=6.0 Hz, 4H), 3.06 (dd, J=11.2, 7.1 Hz, 2H), 3.28-3.46 (m, 8H), 5.29-5.43 (m, 8H).

Example 103 trans-3,4-bis(((11Z,14Z)-Icos-11,14-dienyloxy)methyl)pyrrolidine (Compound 103)

Compound 103 (316 mg, 85.2%) was obtained in the same manner as that in Example 1, by using Compound VI-25 (420 mg, 0.542 mmol) obtained in Reference Example 27.

ESI-MS m/z: 685 (M+H)$^+$; $^1$H-NMR (CDCl$_3$) δ: 0.89 (t, J=6.8 Hz, 6H), 1.27-1.40 (m, 40H), 1.50-1.59 (m, 4H), 1.97-2.08 (m, 10H), 2.69 (dd, J=11.1, 5.8 Hz, 2H), 2.77 (t, J=5.8 Hz, 4H), 3.06 (dd, J=11.1, 7.3 Hz, 2H), 3.28-3.46 (m, 8H), 5.28-5.43 (m, 8H).

Example 104 trans-3,4-bis(((Z)-Octadec-9-enoyloxy)methyl)pyrrolidine (compound 104)

Compound XIII-1 (278 mg, 0.366 mmol) obtained in Reference Example 28 was dissolved in dichloromethane (6 mL), and stirred at room temperature for 3 hours after adding trifluoroacetic acid (0.563 mL, 7.31 mmol). The aqueous layer was extracted with chloroform after adding a saturated sodium bicarbonate aqueous solution to the reaction mixture. The organic layer was washed with saturated brine, dried over anhydrous magnesium sulfate, and concentrated under reduced pressure after filtration. The resulting residue was dissolved in a small amount of methanol, and adsorbed on the upper part of BONDESIL-SCX (VARIAN; 6 g) charged into a plastic column. After washing with methanol, the target was eluted with an ammonia•methanol solution (Tokyo Chemical Industry Co., Ltd.; 2 mol/L). The fraction comprising the target was concentrated under reduced pressure to give compound 104 (162 mg, 67.2%).

ESI-MS m/z: 661 (M+H)$^+$; $^1$H-NMR (CDCl$_3$) δ: 0.88 (t, J=6.6 Hz, 6H), 1.27-1.35 (m, 40H), 1.56-1.64 (m, 4H), 2.01 (q, J=5.9 Hz, 8H), 2.09-2.16 (m, 2H), 2.30 (t, J=7.5 Hz, 4H), 2.72 (dd, J=11.3, 5.5 Hz, 2H), 3.11 (dd, J=11.3, 7.1 Hz, 2H), 3.99-4.12 (m, 4H), 5.29-5.40 (m, 4H).

Example 105 trans-3,4-bis(((9Z,12Z)-Octadec-9,12-dienoyloxy)methyl)pyrrolidine (Compound 105)

Compound 105 (224 mg, 73.6%) was obtained in the same manner as that in Example 104, by using Compound XIII-2 (350 mg, 0.463 mmol) obtained in Reference Example 29.

ESI-MS m/z: 657 (M+H)$^+$; $^1$H-NMR (CDCl$_3$) δ: 0.89 (t, J=6.8 Hz, 6H), 1.26-1.40 (m, 28H), 1.57-1.66 (m, 4H), 2.05 (q, J=6.6 Hz, 8H), 2.09-2.17 (m, 2H), 2.31 (t, J=7.5 Hz, 4H), 2.72 (dd, J=11.3, 6.0 Hz, 2H), 2.77 (t, J=6.2 Hz, 4H), 3.11 (dd, J=11.3, 7.3 Hz, 2H), 3.99-4.13 (m, 4H), 5.28-5.43 (m, 8H).

Example 106 trans-1-Methyl-3,4-bis(((Z)-octadec-9-enyloxy)methyl)pyrrolidine (Compound 106)

Compound 106 (87.3 mg, 79.9%) was obtained in the same manner as that in Example 10, by using Compound 101 (107 mg, 0.169 mmol) obtained in Example 101.

ESI-MS m/z: 647 (M+H)$^+$; $^1$H-NMR (CDCl$_3$) δ: 0.88 (t, J=6.8 Hz, 6H), 1.27-1.36 (m, 44H), 1.50-1.59 (m, 4H), 1.98-2.09 (m, 10H), 2.31 (s, 3H), 2.36 (dd, J=9.2, 5.3 Hz, 2H), 2.64 (dd, J=9.2, 7.0 Hz, 2H), 3.30-3.45 (m, 8H), 5.29-5.40 (m, 4H).

Example 107 trans-1-Methyl-3,4-bis(((9Z,12Z)-octadec-9,12-dienyloxy)methyl)pyrrolidine (Compound 107)

Compound 107 (109 mg, 86.7%) was obtained in the same manner as that in Example 10, by using Compound 102 (123 mg, 0.196 mmol) obtained in Example 102.

ESI-MS m/z: 643 (M+H)$^+$; $^1$H-NMR (CDCl$_3$) δ: 0.89 (t, J=6.8 Hz, 6H), 1.26-1.40 (m, 32H), 1.50-1.60 (m, 4H), 2.05 (q, J=6.6 Hz, 10H), 2.31 (s, 3H), 2.36 (dd, J=9.2, 5.5 Hz, 2H), 2.64 (dd, J=9.2, 7.0 Hz, 2H), 2.77 (t, J=5.9 Hz, 4H), 3.30-3.45 (m, 8H), 5.28-5.43 (m, 8H).

Example 108 trans-3,4-bis(((11Z,14Z)-Icos-11,14-dienyloxy)methyl)-1-methylpyrrolidine (Compound 108)

Compound 108 (145 mg, 85.9%) was obtained in the same manner as that in Example 10, by using Compound 103 (165 mg, 0.241 mmol) obtained in Example 103.

ESI-MS m/z: 699 (M+H)$^+$; $^1$H-NMR (CDCl$_3$) δ: 0.89 (t, J=6.8 Hz, 6H), 1.27-1.40 (m, 40H), 1.50-1.60 (m, 4H), 2.05 (q, J=6.2 Hz, 10H), 2.31 (s, 3H), 2.36 (dd, J=9.2, 5.8 Hz, 2H), 2.64 (dd, J=9.2, 7.3 Hz, 2H), 2.77 (t, J=5.8 Hz, 4H), 3.31-3.45 (m, 8H), 5.29-5.43 (m, 8H).

Example 109 trans-1-Methyl-3,4-bis(((Z)-octadec-9-enoyloxy)methyl)pyrrolidine (Compound 109)

Compound 109 (47 mg, 92%) was obtained in the same manner as that in Example 10, by using Compound 104 (50 mg, 0.076 mmol) obtained in Example 104.

ESI-MS m/z: 675 (M+H)$^+$; $^1$H-NMR (CDCl$_3$) δ: 0.88 (t, J=6.6 Hz, 6H), 1.26-1.35 (m, 40H), 1.56-1.65 (m, 4H), 2.01 (q, J=5.5 Hz, 8H), 2.15-2.24 (m, 2H), 2.27-2.37 (m, 9H), 2.67 (dd, J=9.3, 7.1 Hz, 2H), 3.99-4.12 (m, 4H), 5.29-5.40 (m, 4H).

Example 110 trans-1-Methyl-3,4-bis(((9Z,12Z)-octadec-9,12-dienoyloxy)methyl)pyrrolidine (Compound 110)

Compound 110 (66 mg, 81%) was obtained in the same manner as that in Example 10, by using Compound 105 (80 mg, 0.12 mmol) obtained in Example 105.

ESI-MS m/z: 671 (M+H)$^+$; $^1$H-NMR (CDCl$_3$) δ: 0.89 (t, J=6.8 Hz, 6H), 1.25-1.40 (m, 28H), 1.57-1.66 (m, 4H), 2.05 (q, J=6.7 Hz, 8H), 2.13-2.24 (m, 2H), 2.27-2.37 (m, 9H), 2.66 (dd, J=9.2, 7.3 Hz, 2H), 2.77 (t, J=5.7 Hz, 4H), 3.99-4.12 (m, 4H), 5.28-5.43 (m, 8H).

Example 111 trans-1,1-Dimethyl-3,4-bis(((Z)-octadec-9-enyloxy)methyl)pyrrolidinium chloride (Compound 111)

Compound 111 (85.9 mg, 86.6%) was obtained in the same manner as that in Example 22, by using Compound 101 (90.0 mg, 0.142 mmol) obtained in Example 101.

ESI-MS m/z: 661 M$^+$; $^1$H-NMR (CDCl$_3$) δ: 0.88 (t, J=6.6 Hz, 6H), 1.27-1.37 (m, 44H), 1.50-1.58 (m, 4H), 2.01 (q, J=5.9 Hz, 8H), 2.82-2.87 (m, 2H), 3.43 (t, J=6.6 Hz, 4H), 3.48 (s, 6H), 3.49-3.56 (m, 4H), 3.75 (dd, J=11.6, 8.2 Hz, 2H), 4.10 (dd, J=11.6, 8.1 Hz, 2H), 5.29-5.41 (m, 4H).

Example 112 trans-1,1-Dimethyl-3,4-bis(((9Z,12Z)-octadec-9,12-dienoyloxy)methyl)pyrrolidinium chloride (Compound 112)

Compound 112 (107 mg, 96.9%) was obtained in the same manner as that in Example 22, by using Compound 102 (100 mg, 0.159 mmol) obtained in Example 102.

ESI-MS m/z: 657 M$^+$; $^1$H-NMR (CDCl$_3$) δ: 0.89 (t, J=6.8 Hz, 6H), 1.29-1.40 (m, 32H), 1.50-1.58 (m, 4H), 2.05 (q, J=6.7 Hz, 8H), 2.77 (t, J=5.9 Hz, 4H), 2.80-2.87 (m, 2H), 3.43 (t, J=6.6 Hz, 4H), 3.48 (s, 6H), 3.49-3.56 (m, 4H), 3.74 (dd, J=11.6, 8.1 Hz, 2H), 4.09 (dd, J=11.6, 8.1 Hz, 2H), 5.28-5.43 (m, 8H).

Example 113 trans-1,1-Dimethyl-3,4-bis(((Z)-octadec-9-enoyloxy)methyl)pyrrolidinium chloride (Compound 113)

Compound 113 (69.5 mg, 82.0%) was obtained in the same manner as that in Example 22, by using Compound 104 (77.0 mg, 0.117 mmol) obtained in Example 104.

ESI-MS m/z: 689 M$^+$; $^1$H-NMR (CDCl$_3$) δ: 0.88 (t, J=6.6 Hz, 6H), 1.27-1.35 (m, 40H), 1.56-1.65 (m, 4H), 2.01 (q, J=5.5 Hz, 8H), 2.33 (t, J=7.5 Hz, 4H), 2.93 (br s, 2H), 3.57 (s, 6H), 3.86 (dd, J=11.9, 8.6 Hz, 2H), 4.19-4.27 (m, 6H), 5.29-5.40 (m, 4H).

Example 114 trans-1,1-Dimethyl-3,4-bis(((9Z,12Z)-octadec-9,12-dienoyloxy)methyl)pyrrolidinium chloride (Compound 114)

Compound 114 (74.3 mg, 64.4%) was obtained in the same manner as that in Example 22, by using Compound 105 (105 mg, 0.160 mmol) obtained in Example 105.

ESI-MS m/z: 685 M$^+$; $^1$H-NMR (CDCl$_3$) δ: 0.89 (t, J=7.0 Hz, 6H), 1.26-1.40 (m, 28H), 1.57-1.65 (m, 4H), 2.05 (q, J=6.7 Hz, 8H), 2.33 (t, J=7.7 Hz, 4H), 2.77 (t, J=5.9 Hz, 4H), 2.93 (br s, 2H), 3.56 (s, 6H), 3.86 (dd, J=12.1, 8.4 Hz, 2H), 4.19-4.27 (m, 6H), 5.28-5.43 (m, 8H).

Example 115 trans-1-((S)-2,6-Diaminohexanoyl)-3,4-bis(((11Z,14Z)-icos-11,14-dienyloxy)methyl) pyrrolidine (Compound 115)

Compound 115 (72.6 mg, 61.2%) was obtained in the same manner as that in Example 61, by using Compound 103 (100 mg, 0.146 mmol) obtained in Example 103 and (S)-2,6-bis(tert-butoxycarbonylamino)hexanoic acid (WATANABE CHEMICAL INDUSTRIES, LTD.; 80 mg, 0.219 mmol).

ESI-MS m/z: 813 (M+H)$^+$; $^1$H-NMR (CDCl$_3$) δ: 0.89 (t, J=7.0 Hz, 6H), 1.27-1.59 (m, 50H), 2.05 (q, J=6.6 Hz, 8H), 2.17-2.26 (m, 1H), 2.35-2.43 (m, 1H), 2.70 (t, J=5.7 Hz, 2H), 2.77 (t, J=6.0 Hz, 4H), 3.21-3.55 (m, 11H), 3.58-3.80 (m, 2H), 5.29-5.43 (m, 8H).

Example 116

3-(Dimethylamino) propyl bis(2-((Z)-1-oxooctadec-9-enyloxy)ethyl) carbamate (compound 116)

Compound 73 (160 mg, 0.252 mmol) obtained in Example 73 was dissolved in chloroform (2.5 mL), and heat-stirred at 110° C. for 30 minutes with a microwave reactor after adding 3-(dimethylamino) propyl 4-nitrophenyl carbonate hydrochloride (115 mg, 0.379 mmol) synthesized according to the method described in Journal of American Chemical Society (J. Am. Chem. Soc.), 1981, Vol. 103, p. 4194-4199, and triethylamine (0.141 mL, 1.01 mmol). 3-(Dimethylamino) propyl 4-nitrophenyl carbonate hydrochloride (38.4 mg, 0.126 mmol) was added to the reaction mixture, and heat-stirred at 110° C. for 30 minutes with a microwave reactor. After being diluted with chloroform, the reaction mixture was washed with a 1 mol/L sodium hydroxide aqueous solution three times and then with saturated brine, dried over anhydrous magnesium sulfate, and concentrated under reduced pressure after filtration. The resulting residue was purified by silica gel column chromatography (chloroform/methanol=100/0 to 95/5) to give compound 116 (42.6 mg, 22.1%).

ESI-MS m/z: 764 (M+H)$^+$; $^1$H-NMR (CDCl$_3$) δ: 0.88 (t, J=6.6 Hz, 6H), 1.24-1.37 (m, 40H), 1.54-1.65 (m, 4H), 1.78-1.89 (m, 2H), 1.97-2.05 (m, 8H), 2.23 (s, 6H), 2.25-

2.38 (m, 6H), 3.48-3.58 (m, 2H), 3.62 (q, J=5.2 Hz, 2H), 4.11-4.30 (m, 6H), 5.28-5.41 (m, 4H).

Example 117

3-(Dimethylamino) propyl bis(2-((9Z,12Z)-1-oxooctadec-9,12-dienyloxy)ethyl) carbamate (compound 117)

Compound 117 (60.3 mg, 31.5%) was obtained in the same manner as that in Example 116, by using compound 74 (159 mg, 0.252 mmol) obtained in Example 74.

ESI-MS m/z: 760 (M+H)$^+$; $^1$H-NMR (CDCl$_3$) δ: 0.89 (t, J=6.9 Hz, 6H), 1.26-1.38 (m, 28H), 1.58-1.69 (m, 4H), 1.78-1.89 (m, 2H), 2.00-2.09 (m, 8H), 2.23 (s, 6H), 2.26-2.38 (m, 6H), 2.77 (t, J=5.8 Hz, 4H), 3.48-3.57 (m, 2H), 3.62 (q, J=5.3 Hz, 2H), 4.12-4.30 (m, 6H), 5.28-5.44 (m, 8H).

Compounds 118 to 136 can be obtained by using the same methods used in Examples 1 to 117, or by using the method described in WO2009/086558.

Reference Example 30

(3R,4R)-1-Methylpyrrolidine-3,4-diyl di((9Z,12Z)-octadec-9,12-dienoate) (Compound A-3)

Compound A-3 (1.17 g, 95.4%) was obtained in the same manner as that in Example 10, by using Compound 2 (1.20 g, 1.90 mmol) obtained in Example 2.

ESI-MS m/z: 643 (M+H)$^+$; $^1$H-NMR (CDCl$_3$) δ: 0.89 (t, J=7.0 Hz, 6H), 1.31-1.41 (m, 28H), 1.56-1.66 (m, 4H), 2.05 (q, J=6.6 Hz, 8H), 2.29-2.35 (m, 7H), 2.48 (dd, J=10.3, 4.2 Hz, 2H), 2.77 (t, J=5.8 Hz, 4H), 3.04 (dd, J=10.3, 5.8 Hz, 2H), 5.11 (dd, J=5.8, 4.2 Hz, 2H), 5.28-5.43 (m, 8H).

Reference Example 31

(3R,4R)-1-Methylpyrrolidine-3,4-diyl di((Z)-octadec-9-enoate) (Compound A-4)

Compound A-4 (481 mg, 94.0%) was obtained in the same manner as that in Example 10, by using Compound 9 (500 mg, 0.791 mmol) obtained in Example 9.

ESI-MS m/z: 647 (M+H)$^+$; $^1$H-NMR (CDCl$_3$) δ: 0.88 (t, J=6.6 Hz, 6H), 1.27-1.35 (m, 40H), 1.56-1.66 (m, 4H), 2.01 (q, J=6.2 Hz, 8H), 2.32 (t, J=7.7 Hz, 4H), 2.35 (s, 3H), 2.48 (dd, J=10.5, 4.0 Hz, 2H), 3.04 (dd, J=10.5, 5.7 Hz, 2H), 5.10 (dd, J=5.7, 4.0 Hz, 2H), 5.29-5.40 (m, 4H).

Reference Example 32

N-Methyl-N,N-bis(2-((9Z,12Z)-1-oxooctadec-9,12-dienyloxy)ethyl)amine (Compound A-5)

Compound A-5 (348 mg, 54.0%) was obtained in the same manner as that in Reference Example 2, by using N-methyldiethanolamine (Tokyo Chemical Industry Co., Ltd.; 119 mg, 1.00 mmol) and linoleic acid (Aldrich; 617 mg, 2.20 mmol).

ESI-MS m/z: 645 (M+H)$^+$; $^1$H-NMR (CDCl$_3$) δ: 0.89 (t, J=6.8 Hz, 6H), 1.27-1.38 (m, 28H), 1.56-1.66 (m, 4H), 2.00-2.09 (m, 8H), 2.31 (t, J=7.6 Hz, 4H), 2.35 (s, 3H), 2.70 (t, J=5.9 Hz, 4H), 2.77 (t, J=5.8 Hz, 4H), 4.16 (t, J=5.9 Hz, 4H), 5.28-5.42 (m, 8H).

Reference Example 33

N-Methyl-N,N-bis(2-((Z)-1-oxooctadec-9-enyloxy)ethyl)amine (Compound A-6)

Compound A-6 (333 mg, 51.4%) was obtained in the same manner as that in Reference Example 2, by using N-methyldiethanolamine (Tokyo Chemical Industry Co., Ltd.; 119 mg, 1.00 mmol) and oleic acid (Tokyo Chemical Industry Co., Ltd.; 621 mg, 2.20 mmol).

ESI-MS m/z: 649 (M+H)$^+$; $^1$H-NMR (CDCl$_3$) δ: 0.88 (t, J=6.8 Hz, 6H), 1.25-1.36 (m, 40H), 1.56-1.67 (m, 4H), 1.97-2.04 (m, 8H), 2.30 (t, J=7.6 Hz, 4H), 2.35 (s, 3H), 2.70 (t, J=5.9 Hz, 4H), 4.16 (t, J=5.9 Hz, 4H), 5.28-5.39 (m, 4H).

The composition of the present invention is described below in detail using Examples and Test Examples. It should be noted that the present invention is in no way limited by the following Examples and Test Examples.

Example 118

Preparations were produced using the compounds obtained in Examples 1 to 117, as follows.

Anti-APO-B siRNA was used as the nucleic acid. Anti-APO-B siRNA suppresses expression of an apolipoprotein-B (hereinafter, "apo-b") gene and has a sense strand with the base sequence 5'-GmUCAmUCACAC-mUGAAmUACCAAmU-3' (the sugars attached to the bases appended with m are 2'-O-methyl-substituted riboses), and an antisense strand with the base sequence 5'-AUUG-GUAUUCAGUGUGAUGACAC-3' (the 5'-end is phosphorylated). The sense strand and the antisense strand were obtained from Nippon EGT or Hokkaido System Science Co., Ltd., and annealed to prepare the nucleic acid (hereinafter, "apo-b siRNA").

A solution comprising the constituent components of a lipid membrane was prepared by dissolving each of the weighed samples in 90 vol % ethanol in 8.947/1.059/5.708/13.697 mmol/L [compounds 1 to 117 obtained in Examples 1 to 117/1,2-dimyristoyl-sn-glycero-3-phosphoethanolamine-A-(methoxy(polyethylene glycol)-2000) (PEG-DMPE, N-(carbonylmethoxypolyethylene glycol 2000)-1,2-dimyristoyl-sn-glycero-3-phosphoethanolamine sodium salt, NOF Corporation)/distearoylphosphatidyl choline (DSPC, 1,2-distearoyl-sn-glycero-3-phosphocholine, NOF Corporation)/cholesterol (Avanti Polar Lipids)]. Separately, apo-b siRNA/distilled water (24 mg/mL) was diluted with a Tris-EDTA buffer (200 mM Tris-HCl, 20 mM EDTA, Invitrogen) and a 20 mM citric acid buffer (pH 5.0) to prepare a 1.5 mg/mL apo-b siRNA aqueous solution (2 mM Tris-EDTA buffer, pH 5.0).

The resulting lipid solution was heated to 37° C., and a 100-4 portion was transferred to a preparation container. The apo-b siRNA aqueous solution (100 µL) was then added thereto while being stirred. Then, a 20 mM citric acid buffer (containing 300 mM NaCl, pH 6.0; 200 µL) was added to the lipid nucleic acid mixed suspension (200 µL) while being stirred. The siRNA concentration was brought to 10 µM by dropping a Dulbecco phosphate buffer (DPBS, Invitrogen; 662 µL), and preparations (compositions comprising compounds 1 to 117 and the nucleic acid) were obtained.

The average particle diameter of the liposomes in each preparation was measured with a particle diameter measurement device (Malvern; Zetasizer Nano ZS). The results are presented in Table 18.

TABLE 18

| Compound No. | 1 | 2 | 3 | 4 | 5 | 6 | 7 | 8 | 9 | 10 |
|---|---|---|---|---|---|---|---|---|---|---|
| Particle diameter of Preparetion (nm) | 137.4 | 139.6 | 152.8 | 160.6 | 154.2 | 140.3 | 148.7 | 143.8 | 141.9 | 153.9 |
| Compound No. | 11 | 12 | 13 | 14 | 15 | 16 | 17 | 18 | 19 | 20 |
| Particle diameter of Preparetion (nm) | 135.8 | 161.3 | 150.2 | 139.3 | 139.1 | 143.2 | 142.6 | 146.4 | 122.4 | 107.5 |
| Compound No. | 21 | 22 | 23 | 24 | 25 | 26 | 27 | 28 | 29 | 30 |
| Particle diameter of Preparetion (nm) | 112.4 | 115.6 | 108.7 | 160.7 | 126.0 | 133.9 | 135.2 | 132.2 | 122.5 | 132.7 |
| Compound No. | 31 | 32 | 33 | 34 | 35 | 36 | 37 | 38 | 39 | 40 |
| Particle diameter of Preparetion (nm) | 100.7 | 154.2 | 152.1 | 165.7 | 126.5 | 137.2 | 151.3 | 157.2 | 444.5 | 133.8 |
| Compound No. | 41 | 42 | 43 | 44 | 45 | 46 | 47 | 48 | 49 | 50 |
| Particle diameter of Preparetion (nm) | 134.4 | 131.3 | 150.0 | 143.5 | 136.3 | 192.0 | 125.8 | 135.0 | 141.7 | 129.2 |
| Compound No. | 51 | 52 | 53 | 54 | 55 | 56 | 57 | 58 | 59 | 60 |
| Particle diameter of Preparetion (nm) | 123.9 | 118.9 | 152.4 | 148.9 | 139.6 | 120.3 | 159.2 | 151.8 | 116.7 | 125.3 |
| Compound No. | 61 | 62 | 63 | 64 | 65 | 66 | 67 | 68 | 69 | 70 |
| Particle diameter of Preparetion (nm) | 125.9 | 151.3 | 143.0 | 146.0 | 128.9 | 137.4 | 127.6 | 132.4 | 136.8 | 145.6 |
| Compound No. | 71 | 72 | 73 | 74 | 75 | 76 | 77 | 78 | 79 | 80 |
| Particle diameter of Preparetion (nm) | 148.4 | 130.6 | 146.8 | 128.4 | 124.0 | 133.6 | 119.7 | 131.4 | 116.5 | 110.3 |
| Compound No. | 81 | 82 | 83 | 84 | 85 | 86 | 87 | 88 | 89 | 90 |
| Particle diameter of Preparetion (nm) | 103.4 | 125.7 | 169.1 | 120.2 | 120.1 | 128.4 | 136.3 | 131.9 | 121.5 | 120.8 |
| Compound No. | 91 | 92 | 93 | 94 | 95 | 96 | 97 | 98 | 99 | 100 |
| Particle diameter of Preparetion (nm) | 125.4 | 143.9 | 135.1 | 137.3 | 128.3 | 133.2 | 133.0 | 124.1 | 129.6 | 135.1 |
| Compound No. | 101 | 102 | 103 | 104 | 105 | 106 | 107 | 108 | 109 | 110 |
| Particle diameter of Preparetion (nm) | 148.7 | 133.0 | 141.8 | 141.5 | 125.6 | 139.2 | 139.1 | 144.9 | 129.6 | 131.6 |
| Compound No. | 111 | 112 | 113 | 114 | 115 | 116 | 117 | | | |
| Particle diameter of Preparetion (nm) | 112.0 | 119.2 | 103.5 | 108.2 | 152.8 | 154.1 | 155.9 | | | |

Comparative Example 1

A preparation was obtained in the same manner as that in Example 118, except that compound 1 was changed to DOTAP (compound A-1, Avanti Polar Lipids). The average particle diameter of the liposomes in the preparation was 104.0 nm.

Comparative Example 2

A preparation was obtained in the same manner as that in Example 118, except that compound 1 was changed to DLinDMA (Compound A-2). The Compound A-2 was produced by a method described in WO2005/121348. The average particle diameter of the liposomes in the preparation was 131.6 nm.

Comparative Example 3

A preparation was obtained in the same manner as that in Example 118 by using Compound A-3 obtained in Reference Example 30. The average particle diameter of the liposomes in the preparation was 141.0 nm.

Comparative Example 4

A preparation was obtained in the same manner as that in Example 118 by using Compound A-4 obtained in Reference Example 31. The average particle diameter of the liposomes in the preparation was 131.1 nm.

Comparative Example 5

A preparation was obtained in the same manner as that in Example 118 by using Compound A-5 obtained in Reference Example 32. The average particle diameter of the liposomes in the preparation was 136.4 nm.

Comparative Example 6

A preparation was obtained in the same manner as that in Example 118 by using Compound A-6 obtained in Reference Example 33. The average particle diameter of the liposomes in the preparation was 139.5 nm.

Comparative Example 7

A preparation was obtained in the same manner as that in Example 118 by using Compound VI-3 obtained in Reference Example 3. The average particle diameter of the liposomes in the preparation was 167.8 nm.

Comparative Example 8

A preparation was obtained in the same manner as that in Example 118 by using Compound VI-4 obtained in Reference Example 4. The average particle diameter of the liposomes in the preparation was 157.8 nm.

The structures of Compound A-1 to 6 and Compound VI-3 to 4 used in Comparative Examples are shown in Tables 19.

TABLE 19

| Compound No. | Structure |
|---|---|
| A-1 | 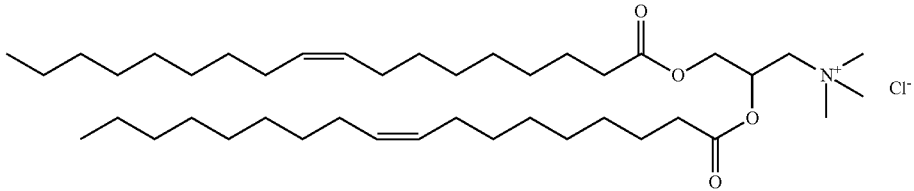 [SMILES: CCCCCCCC/C=C\CCCCCCCC(=O)OCC(C[N+](C)(C)C)OC(=O)CCCCCCC/C=C\CCCCCCCC ; [Cl-]] |
| A-2 | 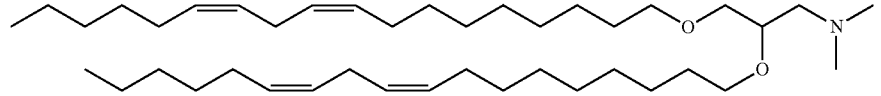 |
| A-3 | 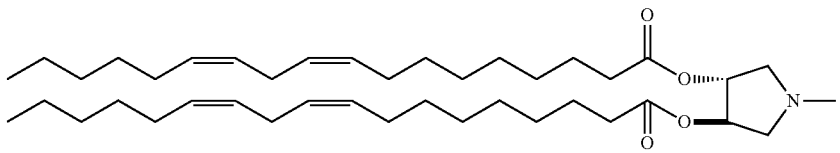 [SMILES: CCCCC/C=C\C/C=C\CCCCCCCC(=O)O[C@@H]1CN(C)C[C@H]1OC(=O)CCCCCCC/C=C\C/C=C\CCCCC] |
| A-4 | 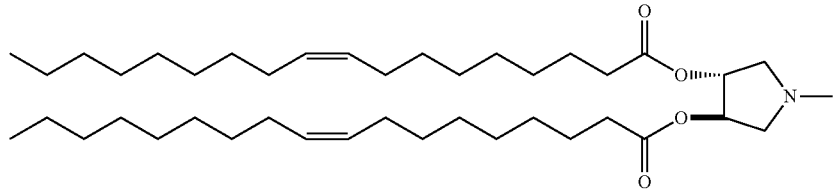 [SMILES: CCCCCCCC/C=C\CCCCCCCC(=O)O[C@@H]1CN(C)C[C@H]1OC(=O)CCCCCCC/C=C\CCCCCCCC] |
| A-5 | 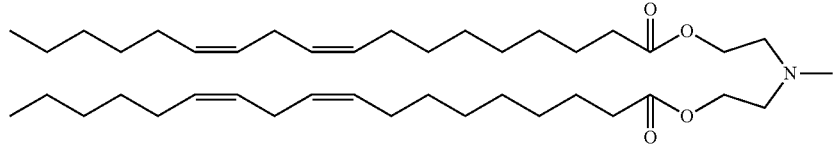 |
| A-6 | 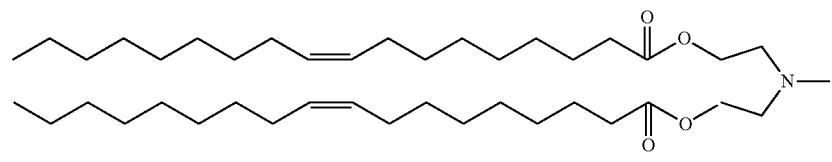 |
| VI-3 | 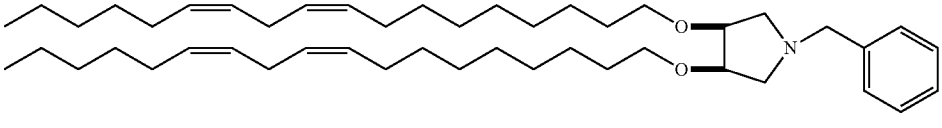 |
| VI-4 | 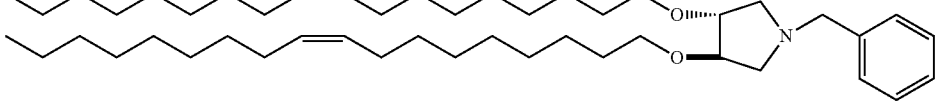 |

Test Example 1

The preparations obtained in Example 118 (compositions comprising compounds 1 to 115 and the nucleic acid), and the preparations obtained in Comparative Examples 1 to 8 were introduced into human liver cancer-derived cell line HepG2 (HB-8065) by using the following method.

Each preparation diluted with Opti-MEM (GIBCO; 31985) to make the nucleic acid final concentrations 3 to 100 nM was dispensed in a 96-well culture plate in 20-4 portions. Then, HepG2 cells suspended in MEM containing 1.25% fetal bovine serum (FBS; SAFC Biosciences; 12203C) were inoculated in 6250 cells/80 µL/well, and cultured under 37° C., 5% $CO_2$ conditions to introduce the preparation into the HepG2 cells. Untreated cells were also inoculated as a negative control group.

The cells after the introduction of the preparation were cultured in a 37° C., 5% $CO_2$ incubator for 24 hours, and washed with ice-cooled phosphate buffered saline (PBS; GIBCO; 14190). Total RNA was collected, and cDNA was produced by reverse transcription reaction using the total RNA as a template, using a Cells-to-Ct Kit (Applied Bioscience; ABI; AM1728) according to the protocol attached to the kit.

By using the cDNA as a template, a PCR reaction was performed for the apo-b gene and the constitutively expressed gene D-glyceraldehyde-3-phosphate dehydrogenase (hereinafter, "gapdh") gene using a universal probe library (Roche Applied Science; 04683633001) as the probe. For the PCR, ABI7900HT Fast (ABI) was used according to the protocol attached to the system. The mRNA amplification amounts were measured, and a quasi-quantitative value for the apo-b mRNA was calculated using the gapdh mRNA amplification amount as the internal control. The apo-b mRNA level and the gapdh mRNA amplification amount in the negative control group were also measured in the same manner, and a quasi-quantitative value for the apo-b mRNA was calculated using the gapdh mRNA amplification amount as the internal control.

Figure 13:
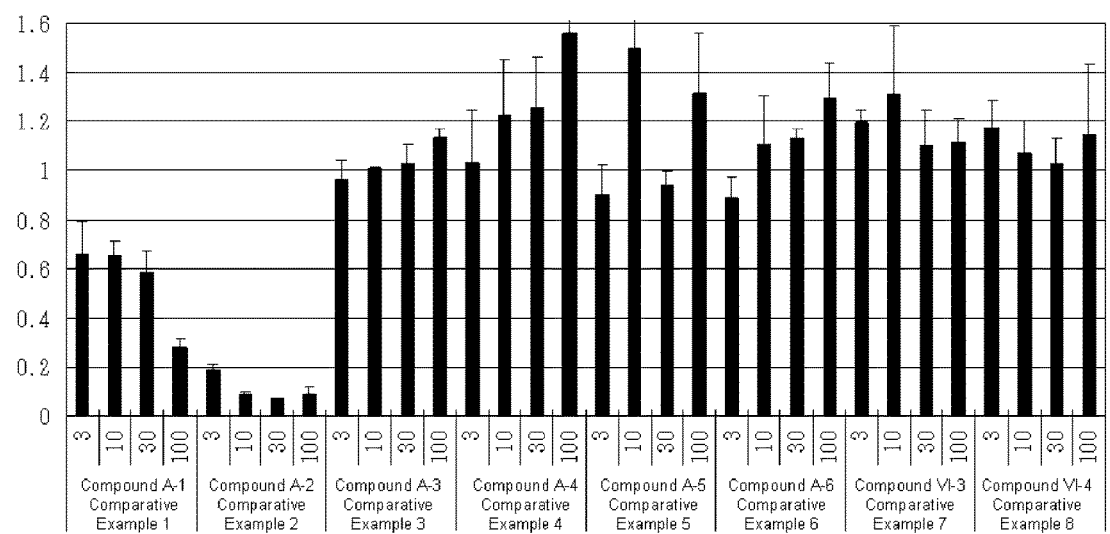
FIG. 13 shows the expression rate of target gene mRNA after the introduction of the preparations obtained in Comparative Examples 1 to 8 into cells as that in FIG. 1.

The apo-b mRNA expression rate was determined from the calculated apo-b mRNA quasi-quantitative value relative to the apo-b mRNA quasi-quantitative value of the negative control as 1. The results for Example 118 are presented in FIGS. 1 to 12, and the results for Comparative Examples 1 to 8 are presented in FIG. 13. The vertical axis represents the target gene mRNA expression rate relative to the negative control taken at 1. The horizontal axis represents nucleic acid concentration (nM), and the compound numbers and example numbers of the cationic lipids used.

As is clear FIGS. 1 to 12, the apo-b gene mRNA expression rate was suppressed after the introduction of the preparations obtained in Example 118 (compositions comprising the apo-b gene expression-suppressing anti-APO-B siRNA, and compounds 1 to 115) into the human liver cancer-derived cell line HepG2. On the other hand, as is clear FIG. 13, the apo-b gene mRNA expression rate was not suppressed after the introduction of the preparations obtained in Comparative Examples 3 to 8 (compositions comprising the apo-b gene expression-suppressing anti-APO-B siRNA, and compounds A-3 to 6, VI-3 and VI-4) into the human liver cancer-derived cell line HepG2.

It was therefore found that the composition of the present invention can be used to introduce nucleic acid into cells and the like, and that the cationic lipid of the present invention represents a novel cationic lipid that allows nucleic acid to be easily introduced into cells.

INDUSTRIAL APPLICABILITY

A composition comprising the novel cationic lipid of the present invention and a nucleic acid can be used to easily introduce the nucleic acid into, for example, cells and the like through administration to mammals and the like.

SEQUENCE LISTING FREE TEXT

SEQ No. 1: siRNA sense
SEQ No. 2: siRNA antisense
SEQ No. 2: 5'-phosphorylated Adenosine

SEQUENCE LISTING

Apo-b siRNA.txt

---

The invention claimed is:

1. A cationic lipid represented by formula (I):

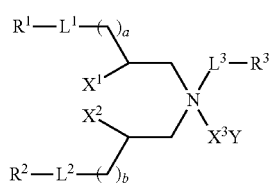

wherein:

$R^1$ and $R^2$ are, the same or different, each linear or branched alkyl, alkenyl or alkynyl having: 12 to 24 carbon atoms, or $R^1$ and $R^2$ are combined together to form dialkylmethylene, dialkenylmethylene, dialkynylmethylene or alkylalkenylmethylene;

$X^1$ and $X^2$ are hydrogen atoms, or combined together to form a single bond or alkylene;

$X^3$ and Y are absent;

a and b are, the same or different, 1 to 3;

$L^3$ is a single bond;

$R^3$ is a hydrogen atom; and $L^1$ and $L^2$ are, the same or different, —O— or

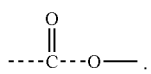

2. The cationic lipid according to claim 1, wherein $L^1$ and $L^2$ are —O—, and $R^1$ and $R^2$ are dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadec-9,12-dienyl, (9Z, 12Z, 15Z)-octadec-9, 12, 15-trienyl, (Z)-icos-11-enyl, (11Z,14Z)-icos-11,14-dienyl, 3,7, 11-trimethyldodeca-2,6,10-trienyl or 3,7, 11,15-tetramethylhexadec-2-enyl.

3. The cationic lipid according to claim 1, wherein $L^1$ and $L^2$ are

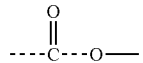

and $R^1$ and $R^2$ are tridecyl, pentadecyl, heptadecyl, nonadecyl, heneicosyl, tricosyl, (Z)-tridec-8-enyl, (Z)-pentadec-8-enyl, (Z)-heptadec-5-envl, (Z)-heptadec-8-enyl, (E)-heptadec-8-enyl, (Z)-heptadec-10-enyl, (8Z,11Z)-heptadec-8,11-dienyl, (8Z, 11Z,14Z)-octadec-8, 11,14-trienyl, (Z)-nonadec-10-enyl, (10Z,13Z)-nonadec-10,13-dienyl, (11Z, 14Z)-icos-11,14-dienyl, 2,6,10-trimethylundec-1,5,9-trienyl or 2,6,10,14-tetramethylpentadec-1-enyl.

4. The cationic lipid according to anyone of claims 1 to 3, wherein a and b are both 1.

5. A composition that comprises the cationic lipid according to anyone of claims 1 to 3, and a nucleic acid.

6. A composition comprising a complex particle of the cationic lipid according to any one of claims 1 to 3 and a nucleic acid, or a complex particle of a nucleic acid and a combination of the cationic lipid and a neutral lipid and/or a polymer.

7. A composition comprising a lipid particle constituted of a complex particle of the cationic lipid according to anyone of claims 1 to 3 and a nucleic acid, or a complex particle of a nucleic acid and a combination of the cationic lipid and a neutral lipid and/or a polymer, and a lipid membrane that encapsulates the complex particle.

8. The composition according to claim 6, wherein the nucleic acid is a nucleic acid having an activity of suppressing the expression of the target gene by utilizing RNA interference (RNAi).

9. The composition according to claim 8, wherein the target gene is a gene associated with tumor or inflammation.

10. A method for introducing the nucleic acid into a cell with the composition according to claim 6 wherein the method of the introduction into a cell is a method of introduction into a cell by intravenous administration.

11. The method according to claim 10, wherein the cell is a cell at a tumor or inflammation site of a mammal.

12. The method according to claim 10, wherein the cell is a cell in the liver, lungs, kidneys or spleen of a mammal.

* * * * *

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: siRNA sense
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (21)..(21)
<223> OTHER INFORMATION: um

<400> SEQUENCE: 1
gucaucacac ugaauaccaa u                                              21

<210> SEQ ID NO 2
<211> LENGTH: 23
<212> TYPE: RNA
<213> ORGANISM: Artificial Sequence
```

```
<220> FEATURE:
<223> OTHER INFORMATION: siRNA antisense
<220> FEATURE:
<221> NAME/KEY: misc_feature
<222> LOCATION: (1)..(1)
<223> OTHER INFORMATION: 5'-phosphorylated Adenosine

<400> SEQUENCE: 2
auugguauuc agugugauga cac                                              23
```